US008741894B2

(12) United States Patent
Ly et al.

(10) Patent No.: US 8,741,894 B2
(45) Date of Patent: Jun. 3, 2014

(54) ARYLSULFONAMIDE CCR3 ANTAGONISTS

(75) Inventors: Tai Wei Ly, San Diego, CA (US); Garrett Thomas Potter, Redlands, CA (US); Jared Andrew Forrester, Castle Rock, CO (US)

(73) Assignee: Axikin Pharmaceuticals, Inc., San Diego, CA (US)

( * ) Notice: Subject to any disclaimer, the term of this patent is extended or adjusted under 35 U.S.C. 154(b) by 26 days.

(21) Appl. No.: 13/050,831

(22) Filed: Mar. 17, 2011

(65) Prior Publication Data

US 2011/0230487 A1    Sep. 22, 2011

Related U.S. Application Data

(60) Provisional application No. 61/314,971, filed on Mar. 17, 2010.

(51) Int. Cl.
| | | |
|---|---|---|
| *A61K 31/5377* | (2006.01) | |
| *A61K 31/4468* | (2006.01) | |
| *A61K 31/454* | (2006.01) | |
| *A61K 31/4545* | (2006.01) | |
| *A61K 31/496* | (2006.01) | |
| *C07D 211/96* | (2006.01) | |
| *C07D 401/12* | (2006.01) | |
| *C07D 401/04* | (2006.01) | |
| *C07D 413/12* | (2006.01) | |

(52) U.S. Cl.
USPC .......... 514/227.8; 514/237.2; 514/253.01; 514/315; 514/316; 514/326; 544/58.6; 544/130; 544/360; 546/190; 546/209; 546/210; 546/214; 546/223; 546/224; 546/244

(58) Field of Classification Search
None
See application file for complete search history.

(56) References Cited

U.S. PATENT DOCUMENTS

| | | | |
|---|---|---|---|
| 2,275,354 | A | 3/1942 | Ewins et al. |
| 3,819,639 | A | 6/1974 | Delarge et al. |
| 4,233,409 | A | 11/1980 | Bulkley |
| 5,041,498 | A | 8/1991 | Hare et al. |
| 5,605,963 | A | 2/1997 | Leitz et al. |
| 5,696,204 | A | 12/1997 | Eichenauer et al. |
| 5,708,079 | A | 1/1998 | Eichenauer et al. |
| 5,883,190 | A | 3/1999 | Eichenauer |
| 7,674,797 | B2 | 3/2010 | Li et al. |
| 7,700,586 | B2 | 4/2010 | Li et al. |
| 2005/0070582 | A1 | 3/2005 | Li et al. |
| 2007/0155725 | A1 | 7/2007 | Li et al. |
| 2009/0286771 | A1 | 11/2009 | Li et al. |
| 2010/0204213 | A1 | 8/2010 | Li et al. |

FOREIGN PATENT DOCUMENTS

| | | |
|---|---|---|
| DE | 10008419 | 8/2001 |
| DE | 10008420 | 8/2001 |
| WO | WO 8905836 | 6/1989 |
| WO | WO 99/55324 | 11/1999 |
| WO | WO 00/42003 | 7/2000 |
| WO | WO 00/76513 | 12/2000 |
| WO | WO 00/76514 | 12/2000 |
| WO | WO 01/32604 | 5/2001 |
| WO | WO 03/022277 | 3/2003 |
| WO | WO 03/025061 | 3/2003 |
| WO | WO 2004/084898 | 10/2004 |
| WO | WO 2006/020598 | * 2/2006 |
| WO | WO 2010/123956 | * 10/2010 |

OTHER PUBLICATIONS

Byrn et al., Solid-State Chemistry of Drugs (2nd Ed. 1999) (pp. 233-247).*
"NAEP's asthma bulletin board," http://www.asthma.co.za/news01.htm, accessed Aug. 5, 2008.
"Chemokine CCR3 Antagonists," Expert Opinion on Therapeutic Patents, 10(9): 1455-1459 (2000).
Alaaeddine et al., "Production of the Chemokine RANTES by Articular Chrondrocytes and Role in Cartilage Degradation," Arthritis & Rheumatism, vol. 44, No. 7, pp. 1633-1643 (2001).
Ancuta et al., "CD16+ Monocyte-Derived Macrophages Activate Resting T cells for HIV Infection by Producing CCR3 and CCR4 Ligands," J. Immunol., vol. 176, pp. 5760-5771 (2006).
Aust et al., "Grave's Disease Is Associated With an Altered CXCR3 and CCR5 Expression in Thyroid-Derived Compared to Peripheral Blood Lymphocytes," Clin. Exp. Immunol., vol. 127, pp. 479-485 (2001).
Bertrand et al., "CCR3 Blockade as a New Therapy for Asthma," Expert Opinion on Investigational Drugs 9(1):43-52 (2000).
Bhattacharya, et al., "Increased Expression of Eotaxin-3 Distinguishes Between Eosinophilic Esophagitis and Gastroesophageal Reflux Disease,"Human Pathology, vol. 38, pp. 1744-1753 (2007).
Blanchard et al., "Eotaxin-3 and a Uniquely Conserved Gene-Expression Profile in Eosinophilic Esophagitis," J. Clin. Invest., vol. 116, No. 2, pp. 536-547 (2006).
Brauniger et al., "Reactions with 2,4-Dinitrofluorobenzene, Especially With Aromatic Amines. I. Reaction Conditions and Synthetic Compounds," Pharmazie, 12, 335-48 (1957).
Bullock et al., "Interplay of Adaptive Th2 Immunity With Eotaxin-3/C-C Chemokine Receptor 3 in Eosinophilic Esophagitis," J. Pediatric Gastroenterolofgy and Nutrition, vol. 45, pp. 22-31 (2007).
Cheadle et al., "Eotaxin-2 and Colorectal Cancer: A Potential Target for Immune Therapy," Human Cancer BioL., vol. 13, No. 19, pp. 5719-5728 (2007).
CHEMCATS Database, Ambinter Stock Screening Collection, Order Nos. 7J-012, 7J-005 and 7J-004 (Jan. 1, 2004).
Chi et al., "C-Reactive Protein Enhances Expression of Chemokine Receptors on Mast Cells," The FASEB Journal, vol. 16, No. 4, p. A690, Abstract 514.2 (2002).

(Continued)

*Primary Examiner* — Alicia L Otton
(74) *Attorney, Agent, or Firm* — Jones Day

(57) ABSTRACT

Provided herein are arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

17 Claims, No Drawings

(56) References Cited

OTHER PUBLICATIONS

Corren, "Allergic Rhinitis and Asthma: How Important Is the Link?," J. Allergy Clin. Immunol., vol. 99, pp. S781-S786 (1997).
DeLarge, "Nouveaux Anti-inflammatoires Derives de la Pyridine," Ann. Pharm. Fr., vol. 31, No. 6, pp. 467-474, English summary at p. 474 (1973).
Dol et al., "Angiotensin ATI Receptor Antagonist Irbesartan Decreases Lesion Size, Chemokine Expression, and Macrophage Accumulation in Apolipoprotein E-Deficient Mice," J. Cardiovascular Pharmacology, vol. 38, pp. 395-405 (2001).
Elsner et al., "Human Eotaxin Represents a Potential Activator of the Respiratory Burst of Human Eosinophils," Eur. J. Immunol., vol. 26, pp. 1919-1925 (1996).
Foster et al., "Elemental Signals Regulating Eosinophil Accumulation in the Lung," Immunoi. Rev., vol. 179, pp. 173-181 (2001).
Gerber et al., "Functional Expression of the Eotaxin Receptor CCR3 in T Lymphocytes Co-Localizing With Eosinophils," Current Biology, vol. 7, pp. 836-843 (1997).
Haley et al., "Overexpression of Eotaxin and the CCR3 Receptor in Human Atherosclerosis: Using Genomic Technology to Idenify a Potential Novel Pathway of Vascular Inflammation," Circulation, vol. 102, pp. 2185-2189 (2000).
Hogaboam et al., "Collagen Deposition in Non-Fibrotic Lung Granuloma Model after Nitric Oxide Inhibition," Am. J. Pathology, vol. 153, No. 6, pp. 1861-1872 (1998).
Hsu et al., "Production of the Chemokine Eotaxin-1 in Osteoarthritis and Its Role in Cartilage Degradation," J. Cellular Biochem., vol. 93, pp. 929-939 (2004).
Huaux et al., "Role of Eotaxin-1 (CCL11) and CC Chemokine Receptor 3 (CCR3) in Bleomycin-Induced Lung Injury and Fibrosis," vol. 167, No. 6, pp. 1485-1496 (2005).
Hunt et al., "Newly Identified Genetic Risk Variants for Celiac Disease Related to the Immune Response," Nature Genetics, vol. 40, No. 4, pp. 395-402 (2008).
Jahnz-Royk et al., "Eotaxin in Serum of Patients With Asthma or Chronic Obstructive Pulmonary Disease: Relationship With Eosophil Cationic Protein and Lung Function,"Mediators of Inflam., vol. 9, pp. 175-179 (2000).
Johrer et al., "Up-Regulation of Functional Chemokine Receptor CCR3 in Human Renal Cell Carcinoma," Human Cancer Biol., vol. 11, No. 7, pp. 2459-2465 (2005).
Joubert et al., "CCR3 Expression and Function in Asthmatic Airway Smooth Muscle Cells," J. Immunol., vol. 175, pp. 2702-2708 (2005).
Katschke et al., "Differential Expression of Chemokine Receptors on Peripheral Blood, Synovial Fluid, and Synovial Tissue Monocytes/ Macrophages in Rheumatoid Arthritis," Arthritis & Rheumatism, vol. 44, No. 5, pp. 1022-1032 (2001).
Kouno et al. "Up-Regulation of CC Chemokine, CCL3L1, and Receptors, CCR3, CCR5 in Human Glioblastoma That Promotes Cell Growth," J. Neuro-Oncology, vol. 70, pp. 301-307 (2004).
Lamkhioued et al., "Increased Expression of Eotaxin in Bronchoaveolar Lavage and Airways of Asthmatics Contributes to the Chemotaxis of Eosinophils to the Site of Inflammation," J. Immunol., vol. 159, pp. 4593-4601 (1997).
Li et al., "Mast Cells/Basophils in the Peripheral Blood of Allergic Individuals Who Are HIV-1 Susceptible Due to Their Surface Expression of CD4 and the Chemokine Receptors CCR3, CCR5 and CXCR4," Blood, vol. 97, No. 11, pp. 3484-3487 (2001).
Marone et al., "Are Mast Cells MASTers in HIV-1 Infection?," Int. Arch. Allergy Immunol., vol. 125, pp. 89-95 (2001).
Marone et al., "Human Mast Cells and Basophils in HIV-1 Infection," Trends Immunol., vol. 22, No. 5., pp. 229-232 (2001).
Mastrukova et al., "The Application of the Hammett Equation to the Theory of Tautomeric Equilibrium—II," Tetrahedron, vol. 19, pp. 357-372 (1963).
Matsukura et al., "Expression of RANTES by Normal Airway Epithelial Cells After Influenza Virus A Infection," Am. J. Respir. Cell and Mol. Biol., vol. 18, pp. 255-264 (1998).

Nissinen et al., "CCR3, CCR5 Interleukin 4, and Interferon-Gamma Expression on Synovial and Peripheral T Cells and Monocytes in Rheumatoid Arthritis," J. Rheumatol., vol. 30, No. 9, pp. 1928-1934 (2003).
Ohagen et al., "Genetic and Functional Analysis of Full-Length Human Immunodeficiency Virus Type 1 Env Genes Derived From Brain and Blood or Patients With AIDS," J. Virology, vol. 77, No. 22, pp. 12336-12345 (2003).
Oliviera et al., "Stem Cell Factor and IgE-Stimulated Murine Mast Cells Produce Chemokines (CCL2, CCL17, CCL22) and Express Chemokine Receptors," Inflamm. Res., vol. 50, pp. 168-174 (2001).
Park et al., "CD4 Receptor-Dependent Entry of Human Immunodeficiency Virus Type-1 env-Pseudotypes into CCR5-, CCR3- and CXCR4-Expressing Human Alveolar Macrophages Is Preferrentially Mediated by the CCR5 Coreceptor," Am. J. Respir. Cell Mol. Biol., vol. 20, pp. 864-871 (1999).
Ponath, "Chemokine Receptor Antagonists: Novel Therapeutics for Inflammation and AIDS," Expert Opinion on Investigational Drugs 7(1): 1-18 (1998).
Rothenberg et al., "Targeted Disruption of the Chemokine Eotaxin Partially Reduces Antigen-induced Tissue Eosophilia," J. Exp. Med., vol. 185, pp. 785-790 (1997).
Ruth et al., "Expression and Participation of Eotaxin During Mycobacterial (Type 1) and Schistosomal (Type 2) Antigen-Elicited Granuloma Formation," J. Immunology, vol. 161, No. 8, pp. 4276-4282 (1998).
Saari et al., "Synthesis and Evaluation of Some Nitrobenzenesulfonamides Containing Nitroisopropyl and (Ureidooxy)methyl Groups as Novel Hypoxic Cell Selective Cytotoxic Agents," J. Med. Chern., 34,3132-3138 (1991).
Sabroe et al., J. Immunol., "Cloning and Characterization of the Guinea Pig Eosinophil Eotaxin Receptor, C-C Chemokine Receptor-3: Blockade Using a Monoclonal Antibody in Vivo," vol. 161, pp. 6139-6147 (1998).
Saito et al., "Selective Regulation of Chemokine Production in Human Epithelial Cells," J. Infect. Dis., vol. 175, pp. 479-504 (1997).
Sallusto et al., "Selective Expression of the Eotaxin Receptor CCR3 by Human T Helper 2 Cells," Science, vol. 277, pp. 2005-2007 (1997).
Silva et al., "Differential expression of chemokines and chemokine receptors in inflammatory periapical diseases," Oral Microbiol. Immunol., vol. 20, pp. 310-316 (2005).
Simchen et al. "Expression and Regulation of Regulated on Activation, Normal T Cells Expressed and Secreted in Thyroid Tissue of Patients with Graves' Disease and Thyroid Autonomy and in Thyroid-Derived Cell Populations," J. Clinical Endocrinology & Metabolism, vol. 85, No. 2, 4758-64 (2000).
Stellato et al., "Cutting Edge: Expression of the C-C Chemokine Receptor CCR3 in Human Airway Epithelial Cells," J. Immunology, 1457-60 (2001).
Sugasawa et al., "Prognostic Significance of Expression of CCL5/ RANTES Receptors in Patients With Gastric Cancer," J. Sergical Oncology, vol. 97, pp. 445-450 (2008).
Teixeira et al., "Increased Serum Levels of CCL11/Eotaxin in Schizophrenia," Progress in Neuro-pharmacology & Biol. Psych., vol. 32, pp. 710-714 (2008).
Terada et al., "Biochemical Properties of Eosinophils and Their Preferential Accumulation Mechanism in Nasal Allergy," J. Allergy Clin. Immunol., vol. 94, pp. 629-642 (1994).
Uguccioni et al., "High Expression of the Chemokine Receptor CCR3 in Human Blood Basophils," J. Clin. Invest., vol. 100, pp. 1137-1143 (1997).
Weeraratna et al., "Alterations in Immunological and Neurological Gene Expression Patterns in Alzheimer's Disease Tissues," Exp. Cell. Res., vol. 313, pp. 450-461 (2007).
White, et al., Identification of Potent, Selective Non-Peptide CC Chemokine Receptor-3 Antagonist That Inhibits Eotaxin-, Eotaxin-2-, and Monocyte Chemotactic Protein-4-Induced Eosinophil Migration, The Journal of biological chemistry, vol. 275, No. 47, pp. 36626-36631 (Nov. 24, 2000).
Xia et al., "Chemokines/Chemokine Receptors in the Central Nervous System and Alzheimer's Disease," J. Neurovirology, vol. 5, pp. 32-41 (1999).

(56) References Cited

OTHER PUBLICATIONS

Xia et al., "Expression of the Chemokine Receptor CXCR3 on Neurons and the Elevated Expression of Its Ligand IP-10 in Reactive Astrocytes: In Vitro ERK1/2 Activation and Role in Alzheimer's Disease," J. Immunol., 108, 227-35 (2000).

Xia et al., "Immunihistochemical Study of the β—Chemokine Receptors of CCR3 and CCR5 and Their Ligands in Normal and Alzheimer's Diseases Brains," Am. J. Pathology, vol. 153, No. 1, pp. 31-36 (1998).

Ying et al., "Enchanced Expression of Eotaxin and CCR3 Mrna and Protein in Atopic Asthma. Association With Airway Hyperresponsiveness and Predominant Colocalization of Eotaxin mRNA to Bronchial Epithelial and Endothelial Cells," Eur. J. Immunol. vol. 27, 3507-3516 (1997).

Non-Final Office Action dated Aug. 19, 2008 in U.S. Patent Application No. 10/550,482.

Final Office Action dated Feb. 19, 2009 in U.S. Patent Application No. 10/550,482.

Notice of Allowance dated Jul. 24, 2009 in U.S. Patent Application No. 10/550,482.

Non-Final Office Action dated Mar. 20,2008 in U.S. Patent Application No. 10/489,029.

Notice of Allowance dated Oct. 30, 2008 in U.S. Patent Application No. 10/489,029.

Non-Final Office Action dated Mar. 13,2009 in U.S. Patent Application No. 10/489,029.

International Search Report dated Dec. 2, 2002 in International Application No. PCT/EP02/09873 published as No. WO 03/022277.

International Preliminary Report on Patentability and Written Opinion dated Aug. 6, 2004 in International Application No. PCT/EP04/002496, Published as No. WO 04/084898.

Foster, "Deuterium isotope effects in the metabolism of drugs and xenobiotics: implications for drug design," Advances in Drug Research, 1985, 41, 1-10.

* cited by examiner

ARYLSULFONAMIDE CCR3 ANTAGONISTS

Priority is claimed herein to U.S. Provisional Application No. 61/314,971, entitled "Arylsulfonamide CCR3 Antagonists," filed Mar. 17, 2010. The above-referenced application is incorporated by reference herein in its entirety.

FIELD

Provided herein are arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

BACKGROUND

CC chemokine receptor 3 (CCR3) is a seven-transmembrane G protein-coupled receptor, which binds to a variety of C—C chemokines, including eotaxin (CCL11), eotaxin-3 (CCL26), MCP-3 (CCL7), MCP-4 (CCL13), and RANTES (CCL5). CCR3 is known to be a major chemokine receptor expressed on allergic inflammatory cells, including eosinophils, basophils, mast cells, and T helper 2-type $CD4^+$ cells (Combadiere et al., *J. Biol. Chem.* 1995, 270, 16491-16494; Post et al., *J. Immunol.* 1995, 155, 5299-5305). Eosinophils have been implicated in the pathogenesis of a number of allergic diseases, such as bronchial asthma (Durham and Kay, *Clin. Allergy* 1985, 15, 411-418; Kroegel et al, *J. Allergy Clin. Immunol.* 1994, 93, 725-734), allergic rhinitis (Durham, *Clin. Exp. Allergy* 1998, 28 Suppl. 2, 11-16), atopic dermatitis (Leung, *J. Allergy Clin. Immunol.* 1999, 104, S99-108), and eosinophilic gastroenteritis (Bischoff et al., *Am. J. Gastro.* 1999, 94, 3521-3529). It has been demonstrated that activated eosinophils release major basic protein (MBP), which blocks inhibitory M2 muscarinic receptors (M2Rs) on nerves, increasing acetylcholine release, and potentiating vagally mediated bronchoconstriction (Evans et al., *J. Clin. Invest.* 1997, 100, 2254-2262).

Numerous reports indicate that CCR3 plays important roles in allergic conditions. For example, it has been reported that, in both atopic and nonatopic asthma patients, there are increases in both mRNA and protein levels of CCR3 and its ligands, eotaxin, eotaxin-2, RANTES, and MCP-4 (Ying et al., *J. Immunol.* 1999, 99, 6321-6329). It has also been demonstrated that CCR3 gene deletion impairs eosinophil recruitment in an acute model of experimental asthma (Humbles et al., *Proc. Natl. Acad. Sci. USA* 2002, 99, 1479-1484; Ma et al., *J. Clin. Invest.* 2002, 109, 621-628; Pope et al., *J. Immunol.* 2005, 175, 5341-5350; Fulkerson et al., *Proc. Natl. Acad. Sci. USA* 2006, 103, 16418-16423). Furthermore, studies have shown that CCR3 antagonists, such as anti-CCR3 monoclonal antibodies, block binding of CCR3-ligands to either CCR3 transfectants or eosinophils, thus blocking chemotaxis of eosinophils induced by C—C chemokines, such as eotaxin, RANTES, or MCP-3 (Heath et al., *J. Clin. Invest.* 1997, 99, 178-184; Grimaldi et al., *J. Leukocyte Biol.* 1999, 65, 846-853; Justice et al., *Am. J. Physiol.* 2003, 284, L168-L178). Therefore, CCR3 antagonists are potentially useful for the treatment of inflammatory diseases, such as allergic rhinitis and allergic asthma. In addition, CCR3 antagonists are also potentially useful blocking infection of CCR3 expressing cells by some microorganisms, such as HIV, as CCR3 is known to be an entry co-receptor for some microorganisms.

SUMMARY OF THE DISCLOSURE

Provided herein are arylsulfonamide compounds of Formulae I and II:

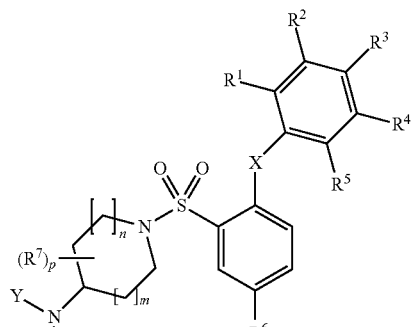

(I)

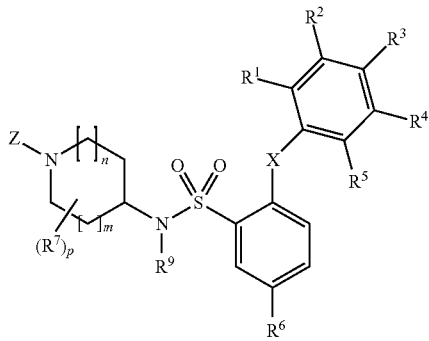

(II)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^6$ are each independently (a) hydrogen, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; (c) deuterium; or (d) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^7$ is (a) hydrogen, halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

X is O or S;

Y is —C(O)R$^{1a}$, —C(S)R$^{1a}$, —C(O)NR$^{1b}$R$^{1c}$, —C(S)NR$^{1b}$R$^{1c}$, —C(O)OR$^{1e}$, —S(O)R$^{1a}$ or —S(O)$_2$R$^{1a}$;

R$^8$ is hydrogen, C$_{1-6}$ alkyl or C$_{3-7}$ cycloalkyl; or

Y and R$^8$ together with the N atom to which they are attached form heteroaryl or heterocyclyl;

Z is —C(O)R$^{1a}$, —C(S)R$^{1a}$, —C(O)NR$^{1b}$R$^{1c}$, —C(S)NR$^{1b}$R$^{1c}$, —C(O)OR$^{1e}$, —S(O)R$^{1a}$ or —S(O)$_2$R$^{1a}$;

m is an integer from 0 to 3;

R$^9$ is hydrogen, C$_{1-6}$ alkyl or C$_{3-7}$ cycloalkyl;

m is an integer from 0 to 3;

n is an integer from 1 to 3;

p is an integer from 1 to 4; and each R$^{1a}$, R$^{1b}$, R$^{1c}$, R$^{1d}$, and R$^{1e}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or each pair of R$^{1b}$ and R$^{1c}$ together with the N atom to which they are attached independently form heteroaryl or heterocyclyl, with the proviso that R$^{1e}$ is not t-butyl or benzyl;

wherein each alkyl, alkenyl, alkynyl, cycloalkyl, aryl, aralkyl, heterocyclyl, and heteroaryl is optionally substituted with one or more groups, each independently selected from (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each optionally substituted with one or more, in one embodiment, one, two, three, or four, substituents Q; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q; or (iii) R$^b$ and R$^c$ together with the N atom to which they are attached form heterocyclyl, optionally substituted with one or more, in one embodiment, one, two, three, or four, substituents Q;

wherein each Q is independently selected from the group consisting of (a) deuterium; (b) cyano, halo, and nitro; (c) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (d) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$;

wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In one embodiment, the compound is of Formula I, with the proviso that if Y and R$^8$ together with the N atom to which they are attached form heteroaryl, the heteroaryl comprises at least one additional O, S, or N atom.

Also provided herein are pharmaceutical compositions comprising a compound disclosed herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; in combination with one or more pharmaceutically acceptable carriers.

Further provided herein is a method for modulating CCR3 activity, comprising contacting a CCR3 with a therapeutically effective amount of a compound disclosed herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

Additionally provided herein is a method for treating, preventing, or ameliorating one or more symptoms of a CCR3-mediated disorder, disease, or condition in a subject, comprising administering to the subject a therapeutically effective amount of a compound disclosed herein, e.g., a compound of Formula I or II, an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "alkyl" refers to a linear or branched saturated monovalent hydrocarbon radical, wherein the alkyl may optionally be substituted as described herein. In certain embodiments, the alkyl is a linear saturated monovalent hydrocarbon radical that has 1 to 20 ($C_{1-20}$), 1 to 15 ($C_{1-15}$), 1 to 10 ($C_{1-10}$, or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one to five, in another embodiment, one, carbon-carbon double bond(s). The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic monovalent hydrocarbon radical, which may be optionally substituted as described herein. In one embodiment, cycloalkyl groups may be saturated, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "aryl" refers to a monovalent monocyclic aromatic group and/or monovalent multicyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "aralkyl" or "aryl-alkyl" refers to a monovalent alkyl group substituted with aryl. In certain embodiments, the alkyl and aryl moieties are optionally substituted as described herein.

The term "alkoxy" refers to the group "—OR" where R is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, and 1,2-dimethylbutoxy.

The term "heteroaryl" refers to a monovalent monocyclic aromatic group and/or multicyclic aromatic group that contain at least one aromatic ring, wherein at least one aromatic ring contains one or more heteroatoms independently selected from O, S, and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, O-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "halogen", "halide" or "halo" refers to fluorine, chlorine, bromine, and/or iodine.

The term "optionally substituted" is intended to mean that a group, such as an alkyl, alkenyl, alkynyl, cycloalkyl, aryl, aralkyl, heteroaryl, or heterocyclyl group, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (b) halo, cyano (—CN), nitro (—$NO_2$), —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heteroaryl or heterocyclyl, optionally substituted with one or more, in one embodiment, one, two, three, or four, substituents Q. As used herein, all groups that can be substituted are "optionally substituted," unless otherwise specified. As used herein, the term "optionally substituted" is also intended to include the substitution of a hydrogen with a deuterium atom.

In one embodiment, each Q is independently selected from the group consisting of (a) deuterium; (b) cyano, halo, and nitro; (c) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (d) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "CCR3" refers to CC chemokine receptor 3 or a variant thereof, which is capable of mediating a cellular response to a variety of chemokines, including, but not limited to, eotaxin (CCL11), eotaxin-3 (CCL26), MCP-3 (CCL7), MCP-4 (CCL13), and RANTES (CCL5). CCR3 variants include proteins substantially homologous to a native CCR3, i.e., proteins having one or more naturally or non-naturally occurring amino acid deletions, insertions or substitutions (e.g., CCR3 derivatives, homologs and fragments), as compared to the amino acid sequence of a native CCR3. The amino acid sequence of a CCR3 variant is at least about 80% identical, at least about 90% identical, or at least about 95% identical to a native CCR3.

The term "CCR3 antagonist" refers to a compound that, e.g., partially or totally blocks, decreases, prevents, inhibits, or downregulates CCR3 activity. The term "CCR3 antagonist" also refers to a compound that binds to, delays the activation of, inactivates, or desensitizes a CCR3 receptor. A CCR3 antagonist may act by interfering with the interaction of a CCR3 receptor and its chemokine ligand, including, but not limited to, eotaxin (CCL11), eotaxin-3 (CCL26), MCP-3 (CCL7), MCP-4 (CCL13), and/or RANTES (CCL5).

The terms "CCR3-mediated disorder or disease" and "a condition, disorder or disease mediated by CCR3" refer to a condition, disorder, or disease characterized by inappropriate, e.g., less than or greater than normal, CCR3 activity. Inappropriate CCR3 functional activity might arise as the result of CCR3 expression in cells which normally do not express CCR3, increased CCR3 expression or degree of intracellular activation, leading to, e.g., inflammatory and immune-related disorders or diseases; or decreased CCR3 expression. A CCR3-mediated condition, disorder or disease may be completely or partially mediated by inappropriate CCR3 activity. In particular, a CCR3-mediated condition, disorder or disease is one in which modulation of a CCR3 receptor results in some effect on the underlying condition or disorder, e.g., a CCR3 antagonist or agonist results in some improvement in at least some of patients being treated.

Compounds

Provided herein are arylsulfonamides which are useful for modulating CCR$^3$ activity. Also provided herein are pharmaceutical compositions which comprise the compounds and methods of use of the compounds and compositions for the treatment of a CCR$^3$-mediated disorder, disease, or condition.

In one embodiment, provided herein are arylsulfonamide compounds of Formulae I and II:

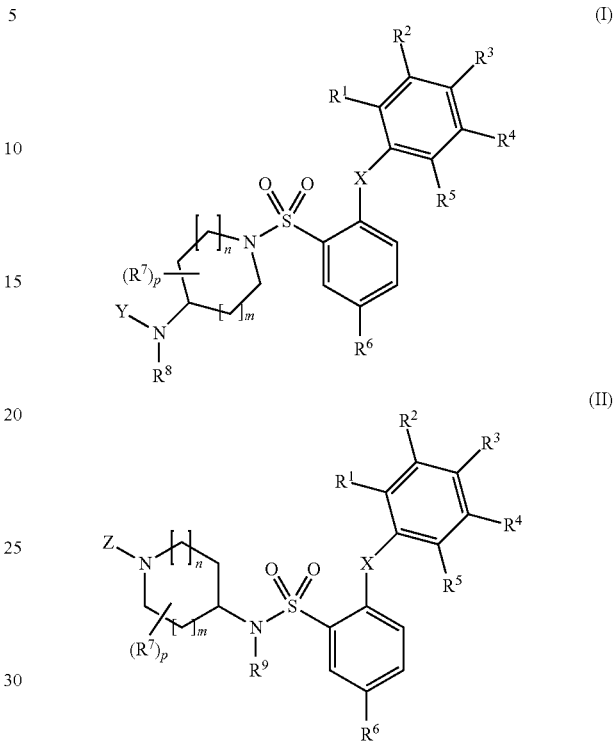

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$, $R^2$, $R^3$, $R^4$, $R^5$, and $R^6$ are each independently (a) hydrogen, deuterium, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^7$ is (a) hydrogen, halo, cyano, nitro, oxo, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, C(N$R^{1a}$)N$R^{1b}R^{1c}$, O$R^{1a}$, OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

X is O or S;

Y is —C(O)$R^{1a}$, —C(S)$R^{1a}$, —C(O)N$R^{1b}R^{1c}$, —C(S)N$R^{1b}R^{1c}$, —C(O)O$R^{1e}$, —S(O)$R^{1a}$ or —S(O)$_2R^{1a}$;

$R^8$ is hydrogen, $C_{1-6}$ alkyl or $C_{3-7}$ cycloalkyl; or

Y and $R^8$ together with the N atom to which they are attached form heteroaryl or heterocyclyl;

Z is —C(O)$R^{1a}$, —C(S)$R^{1a}$, —C(O)N$R^{1b}R^{1c}$, —C(S)N$R^{1b}R^{1c}$, —C(O)O$R^{1e}$, —S(O)$R^{1a}$ or —S(O)$_2R^{1a}$;

m is an integer from 0 to 3;

$R^9$ is hydrogen, $C_{1-6}$ alkyl or $C_{3-7}$ cycloalkyl;

m is an integer from 0 to 3;

n is an integer from 1 to 3;

p is an integer from 1 to 4; and each $R^{1a}$, $R^{1b}$, $R^{1c}$, $R^{1d}$ and $R^{1e}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or each pair of $R^{1b}$ and $R^{1c}$ together with the N atom to which they are attached independently form heteroaryl or heterocyclyl, with the proviso that $R^{1e}$ is not t-butyl or benzyl;

wherein each alkyl, alkenyl, alkynyl, cycloalkyl, aryl, aralkyl, heterocyclyl, and heteroaryl is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents Q; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; or (iii) $R^b$ and $R^c$ together with the N atom to which they are attached form heterocyclyl, optionally substituted with one or more, in one embodiment, one, two, three, or four, substituents Q;

wherein each Q is independently selected from the group consisting of (a) deuterium; (b) cyano, halo, and nitro; (c) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (d) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$;

wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein are arylsulfonamide compounds of Formulae Ia and IIa:

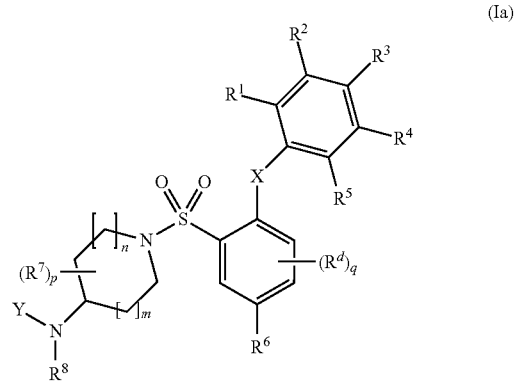

(Ia)

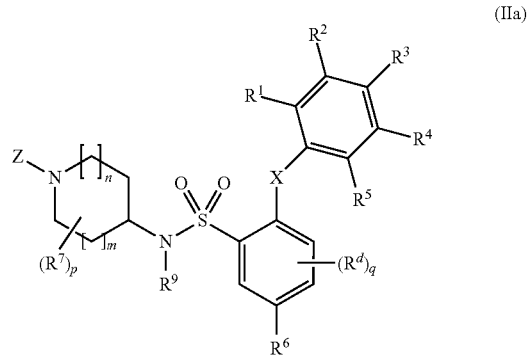

(IIa)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

Wherein $R^1$, $R^2$, $R^3$, $R^4$, $R^5$, $R^6$, $R^7$, $R^8$, $R^9$, $R^{1a}$, $R^{1b}$, $R^{1c}$, $R^{1d}$, $R^{1e}$, X, Y, Z, m, n, and p are as defined herein;

$R^d$ is deuterium; and q is an integer from 0 to 3.

The groups, $R^1$, $R^2$, $R^3$, $R^4$, $R^5$, $R^6$, $R^7$, $R^8$, $R^9$, $R^{1a}$, $R^{1b}$, $R^{1c}$, $R^{1d}$, $R^{1e}$, X, Y, Z, m, n, p and q in Formulae I, II, Ia and IIa are further defined in the embodiments described herein. All combinations of the embodiments provided herein for such groups are within the scope of this disclosure.

In certain embodiments, $R^1$ is hydrogen, deuterium, halo, cyano, nitro, or guanidine. In certain embodiments, $R^1$ is hydrogen. In certain embodiments, $R^1$ is deuterium. In certain embodiments, $R^1$ is halo. In certain embodiments, $R^1$ is fluoro or chloro. In certain embodiments, $R^1$ is $C_{1-6}$ alkyl, optionally substituted as described herein. In certain embodiments, $R^1$ is $C_{1-6}$ alkyl, optionally substituted with one, two, or three halo. In certain embodiments, $R^1$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^1$ is methyl. In certain embodiments, $R^1$ is $C_{1-6}$ alkoxy, optionally substituted as described herein. In certain embodiments, $R^1$ is $C_{1-6}$ alkoxy, optionally substituted with one, two, or three halo. In certain embodiments, $R^1$ is $C_{1-6}$ alkylthio, optionally substituted as described herein. In certain embodiments, $R^1$ is $C_{1-6}$ alkylthio, optionally substituted with one, two, or three halo. In certain embodiments, $R^1$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^1$ is —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein.

In certain embodiments, $R^2$ is hydrogen, deuterium, halo, cyano, nitro, or guanidine. In certain embodiments, $R^2$ is hydrogen. In certain embodiments, $R^2$ is halo. In certain embodiments, $R^2$ is fluoro or chloro. In certain embodiments, $R^2$ is $C_{1-6}$ alkyl, optionally substituted as described herein. In certain embodiments, $R^2$ is $C_{1-6}$ alkyl, optionally substituted with one, two, or three halo. In certain embodiments, $R^2$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^2$ is methyl. In certain embodiments, $R^2$ is $C_{1-6}$ alkoxy, optionally substituted as described herein. In certain embodiments, $R^2$ is $C_{1-6}$ alkoxy, optionally substituted with one, two, or three halo. In certain embodiments, $R^2$ is $C_{1-6}$ alkylthio, optionally substituted as described herein. In certain embodiments, $R^2$ is $C_{1-6}$ alkylthio, optionally substituted with one, two, or three halo. In certain embodiments, $R^2$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^2$ is —C(O)$R^{1a}$, —C(O)O$R^{1a}$, —C(O)N$R^{1b}R^{1c}$; C(N$R^{1a}$)N$R^{1b}R^{1c}$; —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, N$R^{1a}$C(O)$R^{1d}$, N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein.

In certain embodiments, $R^3$ is hydrogen, deuterium, halo, cyano, nitro, or guanidine. In certain embodiments, $R^3$ is hydrogen. In certain embodiments, $R^3$ is halo. In certain embodiments, $R^3$ is fluoro or chloro. In certain embodiments, $R^3$ is $C_{1-6}$ alkyl, optionally substituted as described herein. In certain embodiments, $R^3$ is $C_{1-6}$ alkyl, optionally substituted with one, two, or three halo. In certain embodiments, $R^3$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^3$ is methyl. In certain embodiments, $R^3$ is $C_{1-6}$ alkoxy, optionally substituted as described herein. In certain embodiments, $R^3$ is $C_{1-6}$ alkoxy, optionally substituted with one, two, or three halo. In certain embodiments, $R^3$ is $C_{1-6}$ alkylthio, optionally substituted as described herein. In certain embodiments, $R^3$ is $C_{1-6}$ alkylthio, optionally substituted with one, two, or three halo. In certain embodiments, $R^3$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^3$ is —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$; $R^{1b}$; $R^{1c}$; and $R^{1d}$ are each as defined herein.

In certain embodiments, $R^4$ is hydrogen, deuterium, halo, cyano, nitro, or guanidine. In certain embodiments, $R^4$ is hydrogen. In certain embodiments, $R^4$ is halo. In certain embodiments, $R^4$ is fluoro or chloro. In certain embodiments, $R^4$ is $C_{1-6}$ alkyl, optionally substituted as described herein. In certain embodiments, $R^4$ is $C_{1-6}$ alkyl, optionally substituted with one, two, or three halo. In certain embodiments, $R^4$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^4$ is methyl. In certain embodiments, $R^4$ is $C_{1-6}$ alkoxy, optionally substituted as described herein. In certain embodiments, $R^4$ is $C_{1-6}$ alkoxy, optionally substituted with one, two, or three halo. In certain embodiments, $R^4$ is $C_{1-6}$ alkylthio, optionally substituted as described herein. In certain embodiments, $R^4$ is $C_{1-6}$ alkylthio, optionally substituted with one, two, or three halo. In certain embodiments, $R^4$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^4$ is —C(O)$R^{1a}$, —C(O)O$R^{1a}$, —C(O)N$R^{1b}R^{1c}$; —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$S(O)$_2R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein.

In certain embodiments, $R^5$ is hydrogen, deuterium, cyano, nitro, or guanidine. In certain embodiments, $R^5$ is hydrogen. In certain embodiments, $R^5$ is halo. In certain embodiments, $R^5$ is fluoro or chloro. In certain embodiments, $R^5$ is $C_{1-6}$ alkyl, optionally substituted as described herein. In certain embodiments, $R^5$ is $C_{1-6}$ alkyl, optionally substituted with one, two, or three halo. In certain embodiments, $R^5$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^5$ is methyl. In certain embodiments, $R^5$ is $C_{1-6}$ alkoxy, optionally substituted as described herein. In certain embodiments, $R^5$ is $C_{1-6}$ alkoxy, optionally substituted with one, two, or three halo. In certain embodiments, $R^5$ is $C_{1-6}$ alkylthio, optionally substituted as described herein. In certain embodiments, $R^5$ is $C_{1-6}$ alkylthio, optionally substituted with one, two, or three halo. In certain embodiments, $R^5$ is $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted as described herein. In certain embodiments, $R^5$ is —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, two of R$^1$, R$^2$, R$^3$, R$^4$, and R$^5$ are halo or C$_{1-6}$ alkyl, optionally substituted as described herein. In certain embodiments, two of R$^1$, R$^2$, R$^3$, R$^4$, and R$^5$ are halo or C$_{1-6}$ alkyl, which is optionally substituted as described herein, and the remaining three are hydrogen. In certain embodiments, two of R$^1$, R$^2$, R$^3$, R$^4$, and R$^5$ are chloro or methyl. In certain embodiments, two of R$^1$, R$^2$, R$^3$, R$^4$, and R$^5$ are chloro or methyl, and the remaining three are hydrogen. In certain embodiments, R$^1$, R$^3$, and R$^5$ are hydrogen, and R$^2$ and R$^4$ are halo or C$_{1-6}$ alkyl, optionally substituted as described herein. In certain embodiments, R$^1$, R$^3$, and R$^5$ are hydrogen or deuterium, and R$^2$ and R$^4$ are halo or C$_{1-6}$ alkyl, optionally substituted as described herein. In certain embodiments, R$^1$, R$^3$, and R$^5$ are hydrogen, and R$^2$ and R$^4$ are chloro or methyl. In certain embodiments, R$^1$, R$^3$, and R$^5$ are hydrogen, and R$^2$ and R$^4$ are chloro. In certain embodiments, R$^1$, R$^3$, and R$^5$ are hydrogen, and R$^2$ and R$^4$ are methyl. In certain embodiments, R$^2$, R$^3$, and R$^5$ are hydrogen, and R$^1$ and R$^4$ are halo or C$_{1-6}$ alkyl, optionally substituted as described herein. In certain embodiments, R$^2$, R$^3$, and R$^5$ are hydrogen, and R$^1$ and R$^4$ are chloro or methyl. In certain embodiments, R$^2$, R$^3$, and R$^5$ are hydrogen, and R$^1$ and R$^4$ are chloro. In certain embodiments, R$^2$, R$^3$, and R$^5$ are hydrogen, and R$^1$ and R$^4$ are methyl.

In certain embodiments, R$^6$ is hydrogen, halo, cyano, nitro, or guanidine. In certain embodiments, R$^6$ is hydrogen. In certain embodiments, R$^6$ is halo. In certain embodiments, R$^6$ is fluoro or chloro. In certain embodiments, R$^6$ is cyano. In certain embodiments, R$^6$ is nitro. In certain embodiments, R$^6$ is C$_{1-6}$ alkyl, optionally substituted as described herein. In certain embodiments, R$^6$ is C$_{1-6}$ alkyl, optionally substituted with one, two, or three halo. In certain embodiments, R$^6$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^6$ is methyl. In certain embodiments, R$^6$ is C$_{1-6}$ alkoxy, optionally substituted as described herein. In certain embodiments, R$^6$ is C$_{1-6}$ alkoxy, optionally substituted with one, two, or three halo. In certain embodiments, R$^6$ is C$_{1-6}$ alkylthio, optionally substituted as described herein. In certain embodiments, R$^6$ is C$_{1-6}$ alkylthio, optionally substituted with one, two, or three halo. In certain embodiments, R$^6$ is C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted as described herein. In certain embodiments, R$^6$ is —C(O)R$^{1a}$, —C(O)OR$^{1a}$, —C(O)NR$^{1b}$R$^{1c}$, —C(NR$^{1a}$)NR$^{1b}$R$^{1c}$, OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, R$^7$ is hydrogen, halo, cyano, nitro, oxo, or guanidine. In certain embodiments, R$^7$ is hydrogen. In certain embodiments, R$^7$ is halo. In certain embodiments, R$^7$ is fluoro or chloro. In certain embodiments, R$^7$ is cyano. In certain embodiments, R$^7$ is nitro. In certain embodiments, R$^7$ is oxo. In certain embodiments, R$^7$ is C$_{1-6}$ alkyl, optionally substituted as described herein. In certain embodiments, R$^7$ is C$_{1-6}$ alkyl, optionally substituted with one, two, or three halo. In certain embodiments, R$^7$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^7$ is methyl. In certain embodiments, R$^7$ is C$_{1-6}$ alkoxy, optionally substituted as described herein. In certain embodiments, R$^7$ is C$_{1-6}$ alkoxy, optionally substituted with one, two, or three halo. In certain embodiments, R$^7$ is C$_{1-6}$ alkylthio, optionally substituted as described herein. In certain embodiments, R$^7$ is C$_{1-6}$ alkylthio, optionally substituted with one, two, or three halo. In certain embodiments, R$^7$ is C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted as described herein. In certain embodiments, R$^7$ is —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, S(O)NR$^{1b}$R$^{1c}$, or —S(O)$_2$NR$^{1b}$R$^{1c}$; wherein R$^{1a}$, R$^{1b}$, R$^{1c}$, and R$^{1d}$ are each as defined herein.

In certain embodiments, R$^8$ is hydrogen. In certain embodiments, R$^8$ is C$_{1-6}$ alkyl, optionally substituted as described herein. In certain embodiments, R$^8$ is C$_{1-6}$ alkyl, optionally substituted with one, two, or three halo. In certain embodiments, R$^8$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^8$ is methyl. In certain embodiments, R$^8$ is C$_{3-7}$ cycloalkyl.

In certain embodiments, R$^9$ is hydrogen. In certain embodiments, R$^9$ is C$_{1-6}$ alkyl, optionally substituted as described herein. In certain embodiments, R$^9$ is C$_{1-6}$ alkyl, optionally substituted with one, two, or three halo. In certain embodiments, R$^9$ is methyl, ethyl, propyl (e.g., n-propyl and isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, R$^9$ is methyl. In certain embodiments, R$^9$ is C$_{3-7}$ cycloalkyl.

In certain embodiments, X is O. In certain embodiments, X is S.

In certain embodiments, Y is —C(O)R$^{1a}$, wherein R$^{1a}$ is as defined herein. In certain embodiments, Y is —C(O)—C$_{1-6}$ alkyl. In certain embodiments, Y is —C(O)—C$_{2-6}$ alkenyl. In certain embodiments, Y is —C(O)—C$_{3-7}$ cycloalkyl. In certain embodiments, Y is —C(O)—C$_{6-14}$ aryl. In certain embodiments, Y is —C(O)—C$_{7-15}$ aralkyl. In certain embodiments, Y is —C(S)R$^{1a}$, wherein R$^{1a}$ is as defined herein. In certain embodiments, Y is —C(S)—C$_{1-6}$ alkyl. In certain embodiments, Y is —C(S)—C$_{2-6}$ alkenyl. In certain embodiments, Y is —C(S)—C$_{3-7}$ cycloalkyl. In certain embodiments, Y is —C(S)—C$_{6-14}$ aryl. In certain embodiments, Y is —C(S)—C$_{7-15}$ aralkyl. In certain embodiments, Y is —C(O)NR$^{1b}$R$^{1c}$, wherein R$^{1b}$ and R$^{1c}$ are each as defined herein. In certain embodiments, Y is —C(O)NH—C$_{1-6}$ alkyl. In certain embodiments, Y is —C(O)NH—C$_{1-6}$ alkyl, wherein the C$_{1-6}$ alkyl group is substituted with one, two, or three halo. In certain embodiments, Y is —C(O)NH—C$_{1-6}$ alkyl, wherein the C$_{1-6}$ alkyl group is substituted with heterocyclyl. In one embodiment, Y is —C(O)NH—C$_{1-6}$ alkyl, wherein the C$_{1-6}$ alkyl group is substituted with heterocyclyl, and wherein if the C$_{1-6}$ alkyl group is ethyl, the heterocyclyl is not morpholino. In certain embodiments, Y is —C(O)NH—$C_{2-6}$ alkenyl. In certain embodiments, Y is —C(O)NH—$C_{3-7}$ cycloalkyl. In certain embodiments, Y is —C(O)NH—$C_{6-14}$ aryl. In certain embodiments, Y is —C(O)NH—$C_{7-15}$ aralkyl. In certain embodiments, Y is —C(S)NR$^{1b}$R$^{1c}$, wherein R$^{1b}$ and R$^{1c}$ are each as defined herein. In certain embodiments, Y is —C(S)NH—$C_{1-6}$ alkyl. In certain embodiments, Y is —C(S)NH—$C_{2-6}$ alkenyl. In certain embodiments, Y is —C(S)NH—$C_{3-7}$ cycloalkyl. In certain embodiments, Y is —C(S)NH—$C_{6-14}$ aryl. In certain embodiments, Y is —C(S)NH—$C_{7-15}$ aralkyl. In certain embodiments, Y is —S(O)R$^{1a}$, wherein R$^{1a}$ is as defined herein. In certain embodiments, Y is —S(O)—$C_{1-6}$ alkyl. In certain embodiments, Y is —S(O)—$C_{2-6}$ alkenyl. In certain embodiments, Y is —S(O)—$C_{3-7}$ cycloalkyl. In certain embodiments, Y is —S(O)—$C_{6-14}$ aryl. In certain embodiments, Y is —S(O)—$C_{7-15}$ aralkyl. In certain embodiments, Y is —S(O)$_2$R$^{1a}$, wherein R$^{1a}$ is as defined herein. In certain embodiments, Y is —S(O)$_2$—$C_{1-6}$ alkyl. In certain embodiments, Y is —S(O)$_2$—$C_{2-6}$ alkenyl. In certain embodiments, Y is —S(O)$_2$—$C_{3-7}$ cycloalkyl. In certain embodiments, Y is —S(O)$_2$—$C_{6-14}$ aryl. In certain embodiments, Y is —S(O)$_2$—$C_{7-15}$ aralkyl.

In certain embodiments, Y and R$^8$ together with the N atom to which they are attached form heteroaryl or heterocyclyl. In one embodiment, Y and R$^8$ together with the N atom to which they are attached form heteroaryl. In one embodiment, Y and R$^8$ together with the N atom to which they are attached form heteroaryl, wherein heteroaryl comprises at least one additional O, S, or N atom. In one embodiment, Y and R$^8$ together with the N atom to which they are attached form triazolyl, optionally substituted as described herein. In one embodiment, Y and R$^8$ together with the N atom to which they are attached form heterocyclyl.

In certain embodiments, Z is —C(O)R$^{1a}$, wherein R$^{1a}$ is as defined herein. In certain embodiments, Z is —C(O)—$C_{1-6}$ alkyl. In certain embodiments, Z is —C(O)—$C_{2-6}$ alkenyl. In certain embodiments, Z is —C(O)—$C_{3-7}$ cycloalkyl. In certain embodiments, Z is —C(O)—$C_{6-14}$ aryl. In certain embodiments, Z is —C(O)—$C_{7-15}$ aralkyl. In certain embodiments, Z is —C(S)R$^{1a}$, wherein R$^{1a}$ is as defined herein. In certain embodiments, Z is —C(S)—$C_{1-6}$ alkyl. In certain embodiments, Z is —C(S)—$C_{2-6}$ alkenyl. In certain embodiments, Z is —C(S)—$C_{3-7}$ cycloalkyl. In certain embodiments, Z is —C(S)—$C_{6-14}$ aryl. In certain embodiments, Z is —C(S)—$C_{7-15}$ aralkyl. In certain embodiments, Z is —C(O)NR$^{1b}$R$^{1c}$, wherein R$^{1b}$ and R$^{1c}$ are each as defined herein. In certain embodiments, Z is —C(O)NH—$C_{1-6}$ alkyl. In certain embodiments, Z is —C(O)NH—$C_{2-6}$ alkenyl. In certain embodiments, Z is —C(O)NH—$C_{3-7}$ cycloalkyl. In certain embodiments, Z is —C(O)NH—$C_{6-14}$ aryl. In certain embodiments, Z is —C(O)NH—$C_{7-15}$ aralkyl. In certain embodiments, Z is —C(S)NR$^{1b}$R$^{1c}$, wherein R$^{1b}$ and R$^{1c}$ are each as defined herein. In certain embodiments, Z is —C(S)NH—$C_{1-6}$ alkyl. In certain embodiments, Z is —C(S)NH—$C_{2-6}$ alkenyl. In certain embodiments, Z is —C(S)NH—$C_{3-7}$ cycloalkyl. In certain embodiments, Z is —C(S)NH—$C_{6-14}$ aryl. In certain embodiments, Z is —C(S)NH—$C_{7-15}$ aralkyl. In certain embodiments, Z is —S(O)R$^{1a}$, wherein R$^{1a}$ is as defined herein. In certain embodiments, Z is —S(O)—$C_{1-6}$ alkyl. In certain embodiments, Z is —S(O)—$C_{2-6}$ alkenyl. In certain embodiments, Z is —S(O)—$C_{3-7}$ cycloalkyl. In certain embodiments, Z is —S(O)—$C_{6-14}$ aryl. In certain embodiments, Z is —S(O)—$C_{7-15}$ aralkyl. In certain embodiments, Z is —S(O)$_2$R$^{1a}$, wherein R$^{1a}$ is as defined herein. In certain embodiments, Z is —S(O)$_2$—$C_{1-6}$ alkyl. In certain embodiments, Z is —S(O)$_2$—$C_{2-6}$ alkenyl. In certain embodiments, Z is —S(O)$_2$—$C_{3-7}$ cycloalkyl. In certain embodiments, Z is —S(O)$_2$—$C_{6-14}$ aryl. In certain embodiments, Z is —S(O)$_2$—$C_{7-15}$ aralkyl.

In certain embodiments, m is 0. In certain embodiments, m is 1. In certain embodiments, m is 2. In certain embodiments, m is 3.

In certain embodiments, n is 1. In certain embodiments, n is 2. In certain embodiments, n is 3.

In certain embodiments, m is 1 and n is 1. In certain embodiments, m is 1 and n is 2.

In certain embodiments, p is 1. In certain embodiments, p is 2. In certain embodiments, p is 3. In certain embodiments, p is 4.

In certain embodiments, q is 0. In certain embodiments, q is 1. In certain embodiments, q is 2. In certain embodiments, q is 3.

In certain embodiments, R$^{1a}$ is hydrogen. In certain embodiments, R$^{1a}$ is $C_{1-6}$ alkyl, optionally substituted as described herein. In certain embodiments, R$^{1a}$ is $C_{1-6}$ alkyl, optionally substituted with one or more halo, $C_{1-6}$ alkoxy, $C_{1-6}$ alkylthio, heterocyclyl or heteroaryl. In certain embodiments, R$^{1a}$ is methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylbutyl, 1,2-dimethylpropyl, or 2,2-dimethylpropyl). In certain embodiments, R$^{1a}$ is methyl, ethyl, isopropyl, isobutyl, t-butyl, 1,1-dimethylpropyl, or 2,2-dimethylpropyl. In certain embodiments, R$^{1a}$ is $C_{2-6}$ alkenyl, optionally substituted as described herein. In certain embodiments, R$^{1a}$ is $C_{2-6}$ alkynyl, optionally substituted as described herein. In certain embodiments, R$^{1a}$ is $C_{3-7}$ cycloalkyl, optionally substituted as described herein. In certain embodiments, R$^{1a}$ is $C_{3-7}$ cycloalkyl, optionally substituted with one or two $C_{1-6}$ alkyl. In certain embodiments, R$^{1a}$ is $C_{3-7}$ cycloalkyl, optionally substituted with two methyl groups. In certain embodiments, R$^{1a}$ is cyclobutyl, cyclopentyl, cyclohexyl, or dimethylbicyclo-[2.2.1]heptyl (e.g., 7,7-dimethylbicyclo[2.2.1]-heptyl). In certain embodiments, R$^{1a}$ is cyclobutyl, cyclopentyl, cyclohexyl, or (1S,2S,4R)-7,7-dimethylbicyclo[2.2.1]-heptyl. In certain embodiments, R$^{1a}$ is $C_{6-14}$ aryl, optionally substituted as described herein. In certain embodiments, R$^{1a}$ is $C_{6-14}$ aryl, optionally substituted with one or more halo or $C_{1-6}$ alkyl, wherein the alkyl is optionally substituted with one, two, or three halo. In certain embodiments, R$^{1a}$ is $C_{6-14}$ aryl, optionally substituted with fluoro, chloro, methyl, trifluoromethyl, or ethyl. In certain embodiments, R$^{1a}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, R$^{1a}$ is phenyl, 3-fluorophenyl, 3-methylphenyl, 4-chlorophenyl, 4-methylphenyl, 4-trifluoromethylphenyl, or 4-ethylphenyl. In certain embodiments, R$^{1a}$ is heteroaryl, optionally substituted as described herein. In certain embodiments, R$^{1a}$ is heterocyclyl.

In certain embodiments, R$^{1b}$ is hydrogen. In certain embodiments, R$^{1b}$ is $C_{1-6}$ alkyl, optionally substituted as described herein. In certain embodiments, R$^{1b}$ is $C_{1-6}$ alkyl, optionally substituted with one or more halo, $C_{1-6}$ alkoxy, $C_{1-6}$ alkylthio, heterocyclyl or heteroaryl. In certain embodiments, R$^{1b}$ is $C_{2-6}$ alkenyl, optionally substituted as described herein. In certain embodiments, R$^{1b}$ is $C_{2-6}$ alkynyl, optionally substituted as described herein. In certain embodiments, R$^{1b}$ is $C_{3-7}$ cycloalkyl, optionally substituted as described herein. In certain embodiments, $R^{1b}$ is $C_{6-14}$ aryl, optionally substituted as described herein. In certain embodiments, $R^{1b}$ is heteroaryl, optionally substituted as described herein. In certain embodiments, $R^{1b}$ is heterocyclyl, optionally substituted as described herein.

In certain embodiments, $R^{1c}$ is hydrogen. In certain embodiments, $R^{1c}$ is $C_{1-6}$ alkyl, optionally substituted as described herein. In certain embodiments, $R^{1c}$ is $C_{1-6}$ alkyl, optionally substituted with one or more halo, $C_{1-6}$ alkoxy, $C_{1-6}$ alkylthio, heterocyclyl or heteroaryl. In certain embodiments, $R^{1c}$ is methyl, ethyl, propyl (e.g., n-propyl or isopropyl), butyl (e.g., n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1c}$ is methyl, ethyl, isopropyl, isobutyl, t-butyl, 1,1-dimethylpropyl, or 2,2-dimethylpropyl. In certain embodiments, $R^{1c}$ is $C_{2-6}$ alkenyl, optionally substituted as described herein. In certain embodiments, $R^{1c}$ is $C_{2-6}$ alkynyl, optionally substituted as described herein. In certain embodiments, $R^{1c}$ is $C_{3-7}$ cycloalkyl, optionally substituted as described herein. In certain embodiments, $R^{1c}$ is $C_{3-7}$ cycloalkyl, optionally substituted with one or two $C_{1-6}$ alkyl. In certain embodiments, $R^{1c}$ is $C_{3-7}$ cycloalkyl, optionally substituted with two methyl groups. In certain embodiments, $R^{1c}$ is cyclobutyl, cyclopentyl, cyclohexyl, or dimethylbicyclo-[2.2.1]heptyl (e.g., 7,7-dimethylbicyclo[2.2.1]-heptyl). In certain embodiments, $R^{1c}$ is cyclobutyl, cyclopentyl, cyclohexyl, or (1S,2S,4R)-7,7-dimethylbicyclo[2.2.1]-heptyl. In certain embodiments, $R^{1c}$ is $C_{6-14}$ aryl, optionally substituted as described herein. In certain embodiments, $R^{1c}$ is $C_{6-14}$ aryl, optionally substituted with one or more halo or $C_{1-6}$ alkyl, wherein the alkyl is optionally substituted with one, two, or three halo. In certain embodiments, $R^{1c}$ is $C_{6-14}$ aryl, optionally substituted with fluoro, chloro, methyl, trifluoromethyl, or ethyl. In certain embodiments, $R^{1c}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, $R^{1c}$ is phenyl, 3-fluorophenyl, 3-methylphenyl, 4-chlorophenyl, 4-methylphenyl, 4-trifluoromethylphenyl, or 4-ethylphenyl. In certain embodiments, $R^{1c}$ is heteroaryl, optionally substituted as described herein. In certain embodiments, $R^{1c}$ is heterocyclyl.

In certain embodiments, $R^{1b}$ and $R^{1c}$ together with the N atom to which they are attached independently form heteroaryl, optionally substituted as described herein. In certain embodiments, $R^{1b}$ and $R^{1c}$ together with the N atom to which they are attached independently form heterocyclyl, optionally substituted as described herein.

In certain embodiments, $R^{1d}$ is hydrogen. In certain embodiments, $R^{1d}$ is $C_{1-6}$ alkyl, optionally substituted as described herein. In certain embodiments, $R^{1d}$ is $C_{2-6}$ alkenyl, optionally substituted as described herein. In certain embodiments, $R^{1d}$ is $C_{2-6}$ alkynyl, optionally substituted as described herein. In certain embodiments, $R^{1d}$ is $C_{3-7}$ cycloalkyl, optionally substituted as described herein. In certain embodiments, $R^{1d}$ is $C_{6-14}$ aryl, optionally substituted as described herein. In certain embodiments, $R^{1d}$ is heteroaryl, optionally substituted as described herein. In certain embodiments, $R^{1d}$ is heterocyclyl, optionally substituted as described herein.

In certain embodiments, $R^{1e}$ is hydrogen. In certain embodiments, $R^{1e}$ is $C_{1-6}$ alkyl, optionally substituted as described herein, with the proviso that $R^{1e}$ is not t-butyl. In certain embodiments, $R^{1e}$ is $C_{1-6}$ alkyl, optionally substituted with one or more halo, $C_{1-6}$ alkoxy, $C_{1-6}$ alkylthio, heterocyclyl or heteroaryl. In certain embodiments, $R^{1e}$ is methyl, ethyl, propyl (e.g., n-propyl or isopropyl), n-butyl, 2-butyl, isobutyl, or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1e}$ is methyl, ethyl, isopropyl, isobutyl, 1,1-dimethylpropyl, or 2,2-dimethylpropyl. In certain embodiments, $R^{1e}$ is $C_{2-6}$ alkenyl, optionally substituted as described herein. In certain embodiments, $R^{1e}$ is $C_{2-6}$ alkynyl, optionally substituted as described herein. In certain embodiments, $R^{1e}$ is $C_{3-7}$ cycloalkyl, optionally substituted as described herein. In certain embodiments, $R^{1e}$ is $C_{3-7}$ cycloalkyl, optionally substituted with one or two $C_{1-6}$ alkyl. In certain embodiments, $R^{1e}$ is $C_{3-7}$ cycloalkyl, optionally substituted with two methyl groups. In certain embodiments, $R^{1e}$ is cyclobutyl, cyclopentyl, cyclohexyl, or dimethylbicyclo-[2.2.1]heptyl (e.g., 7,7-dimethylbicyclo[2.2.1]-heptyl). In certain embodiments, $R^{1e}$ is cyclobutyl, cyclopentyl, cyclohexyl, or (1S,2S,4R)-7,7-dimethylbicyclo[2.2.1]-heptyl. In certain embodiments, $R^{1e}$ is $C_{6-14}$ aryl, optionally substituted as described herein. In certain embodiments, $R^{1e}$ is $C_{6-14}$ aryl, optionally substituted with one or more halo or $C_{1-6}$ alkyl, wherein the alkyl is optionally substituted with one, two, or three halo. In certain embodiments, $R^{1e}$ is $C_{6-14}$ aryl, optionally substituted with fluoro, chloro, methyl, trifluoromethyl, or ethyl. In certain embodiments, $R^{1e}$ is phenyl, fluorophenyl (e.g., 2-fluorophenyl, 3-fluorophenyl, or 4-fluorophenyl), chlorophenyl (e.g., 2-chlorophenyl, 3-chlorophenyl, or 4-chlorophenyl), methylphenyl (e.g., 2-methylphenyl, 3-methylphenyl, or 4-methylphenyl), trifluoromethylphenyl (e.g., 2-trifluoromethylphenyl, 3-trifluoromethylphenyl, or 4-trifluoromethylphenyl), or ethylphenyl (e.g., 2-ethylphenyl, 3-ethylphenyl, or 4-ethylphenyl). In certain embodiments, $R^{1e}$ is phenyl, 3-fluorophenyl, 3-methylphenyl, 4-chlorophenyl, 4-methylphenyl, 4-trifluoromethylphenyl, or 4-ethylphenyl. In certain embodiments, $R^{1e}$ is heteroaryl, optionally substituted as described herein. In certain embodiments, $R^{1e}$ is heterocyclyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen or $C_{1-6}$ alkyl;

$R^8$ is hydrogen or $C_{1-6}$ alkyl;

X is O or S;

m is 0, 1, or 2;

n is 1 or 2;

p is 1, 2, 3, or 4; and

Y is —C(O)$R^{1a}$, —C(S)$R^{1a}$, —C(O)NR$^{1b}$R$^{1c}$, —C(S)NR$^{1b}$R$^{1c}$, —C(O)OR$^{1e}$, —S(O)$R^{1a}$ or —S(O)$_2$R$^{1a}$; wherein $R^{1a}$, $R^{1c}$ and $R^{1e}$ are each independently (a) $C_{1-6}$ alkyl, optionally substituted with one or more halo, $C_{1-6}$ alkoxy, $C_{1-6}$ alkylthio, heterocyclyl or heteroaryl; (b) $C_{2-6}$ alkenyl, optionally substituted with one or more halo; (c) $C_{3-7}$ cycloalkyl, optionally substituted with one or more halo, or one or two $C_{1-6}$ alkyl; (d) $C_{6-14}$ aryl, optionally substituted with one or more halo, $C_{1-6}$ alkyl, where the alkyl is further optionally substituted with one, two, or three halo or $C_{1-6}$ alkoxy, where the alkoxy is further optionally substituted with one, two, or three halo; (e) heteroaryl, optionally substituted with one or two $C_{1-6}$ alkyl; or (f) $C_{7-15}$ aralkyl optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; and $R^{1b}$ is hydrogen or methyl; or $R^{1b}$ and $R^{1c}$ together with the N atom to which they are attached form heterocyclyl;

with the proviso that $R^{1e}$ is not t-butyl or benzyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

$R^8$ is hydrogen or $C_{1-6}$ alkyl;

X is O or S;

m is 1;

n is 1;

p is 1, 2, 3, or 4; and

Y is —C(O)$R^{1a}$, —C(S)$R^{1a}$, —C(O)NR$^{1b}$R$^{1c}$, —C(S)NR$^{1b}$R$^{1c}$, —S(O)$R^{1a}$ or —S(O)$_2$R$^{1a}$; wherein $R^{1a}$ and $R^{1c}$ are each independently (a) $C_{1-6}$ alkyl, optionally substituted with one or more halo, $C_{1-6}$ alkoxy, $C_{1-6}$ alkylthio, heterocyclyl or heteroaryl; (b) $C_{2-6}$ alkenyl, optionally substituted with one or more halo; (c) $C_{3-7}$ cycloalkyl, optionally substituted with one or more halo, or one or two $C_{1-6}$ alkyl; (d) $C_{6-14}$ aryl, optionally substituted with one or more halo, $C_{1-6}$ alkyl, where the alkyl is further optionally substituted with one, two, or three halo or $C_{1-6}$ alkoxy, where the alkoxy is further optionally substituted with one, two, or three halo; (e) heteroaryl, optionally substituted with one or two $C_{1-6}$ alkyl; or (f) $C_{7-15}$ aralkyl optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; and $R^{1b}$ is hydrogen or methyl; or $R^{1b}$ and $R^{1c}$ together with the N atom to which they are attached form heterocyclyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

$R^8$ is hydrogen or methyl;

X is O or S;

m is 1;

n is 1;

p is 1, 2, 3, or 4; and

Y is —C(O)$R^{1a}$ or —C(S)$R^{1a}$; wherein $R^{1a}$ is (a) $C_{1-6}$ alkyl, optionally substituted with one or more halo; (b) $C_{2-6}$ alkenyl; (c) $C_{3-7}$ cycloalkyl; or (d) $C_{6-14}$ aryl, optionally substituted with one or more halo, $C_{1-6}$ alkyl or $C_{1-6}$ alkoxy.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

$R^8$ is hydrogen or methyl;

X is O or S;

m is 1;

n is 1;

p is 1, 2, 3, or 4; and

Y is —C(O)NR$^{1b}$R$^{1c}$ or —C(S)NR$^{1b}$R$^{1c}$; wherein $R^{1b}$ is hydrogen; and $R^{1c}$ is (a) $C_{1-6}$ alkyl, optionally substituted with one or more halo or $C_{1-6}$ alkoxy, $C_{1-6}$ alkylthio, heterocyclyl or heteroaryl; (b) $C_{2-6}$ alkenyl; (c) $C_{3-7}$ cycloalkyl; or (d) $C_{6-14}$ aryl, optionally substituted with one or more halo, $C_{1-6}$ alkyl or $C_{1-6}$ alkoxy; and $R^{1b}$ is hydrogen or methyl; or $R^{1b}$ and $R^{1c}$ together with the N atom to which they are attached form heterocyclyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

$R^8$ is hydrogen or methyl;

X is O or S;

m is 1;

n is 1;

p is 1; and

Y is —C(O)NR$^{1b}$R$^{1c}$ or —C(S)NR$^{1b}$R$^{1c}$; wherein $R^{1b}$ is hydrogen; and $R^{1c}$ is $C_{1-6}$ alkyl optionally substituted with (a) one or more halo; or (b) heterocyclyl; and $R^{1b}$ is hydrogen or methyl.

In one embodiment, in Formula I, $R^1$ is hydrogen;

$R^2$ is chloro;

$R^3$ is hydrogen;

$R^4$ is chloro;

$R^5$ is hydrogen;

$R^6$ is cyano;

$R^7$ is hydrogen;

X is O or S;

m is 1;

n is 1;

p is 1, 2, 3, or 4;

Y is —C(O)NR$^{1b}$R$^{1c}$ or —C(S)NR$^{1b}$R$^{1c}$; wherein $R^{1b}$ is hydrogen;

$R^{1c}$ is $C_{1-6}$ alkyl optionally substituted with (a) one or more halo; or (b) heterocyclyl; and $R^{1b}$ is hydrogen or methyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

$R^8$ is hydrogen or methyl;

X is O or S;

m is 1;

n is 1;

p is 1, 2, 3, or 4; and

Y is —S(O)$_2$R$^{1a}$; wherein $R^{1a}$ is (a) $C_{1-6}$ alkyl; (b) $C_{6-14}$ aryl, optionally substituted with one or more halo, $C_{1-6}$ alkyl or $C_{1-6}$ alkoxy; or (c) heteroaryl, optionally substituted with one or two $C_{1-6}$ alkyl.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

X is O or S;

m is 1;

n is 1;

p is 1, 2, 3, or 4; and

Y and $R^8$ together with the N atom to which they are attached form heteroaryl, wherein the heteroaryl comprises at least one additional O, S, or N atom, optionally substituted with one or two $C_{1-6}$ alkyl groups.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

X is O or S;

m is 1;

n is 1;

p is 1, 2, 3, or 4; and

Y and $R^8$ together with the N atom to which they are attached form a 5 membered heteroaryl, wherein the heteroaryl comprises at least one additional O, S, or N atom, optionally substituted with one or two $C_{1-6}$ alkyl groups.

In one embodiment, in Formula I, $R^1$, $R^2$, $R^3$, $R^4$, and $R^5$ are each independently hydrogen, halo, or $C_{1-6}$ alkyl;

$R^6$ is cyano or nitro;

$R^7$ is hydrogen;

X is O or S;

m is 1;

n is 1;

p is 1, 2, 3, or 4; and

Y and $R^8$ together with the N atom to which they are attached form triazolyl, optionally substituted with one or two methyl groups.

In another embodiment, in Formula I, $R^1$ is hydrogen;

$R^2$ is chloro or methyl;

$R^3$ is hydrogen;

$R^4$ is chloro or methyl;

$R^5$ is hydrogen;

$R^6$ is cyano;

$R^7$ is hydrogen;

X is O or S;

m is 1;

n is 1;

p is 1, 2, 3, or 4; and

Y and $R^8$ are as defined elsewhere herein.

In one embodiment, in Formula Ia, $R^1$, $R^2$, $R^3$, $R^4$, and $R^5$ are each independently hydrogen, deuterium, halo, or $C_{1-6}$ alkyl;

$R^6$ is cyano or nitro;

$R^8$ is hydrogen;

$R^d$ is deuterium;

X is O or S;

m is 0, 1, or 2;

n is 1 or 2;

p is 1, 2, 3, or 4;

q is 3; and

Y is —C(O)$R^{1a}$, —C(S)$R^{1a}$, —C(O)N$R^{1b}R^{1c}$, —C(S)N$R^{1b}R^{1c}$, —C(O)O$R^{1e}$, —S(O)$R^{1a}$ or —S(O)$_2R^{1a}$; wherein $R^{1a}$, $R^{1c}$ and $R^{1e}$ are each independently (a) $C_{1-6}$ alkyl, optionally substituted with one or more halo, $C_{1-6}$ alkoxy, $C_{1-6}$ alkylthio, heterocyclyl or heteroaryl; (b) $C_{2-6}$ alkenyl, optionally substituted with one or more halo; (c) $C_{3-7}$ cycloalkyl, optionally substituted with one or more halo, or one or two $C_{1-6}$ alkyl; (d) $C_{6-14}$ aryl, optionally substituted with one or more halo, $C_{1-6}$ alkyl, where the alkyl is further optionally substituted with one, two, or three halo or $C_{1-6}$ alkoxy, where the alkoxy is further optionally substituted with one, two, or three halo; (e) heteroaryl, optionally substituted with one or two $C_{1-6}$ alkyl; or (f) $C_{7-15}$ aralkyl optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; and $R^{1b}$ is hydrogen or methyl; or $R^{1b}$ and $R^{1c}$ together with the N atom to which they are attached form heterocyclyl.

In another embodiment, in Formula Ia, $R^1$, $R^2$, $R^3$, $R^4$, and $R^5$ are each independently hydrogen, deuterium, halo, or $C_{1-6}$ alkyl;

$R^6$ is cyano;

$R^8$ is hydrogen;

$R^d$ is deuterium;

X is O or S;

m is 1;

n is 1;

p is 4;

q is 3; and

Y is —C(O)$R^{1a}$, c(s)$R^{1a}$, C(O)N$R^{1b}R^{1c}$, —C(S)N$R^{1b}R^{1c}$, —C(O)O$R^{1e}$, —S(O)$R^{1a}$ or —S(O)$_2R^{1a}$; wherein $R^{1a}$, $R^{1c}$ and $R^{1e}$ are each independently (a) $C_{1-6}$ alkyl, optionally substituted with one or more halo, $C_{1-6}$ alkoxy, $C_{1-6}$ alkylthio, heterocyclyl or heteroaryl; (b) $C_{2-6}$ alkenyl, optionally substituted with one or more halo; (c) $C_{3-7}$ cycloalkyl, optionally substituted with one or more halo, or one or two $C_{1-6}$ alkyl; (d) $C_{6-14}$ aryl, optionally substituted with one or more halo, $C_{1-6}$ alkyl, where the alkyl is further optionally substituted with one, two, or three halo or $C_{1-6}$ alkoxy, where the alkoxy is further optionally substituted with one, two, or three halo; (e) heteroaryl, optionally substituted with one or two $C_{1-6}$ alkyl; or (f) $C_{7-15}$ aralkyl optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; and $R^{1b}$ is hydrogen or methyl; or $R^{1b}$ and $R^{1c}$ together with the N atom to which they are attached form heterocyclyl.

In another embodiment, in Formula Ia, $R^1$, $R^2$, $R^3$, $R^4$, and $R^5$ are each independently hydrogen, deuterium, halo, or $C_{1-6}$ alkyl;

$R^6$ is cyano;

$R^8$ is hydrogen;

$R^d$ is deuterium;

X is O or S;

m is 1;

n is 1;

p is 4;

q is 3; and

Y is —C(O)N$R^{1b}R^{1c}$; wherein $R^{1c}$ is (a) $C_{1-6}$ alkyl, optionally substituted with one or more halo, $C_{1-6}$ alkoxy, $C_{1-6}$ alkylthio, heterocyclyl or heteroaryl; (b) $C_{2-6}$ alkenyl, optionally substituted with one or more halo; (c) $C_{3-7}$ cycloalkyl, optionally substituted with one or more halo, or one or two $C_{1-6}$ alkyl; (d) $C_{6-14}$ aryl, optionally substituted with one or more halo, $C_{1-6}$ alkyl, where the alkyl is further optionally substituted with one, two, or three halo or $C_{1-6}$ alkoxy, where the alkoxy is further optionally substituted with one, two, or three halo; (e) heteroaryl, optionally substituted with one or two $C_{1-6}$ alkyl; or (f) $C_{7-15}$ aralkyl optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; and $R^{1b}$ is hydrogen.

In another embodiment, in Formula Ia, $R^1$, $R^2$, $R^3$, $R^4$, and $R^5$ are each independently hydrogen, halo, or $C_{1-6}$ alkyl;

$R^6$ is cyano;

$R^8$ is hydrogen;

$R^d$ is deuterium;
X is O or S;
m is 1;
n is 1;
p is 4;
q is 3; and
Y is —C(O)NR$^{1b}$R$^{1c}$; wherein
R$^{1c}$ is (a) C$_{1-6}$ alkyl substituted with heterocyclyl; or (b) C$_{2-6}$ alkenyl; and
R$^{1b}$ is hydrogen.

In one embodiment, in Formula II,
R$^1$, R$^2$, R$^3$, R$^4$, and R$^5$ are each independently hydrogen, halo, or C$_{1-6}$ alkyl;
R$^6$ is cyano or nitro;
R$^7$ is hydrogen or C$_{1-6}$ alkyl;
R$^9$ is hydrogen or C$_{1-6}$ alkyl;
X is O or S;
m is 0, 1, or 2;
n is 1 or 2;
p is 1, 2, 3, or 4; and
Z is —C(O)R$^{1a}$, —C(S)R$^{1a}$, —C(O)NR$^{1b}$R$^{1c}$, C(S)NR$^{1b}$R$^{1c}$, —C(O)OR$^{1e}$, —S(O)R$^{1a}$ or —S(O)$_2$R$^{1a}$; wherein
R$^{1a}$, R$^{1c}$ and R$^{1e}$ are each independently (a) C$_{1-6}$ alkyl, optionally substituted with one or more halo, C$_{1-6}$ alkoxy, C$_{1-6}$ alkylthio, heterocyclyl or heteroaryl; (b) C$_{2-6}$ alkenyl, optionally substituted with one or more halo; (c) C$_{3-7}$ cycloalkyl, optionally substituted with one or more halo, or one or two C$_{1-6}$ alkyl; (d) C$_{6-14}$ aryl, optionally substituted with one or more halo, C$_{1-6}$ alkyl, where the alkyl is further optionally substituted with one, two, or three halo or C$_{1-6}$ alkoxy, where the alkoxy is further optionally substituted with one, two, or three halo; (e) heteroaryl, optionally substituted with one or two C$_{1-6}$ alkyl; or (f) C$_{7-15}$ aralkyl optionally substituted with one or more halo, C$_{1-6}$ alkyl, where the alkyl is further optionally substituted with one, two, or three halo, or C$_{1-6}$ alkoxy, where the alkoxy is further optionally substituted with one, two, or three halo; and
R$^{1b}$ is hydrogen or methyl; or
R$^{1b}$ and R$^{1c}$ together with the N atom to which they are attached form heterocyclyl;
with the proviso that R$^{1e}$ is not t-butyl or benzyl.

In one embodiment, in Formula II,
R$^1$, R$^2$, R$^3$, R$^4$, and R$^5$ are each independently hydrogen, halo, or C$_{1-6}$ alkyl;
R$^6$ is cyano or nitro;
R$^7$ is hydrogen;
R$^9$ is hydrogen or methyl;
X is O or S;
m is 1;
n is 1;
p is 1, 2, 3, or 4; and
Z is —C(O)R$^{1a}$ or —C(S)R$^{1a}$; wherein
R$^{1a}$ is (a) C$_{1-6}$ alkyl, optionally substituted with one or more halo; (b) C$_{2-6}$ alkenyl; (c) C$_{3-7}$ cycloalkyl; or (d) C$_{6-14}$ aryl, optionally substituted with one or more halo, C$_{1-6}$ alkyl or C$_{1-6}$ alkoxy.

In one embodiment, in Formula II,
R$^1$, R$^2$, R$^3$, R$^4$, and R$^5$ are each independently hydrogen, halo, or C$_{1-6}$ alkyl;
R$^6$ is cyano or nitro;
R$^7$ is hydrogen;
R$^9$ is hydrogen or methyl;
X is O or S;
m is 1;
n is 1;
p is 1, 2, 3, or 4; and
Z is —C(O)NR$^{1b}$R$^{1c}$ or —C(S)NR$^{1b}$R$^{1c}$; wherein
R$^{1b}$ is hydrogen; and
R$^{1c}$ is (a) C$_{1-6}$ alkyl, optionally substituted with one or more halo or C$_{1-6}$ alkoxy, C$_{1-6}$ alkylthio, heterocyclyl or heteroaryl; (b) C$_{2-6}$ alkenyl; (c) C$_{3-7}$ cycloalkyl; or (d) C$_{6-14}$ aryl, optionally substituted with one or more halo, C$_{1-6}$ alkyl or C$_{1-6}$ alkoxy; and
R$^{1b}$ is hydrogen or methyl; or
R$^{1b}$ and R$^{1c}$ together with the N atom to which they are attached form heterocyclyl.

In one embodiment, in Formula II,
R$^1$, R$^2$, R$^3$, R$^4$, and R$^5$ are each independently hydrogen, halo, or C$_{1-6}$ alkyl;
R$^6$ is cyano or nitro;
R$^7$ is hydrogen;
R$^9$ is hydrogen or methyl;
X is O or S;
m is 1;
n is 1;
p is 1, 2, 3, or 4; and
Z is —S(O)$_2$R$^{1a}$; wherein
R$^{1a}$ is (a) C$_{1-6}$ alkyl; (b) C$_{6-14}$ aryl, optionally substituted with one or more halo, C$_{1-6}$ alkyl or C$_{1-6}$ alkoxy; or (c) heteroaryl, optionally substituted with one or two C$_{1-6}$ alkyl.

In another embodiment, in Formula II,
R$^1$ is hydrogen;
R$^2$ is chloro or methyl;
R$^3$ is hydrogen;
R$^4$ is chloro or methyl;
R$^5$ is hydrogen;
R$^6$ is cyano;
R$^7$ is hydrogen;
X is O or S;
m is 1;
n is 1;
p is 1, 2, 3, or 4; and
Z and R$^9$ are as defined elsewhere herein.

In one embodiment, in Formula IIa,
R$^1$, R$^2$, R$^3$, R$^4$, and R$^5$ are each independently hydrogen, deuterium, halo, or C$_{1-6}$ alkyl;
R$^6$ is cyano or nitro;
R$^7$ is hydrogen or C$_{1-6}$ alkyl;
R$^9$ is hydrogen or C$_{1-6}$ alkyl;
R$^d$ is deuterium;
X is O or S;
m is 0, 1, or 2;
n is 1 or 2;
p is 1, 2, 3, or 4; and
q is 3; and
Z is —C(O)R$^{1a}$, —C(S)R$^{1a}$, —C(O)NR$^{1b}$R$^{1c}$, C(S)NR$^{1b}$R$^{1c}$, C(O)OR$^{1e}$, —S(O)R$^{1a}$ or —S(O)$_2$R$^{1a}$; wherein
R$^{1a}$, R$^{1c}$ and R$^{1e}$ are each independently (a) C$_{1-6}$ alkyl, optionally substituted with one or more halo, C$_{1-6}$ alkoxy, C$_{1-6}$ alkylthio, heterocyclyl or heteroaryl; (b) C$_{2-6}$ alkenyl, optionally substituted with one or more halo; (c) C$_{3-7}$ cycloalkyl, optionally substituted with one or more halo, or one or two C$_{1-6}$ alkyl; (d) C$_{6-14}$ aryl, optionally substituted with one or more halo, C$_{1-6}$ alkyl, where the alkyl is further optionally substituted with one, two, or three halo or C$_{1-6}$ alkoxy, where the alkoxy is further optionally substituted with one, two, or three halo; (e) heteroaryl, optionally substituted with one or two C$_{1-6}$ alkyl; or (f) C$_{7-15}$ aralkyl optionally substituted with one or more halo, C$_{1-6}$ alkyl, where the alkyl is further optionally substituted with one, two, or three halo, or C$_{1-6}$ alkoxy, where the alkoxy is further optionally substituted with one, two, or three halo; and $R^{1b}$ is hydrogen or methyl; or
$R^{1b}$ and $R^{1c}$ together with the N atom to which they are attached form heterocyclyl.
In one embodiment, provided herein is a compound selected from the group consisting of:
1
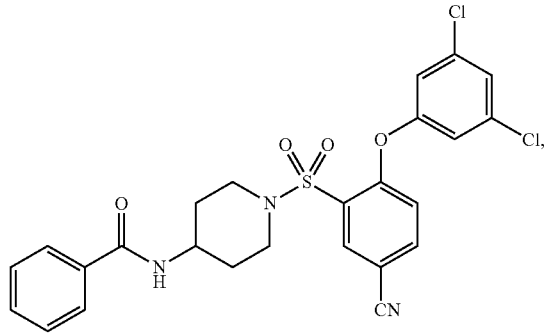
2
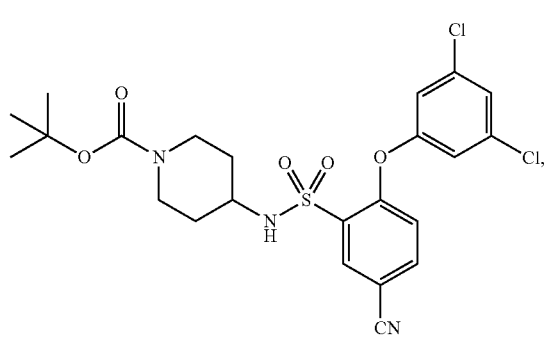
3
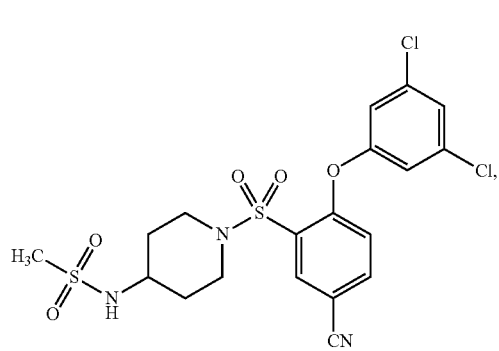
4
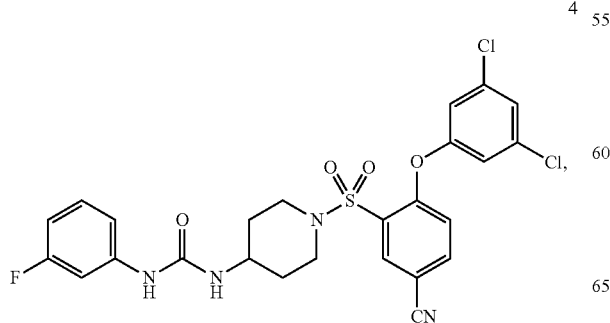
-continued
5
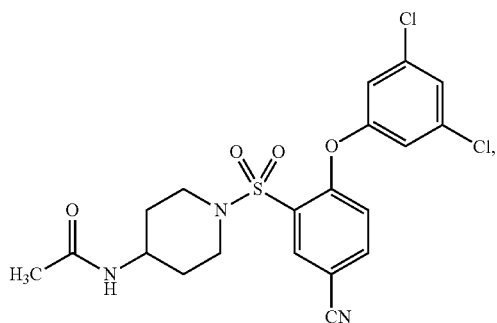
6
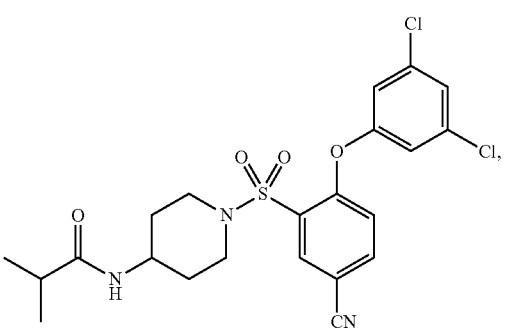
7
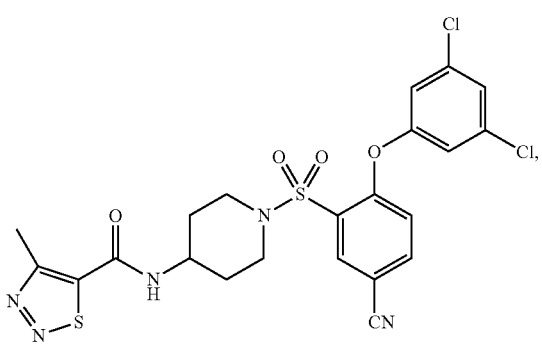
8
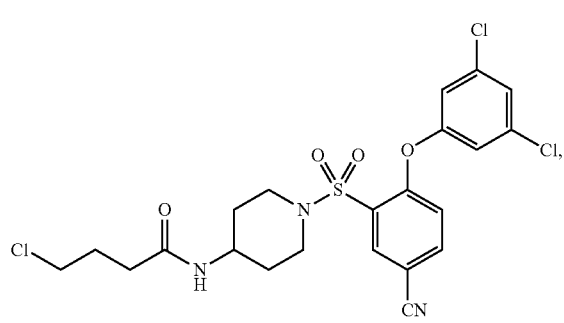

9
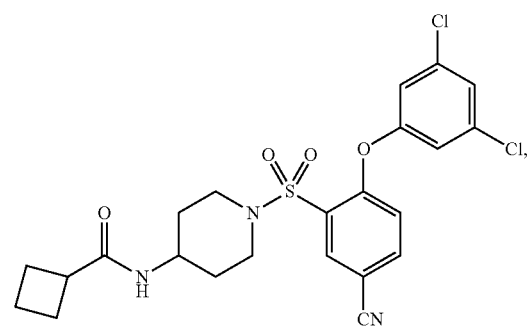
10
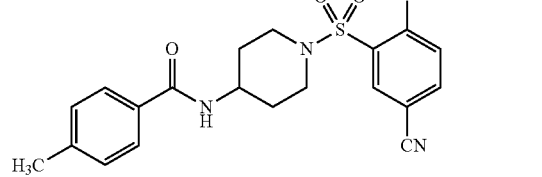
11
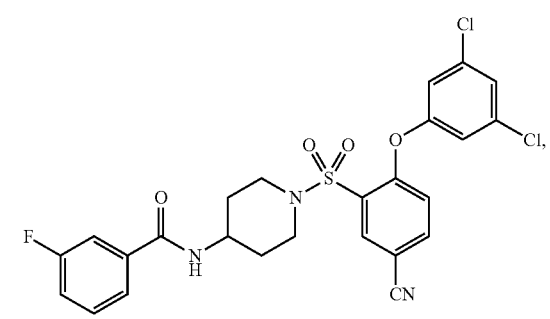
12
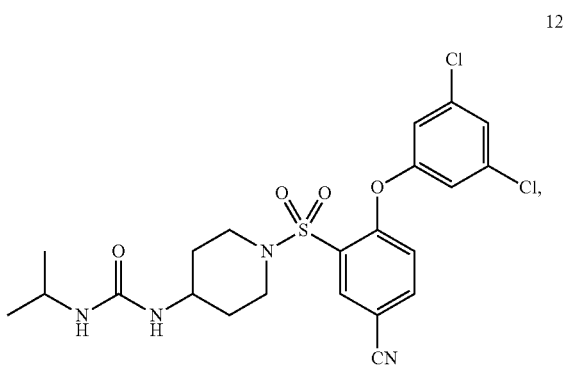
13
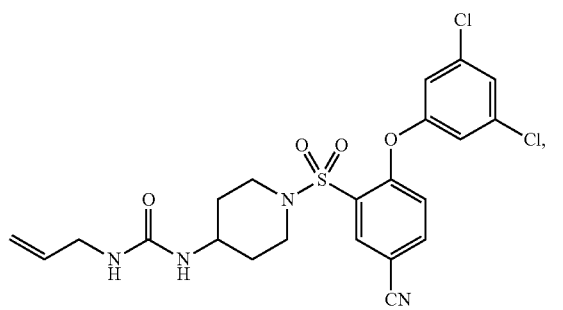
14
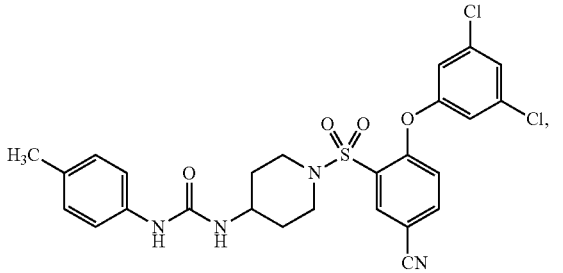
15
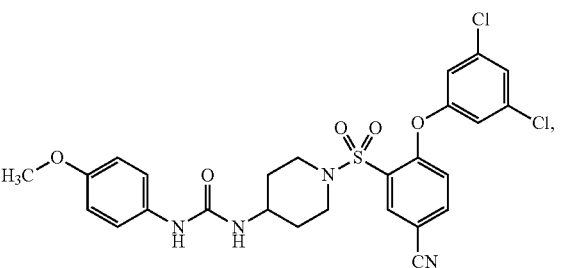
16
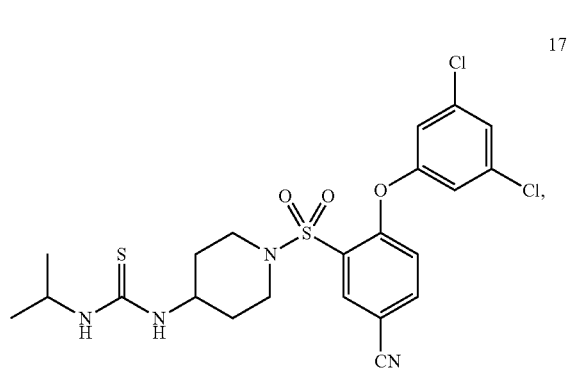
17

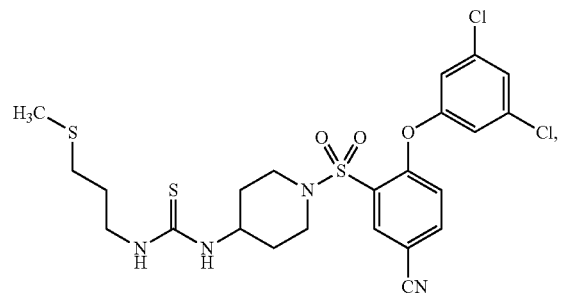
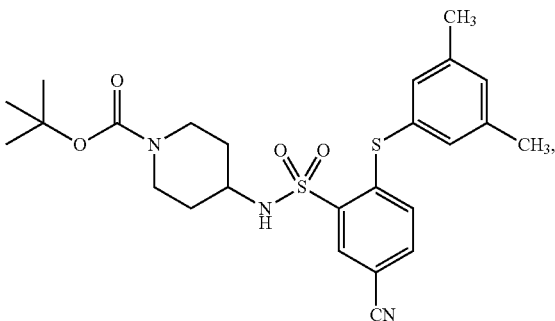
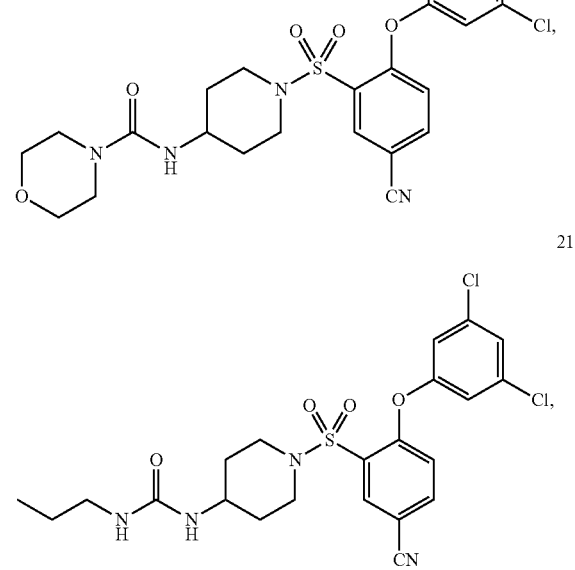
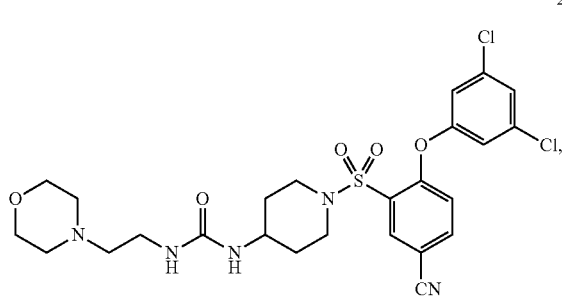
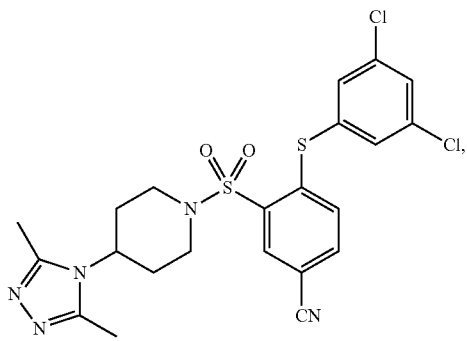

27
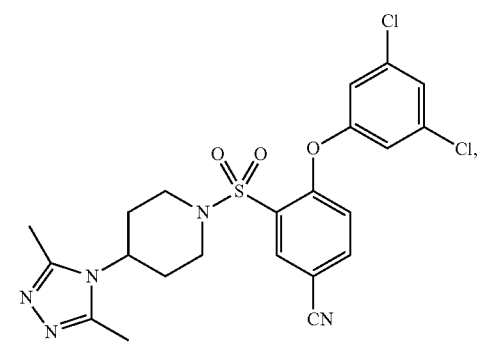
28
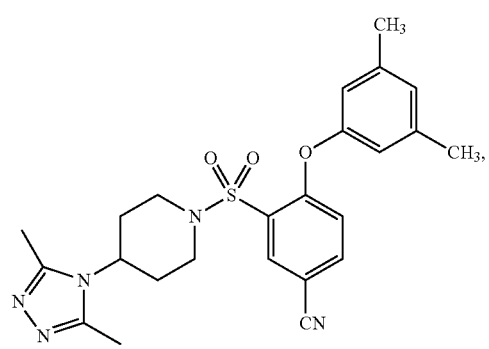
29
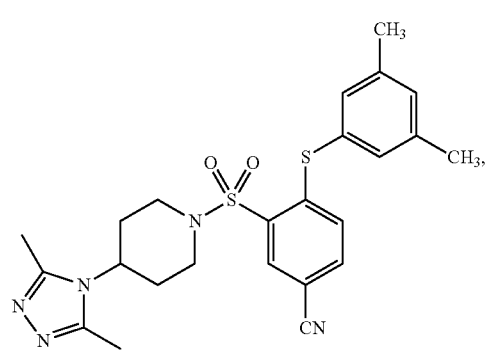
30
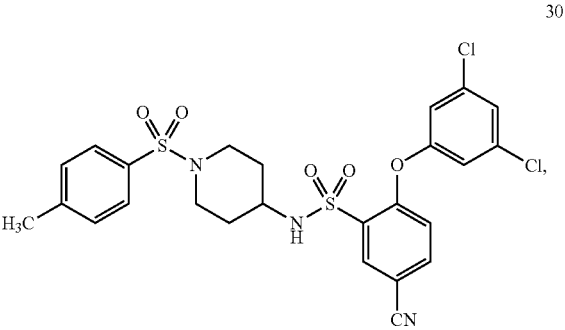
31
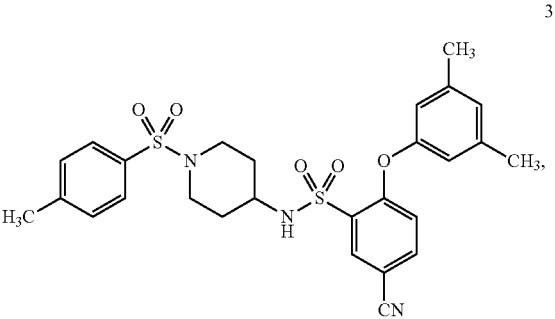
32
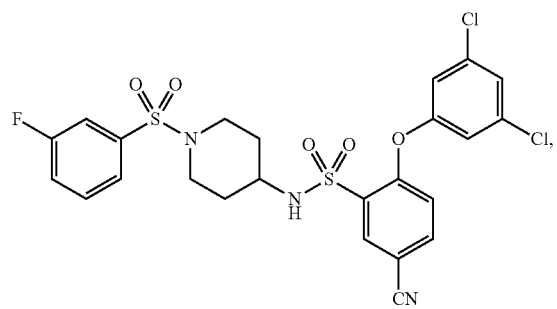
33
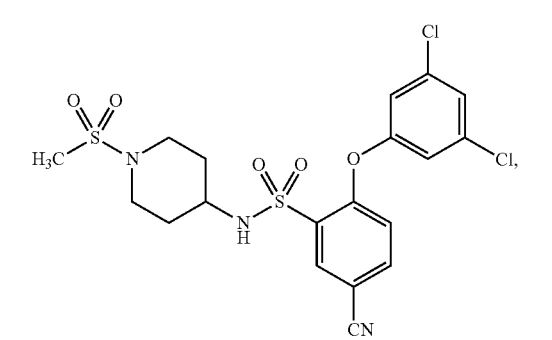
34
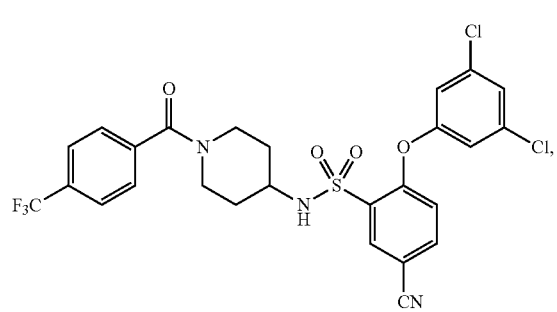
35
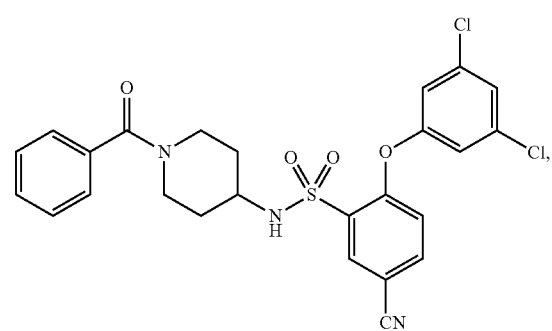

36
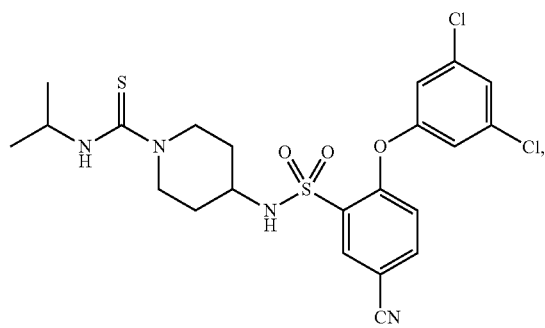
37
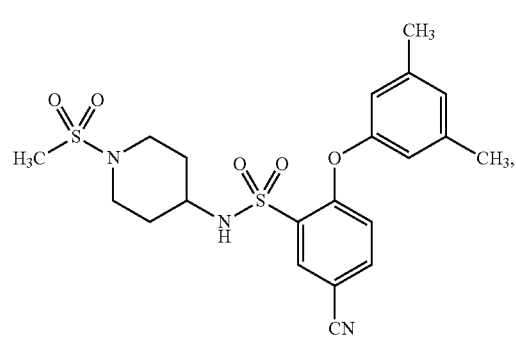
38
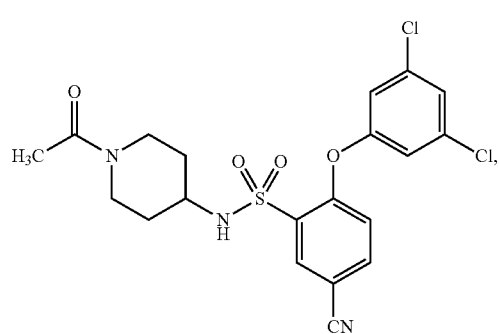
39
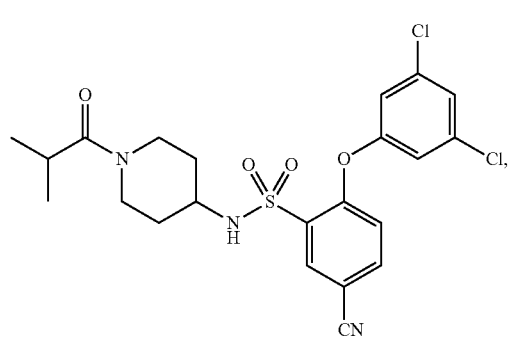
40
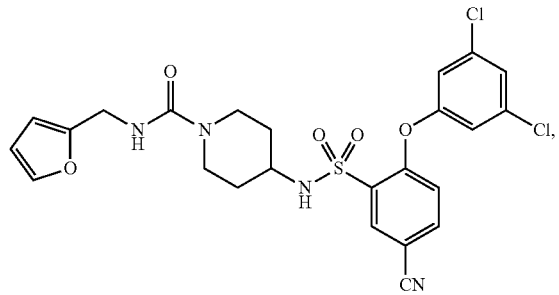
41
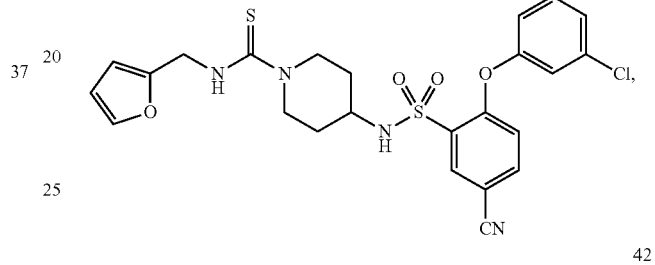
42
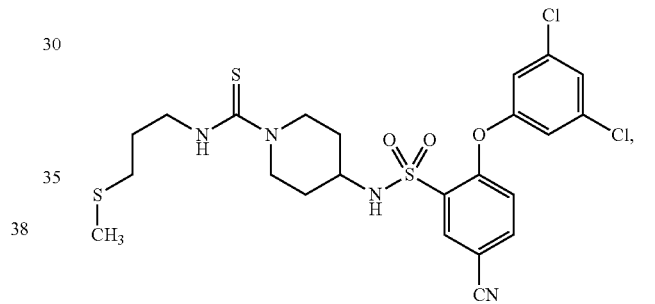
43
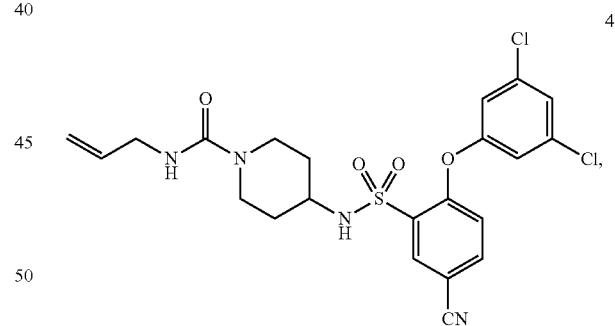
44
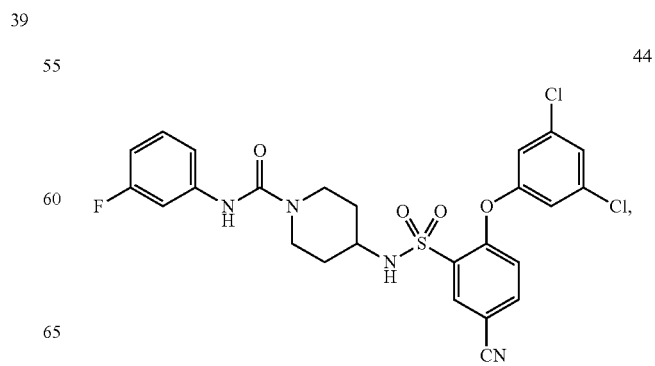

45
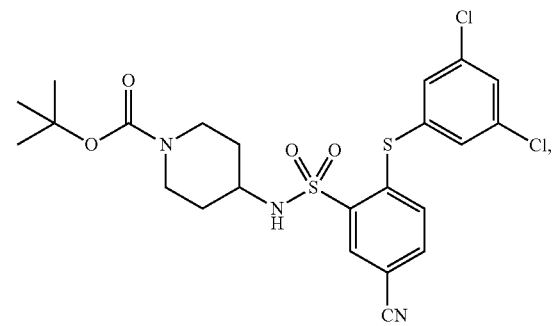
46
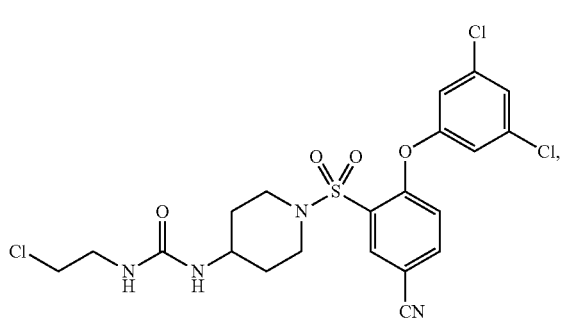
47
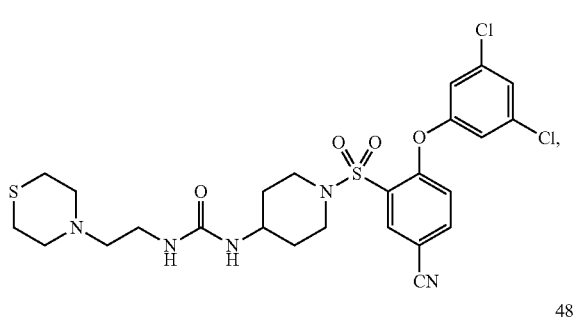
48
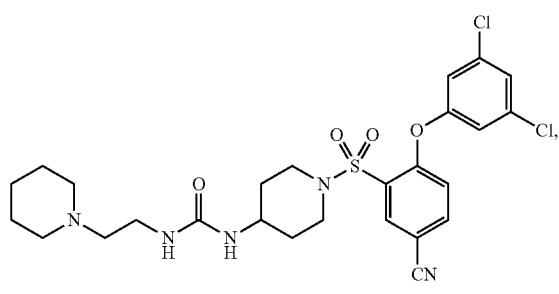
49
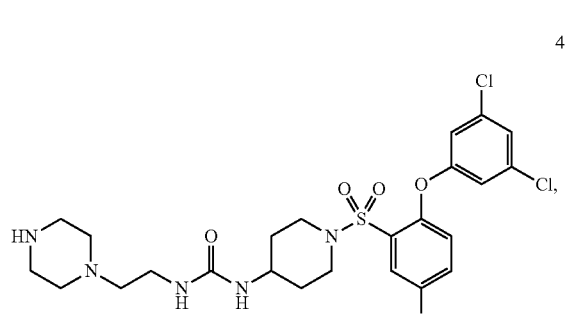
50
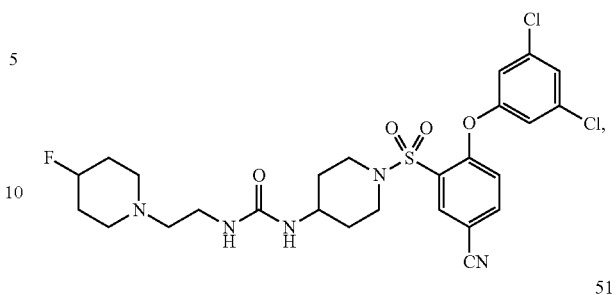
51
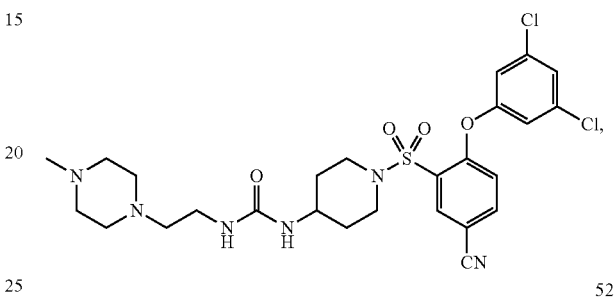
52
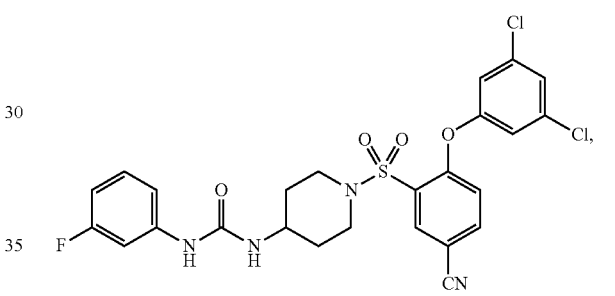
53
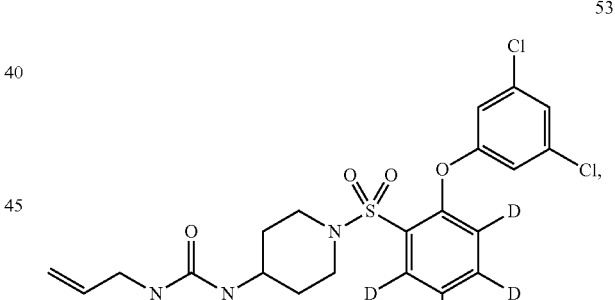
54
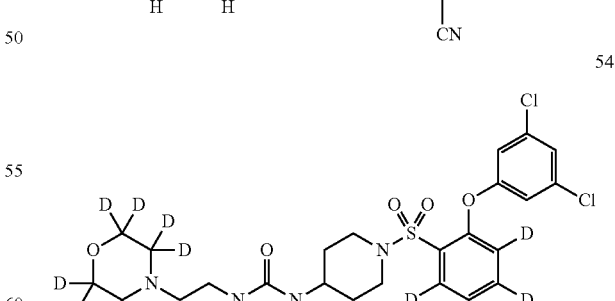
and enantiomers, mixtures of enantiomers, mixtures of two or more diastereomers, tautomers, and mixtures of two or more tautomers thereof and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In one embodiment, the compound provided here is a hydrochloride salt.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I or II, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

Compounds provided herein may be prepared, isolated, or obtained by any method known to one of skill in the art. For an example, a compound of Formula I can be prepared as shown in Scheme 1, where $P^1$ is hydrogen or an amino protecting group, e.g., Boc, Cbz, or Fmoc; and $R^L$ is a leaving group, e.g., chloro, bromo, iodo, imidazole, or a carboxylate.

Compound A reacts with compound B via a nucleophilic aromatic substitution reaction to form compound C with release of hydrochloride. The nitro group of the compound C was reduced to an amino group with a reducing reagent, e.g., sodium hydrosulfite or tin (II) chloride, to form analine D, which is subsequently converted into sulfonyl chloride E via the Sandmeyer reaction. Compound E is then coupled with amine F, wherein amino protecting group P¹ is optional in some embodiments. The removal of protecting group P¹ from compound G leads to compound H, which is reacted with Y—$R^L$ to form a compound of Formula I.

An alternative route to a compound of Formula I is shown in Scheme 2.

In a method similar to that described above and shown in Scheme 1, a compound of Formula II can be prepared as shown in Scheme 3, where P¹ is hydrogen or an amino protecting group, e.g., Boc, Cbz, or Fmoc; and $R^L$ is a leaving group, e.g., chloro, bromo, iodo, imidazole, or a carboxylate.

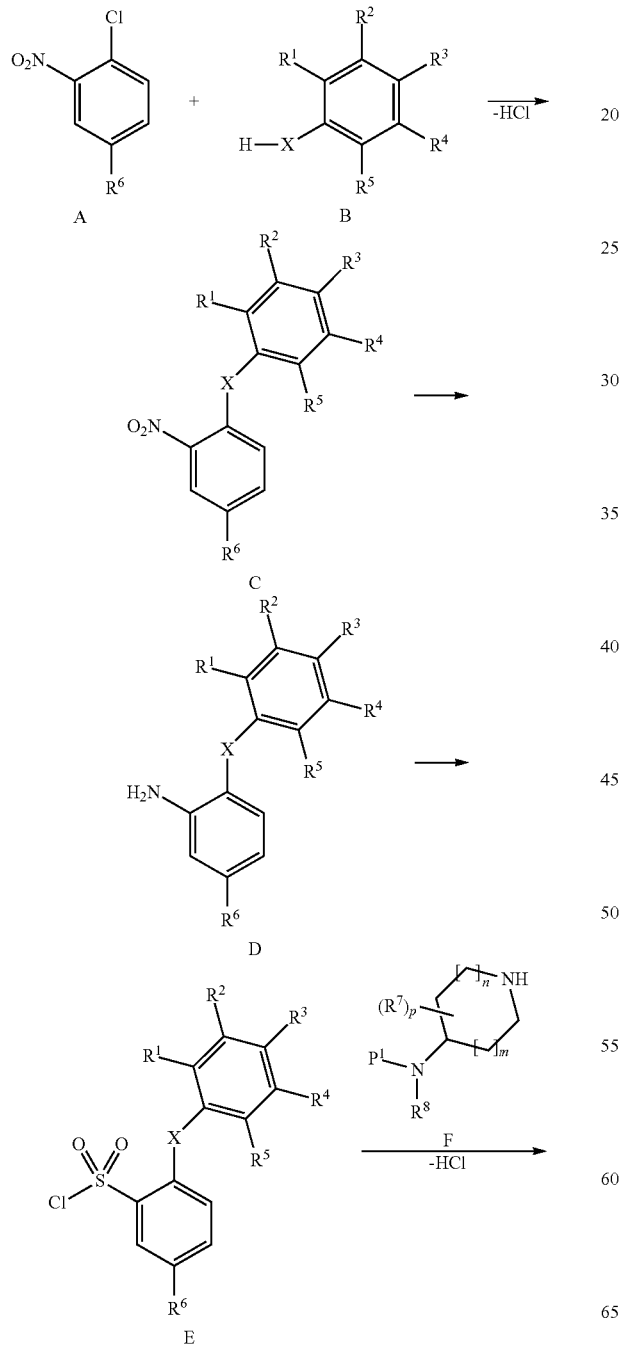

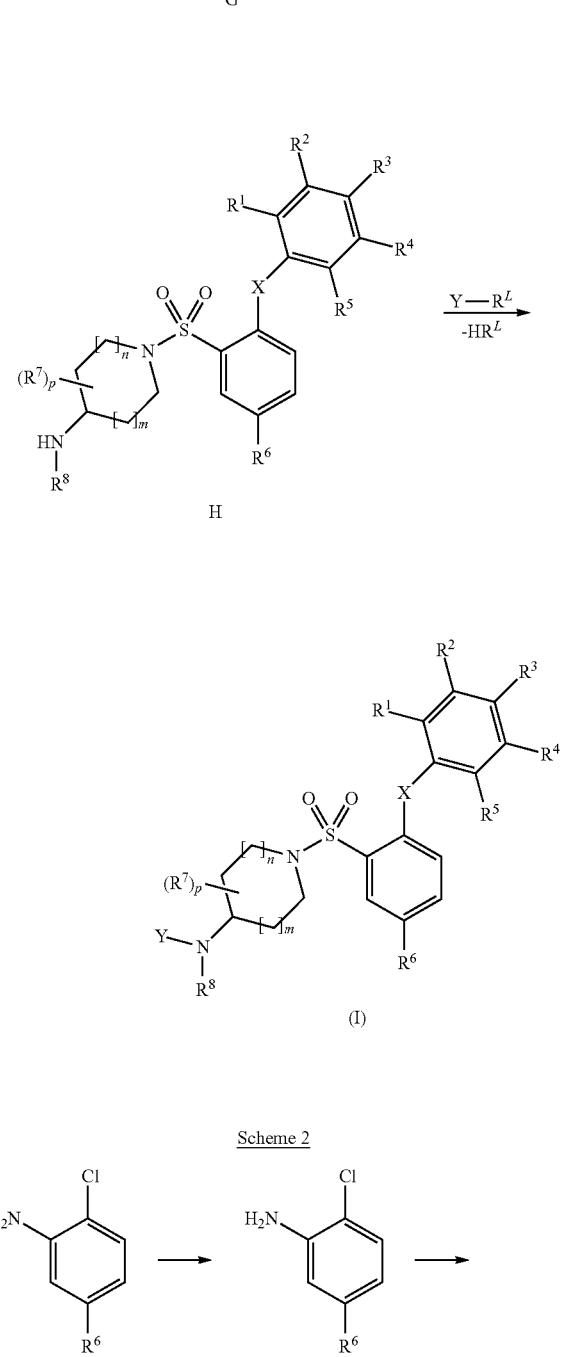

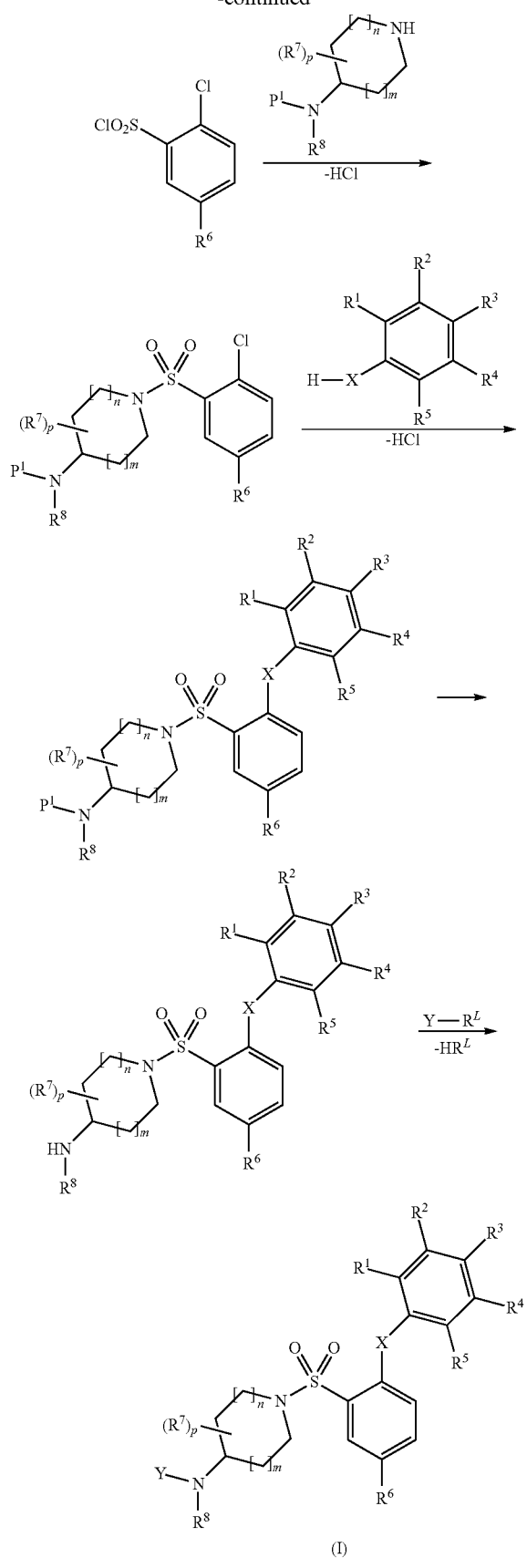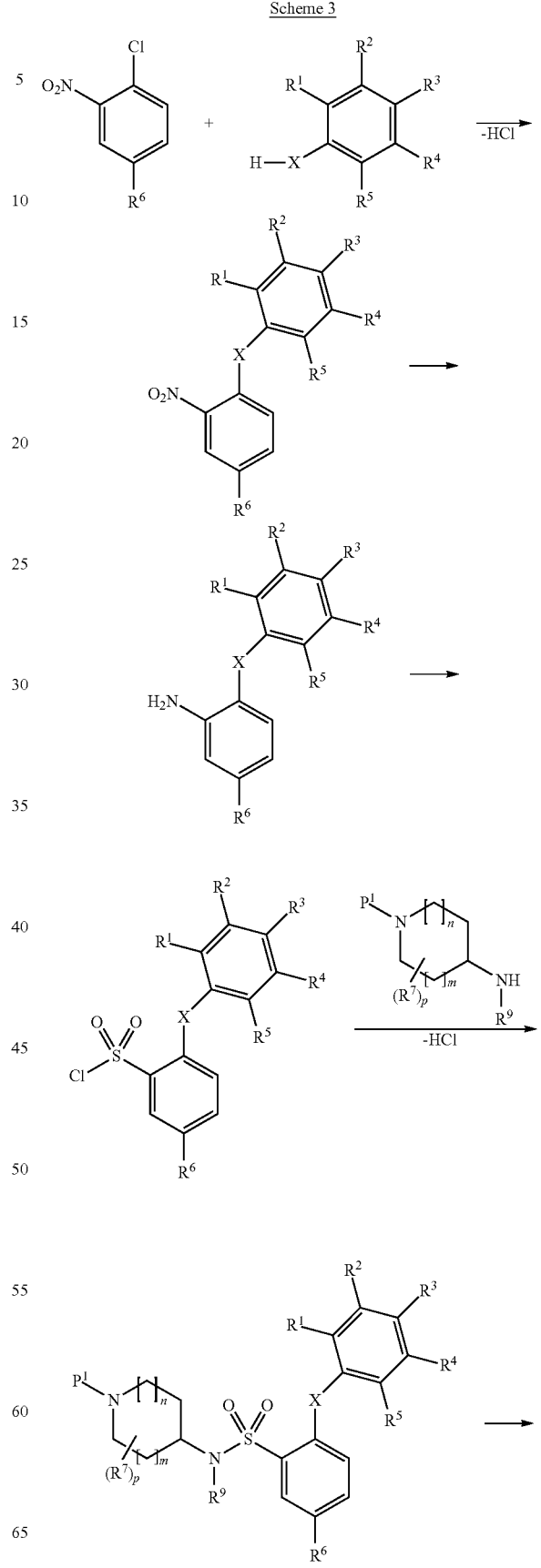
Scheme 3

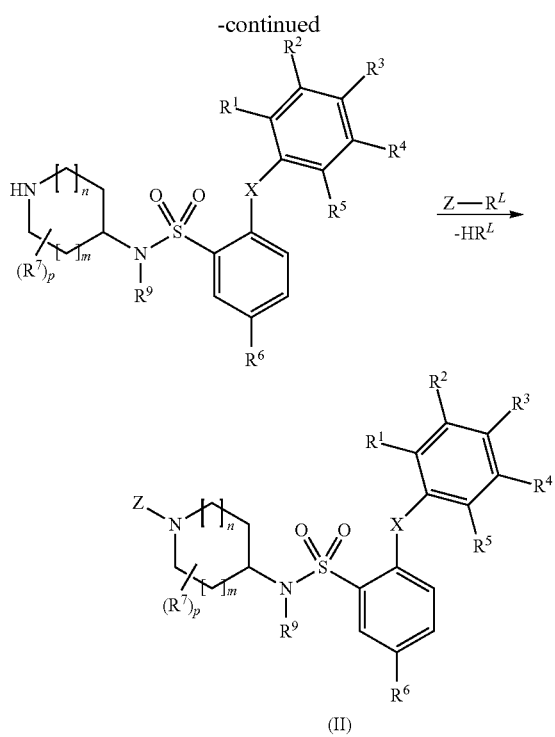

(II)

Pharmaceutical Compositions

Provided herein are pharmaceutical compositions comprising a compound provided herein, e.g., a compound of Formula I or II, as an active ingredient, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula I or II, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Delivery Technology, 2nd Edition, Rathbone et al., Eds., Marcel Dekker, Inc.: New York, N.Y., 2008).

In one embodiment, the pharmaceutical compositions are provided in a dosage form for oral administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

In yet another embodiment, the pharmaceutical compositions are provided in a dosage form for topical administration, which comprise a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate.

The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder, disease, or condition associated with CCR3 in a subject, which comprises administering to the subject a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In another embodiments, provided is a method of treating, preventing, or ameliorating one or more symptoms of a disorder, disease, or condition responsive to the modulation of CCR3 activity in a subject, comprising administering to the subject a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method of treating, preventing, or ameliorating one or more symptoms of a disorder, disease, or condition mediated by a CCR3 receptor in a subject, comprising administering to the subject a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of an eosinophil-related disorder, disease, or condition in a subject, comprising administering to the subject a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of a basophil-related disorder, disease, or condition in a subject, comprising administering to a subject, a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of a mast cell-related disorder, disease, or condition in a subject, comprising administering to a subject a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of an inflammatory disease in a subject, comprising administering to the subject a therapeutically effective amount of a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

The disorders, diseases, or conditions treatable with a compound provided herein, e.g., a compound of Formula I or II, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disorder, disease, or condition is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis, Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disorder, disease, or condition is asthma, exercise induced asthma, allergic rhinitis, atopic dermatitis, chronic obstructive plumonary disease, or allergic conjunctivitis.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with a CCR3 receptor, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day. In certain embodiments, the dosage level is ranging from about 0.001 to about 100 mg/kg per day. In certain embodiments, the dosage level is ranging from about 0.01 to about 75 mg/kg per day. In certain embodiments, the dosage level is ranging from about 0.1 to about 50 mg/kg per day. In certain embodiments, the dosage level is ranging from about 0.5 to about 25 mg/kg per day. In certain embodiments, the dosage level is ranging from about 1 to about 20 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating CCR3 activity, comprising contacting a CCR3 receptor with a compound provided herein, e.g., a compound of Formula I or II, including an enantiomer, a mixture of enantiomers, a mixture of two or more diastereomers, a tautomer, or a mixture of two or more tautomers thereof or a pharmaceutically acceptable salt, solvate, hydrate, or prodrug thereof. In one embodiment, the CCR3 receptor is expressed by a cell.

The compounds provided herein, e.g., a compound of Formula I or II, including an enantiomer, a mixture of enantiomers, a mixture of two or more diastereomers, a tautomer, or a mixture of two or more tautomers thereof or a pharmaceutically acceptable salt, solvate, hydrate, or prodrug thereof, can also be combined or used in combination with other agents useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted above.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

Such other agents, or drugs, can be administered, by a route and in an amount commonly used therefor, simultaneously or sequentially with the compounds provided herein, e.g., a compound of Formula I or II, including a single enantiomer, a mixture of enantiomers, or a mixture of diastereomers thereof; or a pharmaceutically acceptable salt, solvate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); DMSO (dimethylsulfoxide); DMSO-d$_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of N-(1-(5-cyano-2-(3,5-dichlorophenoxy)phenylsulfonyl)piperidin-4-yl)-3-fluorobenzenesulfonamide (25)

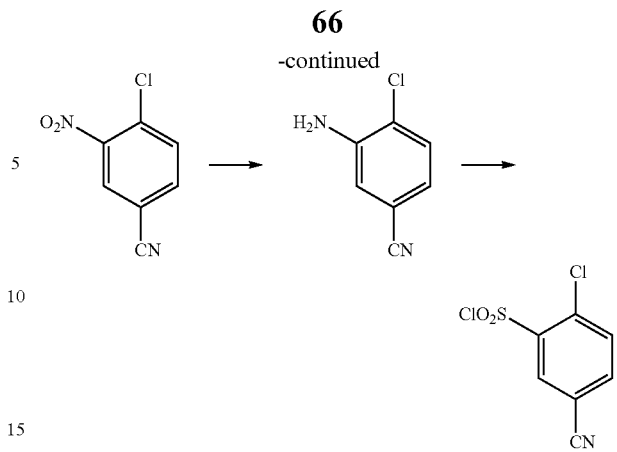

Commercially available 4-chloro-3-benzonitrile was dissolved in 4 parts THF. One part water was added with sodium hydrosulfide (3 eq.) and stirred overnight at 45° C. TLC (25% EtOAc in hexanes) confirmed completion of the reaction. THF was evaporated in vacuo and the product precipitated. The white solid was collected via vacuum filtration, washed with water and dried in a vacuum oven with gentle heating (97.0% yield).

The aniline product was ground in a mortar and pestle and dissolved in a mixture of 11 parts HCl and 4 parts acetic acid. In a separate vessel, 50 parts acetic acid was stirred with SO$_2$ gas until saturation (confirmed by weight). The HCl:acetic acid:aniline mixture was placed in a dry ice/ethanol bath at 10° C. Sodium nitrite (1.1 eq.) was dissolved in a minimal amount of water and added dropwise to the HCl:acetic acid:aniline mixture without allowing the temperature to rise above about −5° C. The resulting mixture was stirred 45 minutes to form the diazonium ion. Copper (I) chloride (0.1 eq.) and copper (II) chloride (0.25 eq.) were added to the SO$_2$/acetic acid solution and stirred 30 minutes and cooled in an ice bath to 10° C. The diazonium mixture was added in portions to the copper (I)/copper (II) chloride suspension, maintaining a temperature of 30° C. or lower. Once fully combined, the mixture was stirred until gas evolution ceased, forming a dark green solution. The mixture was then poured into 200 parts ice water slowly with stirring until the ice melted. The resulting white precipitate was collected by vacuum filtration and washed with water (72.9% yield).

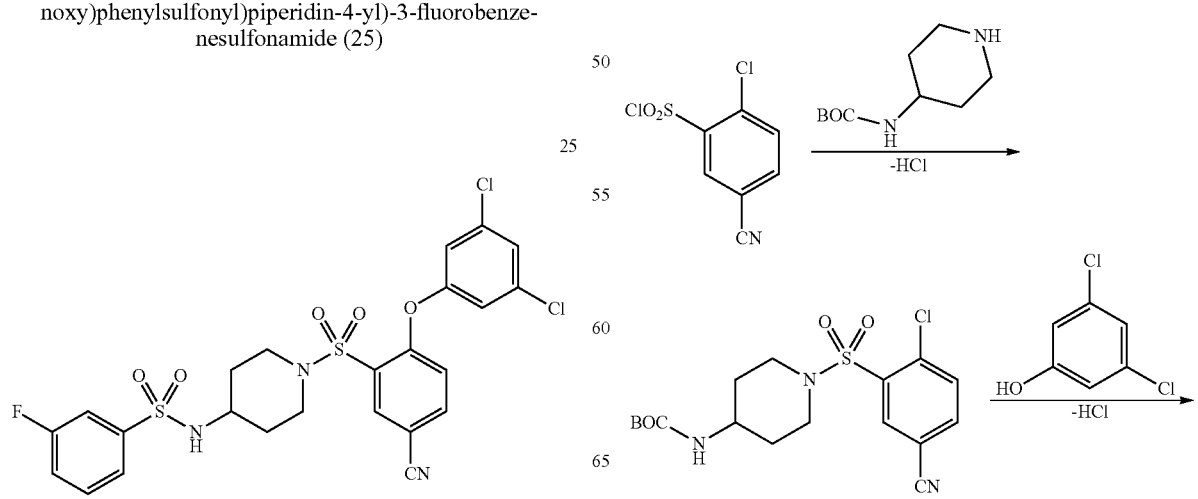

67
-continued

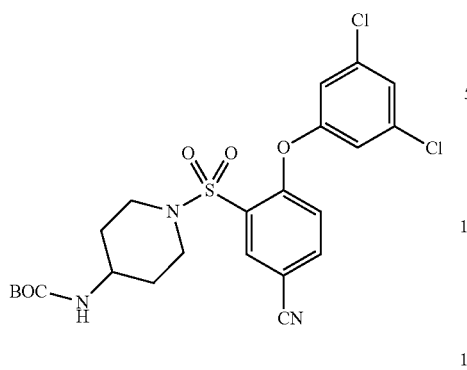

2-Chloro-5-cyanobenzene-1-sulfonyl chloride (8.00 g) was dissolved in 100 ml THF and N-BOC-4-aminopiperidine (5.79 g) was added. Slowly 6 equiv. of K$_2$CO$_3$ was added and the mixture stirred 1 hour at room temperature. 3,5-dichlorophenol (11.06 g) and 18-Crown-6 (4.66 g) were added and the reaction stirred 4 days at reflux (75° C.). The mixture was cooled and vacuum filtered, the filtrate concentrated in vacuo, redissolved in methylene chloride, partitioned with water and the aqueous layer extracted three times with methlyene chloride. The combined organic layers were washed with saturated sodium bicarbonate, water, brine and dried over MgSO$_4$. The filtrate was concentrated in vacuo, triturated with methylene chloride/diisopropyl ether and vacuum filtered to afford a yellow powder. The powder was recrystallized in MeOH to afford the product as a white powder (14.50 g, 87.3%).

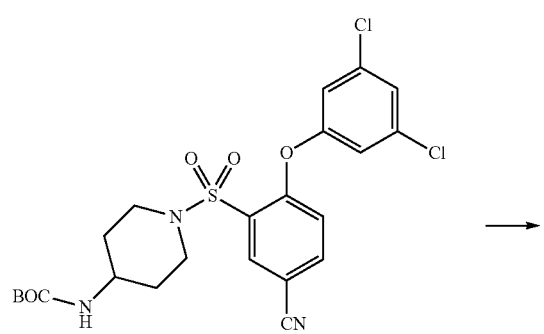

68
-continued

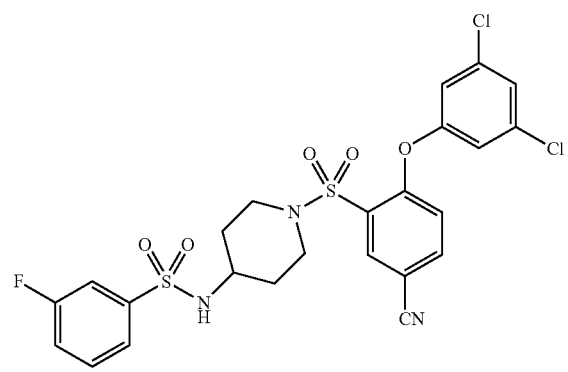

The BOC-protected amine (11.00 g) was suspended in methylene chloride (40.0 mL) and 11.0 ml of trifluoroacetic acid was added. The starting material was consumed after 22 hours of stirring (confirmed by HPLC). The mixture was condensed in vacuo and the resulting oil brought to pH 7 by addition of 3N NaOH (36.0 mL). The white suspension was filtered in vacuo, and the solid recrystallized in MeOH to afford a white powder (6.51 g, 73.0%).

The amine starting material, 3-(4-aminopiperidin-1-ylsulfonyl)-4-(3,5-dichlorophenoxy)benzonitrile, (100 mg) was dissolved in 3.0 mL of methylene chloride, and triethyl amine (0.042 mL, 1.3 eq.) followed by 3-fluorobenzesulfonyl chloride (58 mg, 1.3 eq.) was added. The starting material was consumed after 3.5 hours of stirring, as confirmed by TLC (50% EtOAc/hexanes). Purification by normal phase silica gel chromatography (14%, 35% EtOAc/Hexanes) provided the desired product, which was triturated with diisopropyl ether and vacuum filtered to yield a white powder (61 mg, 44.5%). $^1$H NMR (500 MHz, CDCl$_3$) δ: 8.24 (d, J=2 Hz, 1H), 7.78 (dd, J1=9 Hz, J2=2 Hz, 1H), 7.53 (m, 2H), 7.41 (m, 1H), 7.31 (m, 2H), 6.99 (m, 3H), 4.93 (t, J=7 Hz, 1H), 3.26 (m, 1H), 2.46 (m, 2H), 1.89 (m, 2H), 1.65 (m, 2H). MS (ESI+ ion, m/z): 585.

Example 2

Preparation of 1-(1-(5-cyano-2-(3,5-dichlorophenoxy)phenylsulfonyl)piperidin-4-yl)-3-(3-fluorophenyl)urea (4)

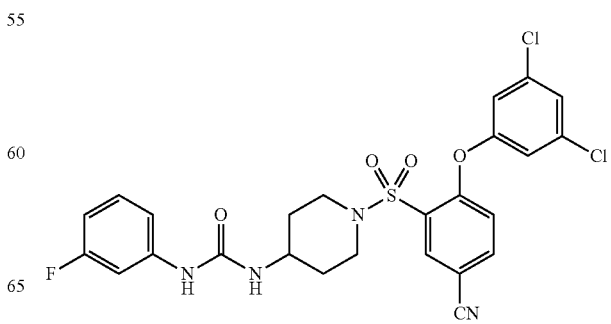

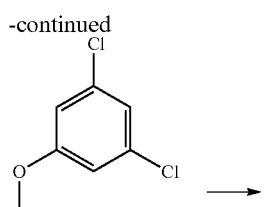

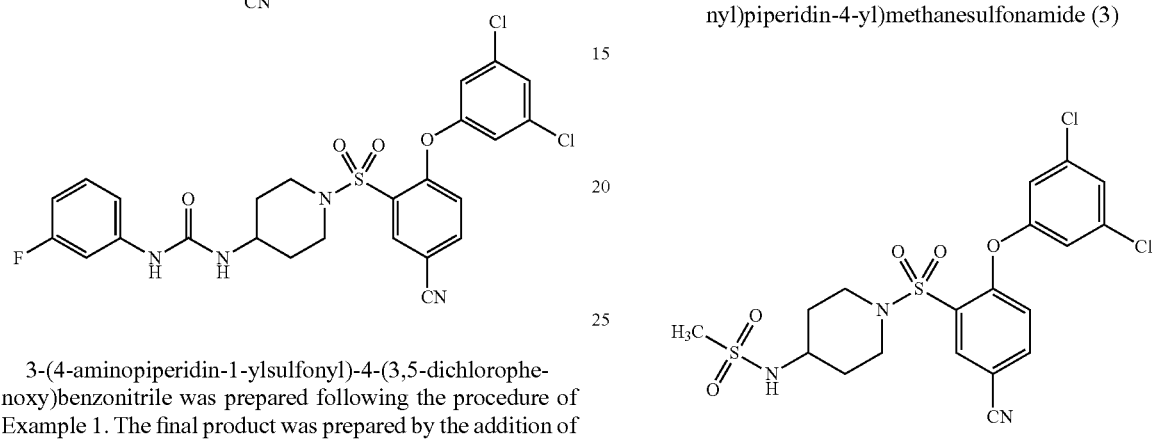

3-(4-aminopiperidin-1-ylsulfonyl)-4-(3,5-dichlorophenoxy)benzonitrile was prepared following the procedure of Example 1. The final product was prepared by the addition of triethyl amine (0.42 mL) followed by 3-fluorophenyl isocyanate to a solution of 3-(4-aminopiperidin-1-ylsulfonyl)-4-(3,5-dichlorophenoxy)benzonitrile (102 mg) in methylene chloride (4.0 mL). After stirring for 3 hours, the starting material was consumed, as confirmed by TLC (50% EtOAc/hexanes). 4 mL of hexanes was added and the product collected by vacuum filtration and washed with 1N HCl. The desired product was obtained as a white powder (99 mg, 73.3%). $^1$H NMR (500 MHz, DMSO-$d_6$) δ: 8.61 (s, 1H), 8.28 (d, J=2 Hz, 1H), 8.13 (dd, J1=9 Hz, J2=2 Hz, 1H), 7.55 (t, J=2 Hz, 2H), 7.42 (m, 1H), 7.37 (d, J=2 Hz, 2H), 7.34 (d, J=9 Hz, 1H), 7.22 (m, 1H), 6.99 (m, 1H), 6.68 (m, 1H), 6.33 (d, J=8 Hz, 1H), 3.61 (m, 3H), 2.96 (m, 2H), 1.88 (m, 2H), 1.40 (m, 2H). MS (ESI+ ion, m/z): 564.

Example 3

N-(1-(5-cyano-2-(3,5-dichlorophenoxy)phenylsulfonyl)piperidin-4-yl)benzamide (1)

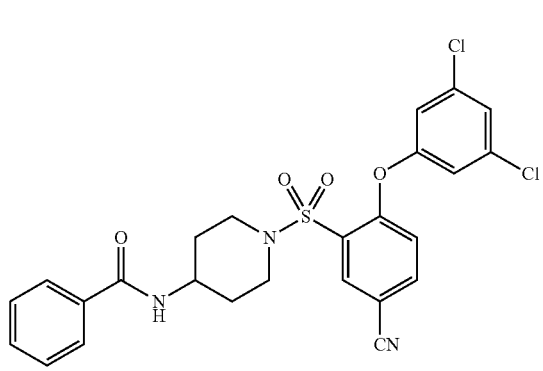 [SMILES: N#Cc1ccc(Oc2cc(Cl)cc(Cl)c2)c(S(=O)(=O)N2CCC(NC(=O)c3ccccc3)CC2)c1]

Compound 1 was prepared according to the methods described herein. $^1$H NMR (500 MHz, CDCl$_3$) δ: 8.32 (d, J=1 Hz, 1H), 7.79 (dd, J1=9 Hz, J2=2 Hz, 1H), 7.74 (d, J=8 Hz, 2H), 7.52 (m, 1H), 7.44 (m, 2H), 7.30 (s, 1H), 7.04 (d, J=9 Hz, 1H), 7.00 (s, 2H), 5.98 (J=7 Hz, 1H), 4.12 (m, 1H), 3.96 (m, 2H), 2.92 (m, 2H), 2.14 (m, 2H), 1.62 (m, 2H). MS (ESI+ ion, m/z): 531.

Example 4

N-(1-(5-cyano-2-(3,5-dichlorophenoxy)phenylsulfonyl)piperidin-4-yl)methanesulfonamide (3)

Compound 3 was prepared according to the methods described herein. $^1$H NMR (500 MHz, CDCl$_3$) δ: 8.30 (d, J=2 Hz, 1H), 7.79 (dd, J1=9 Hz, J2=2 Hz, 1H), 7.30 (t, J=2 Hz, 1H), 7.03 (d, J=9 Hz, 1H), 6.98 (d, J=2 Hz, 2H), 4.19 (m, 1H), 3.85 (m, 2H), 3.47 (m, 1H), 2.99 (s, 3H), 2.91 (m, 1H), 2.09 (m, 2H), 1.63 (m, 2H). MS (ESI+ ion, m/z): 505.

Example 5

N-(1-(5-cyano-2-(3,5-dichlorophenoxy)phenylsulfonyl)piperidin-4-yl)acetamide (5)

Compound 5 was prepared according to the methods described herein. $^1$H NMR (500 MHz, DMSO-$d_6$) δ: 8.27 (d, J=2 Hz, 1H), 8.12 (dd, J1=9 Hz, J2=2 Hz, 1H), 7.82 (d, J=8 Hz, 1H), 7.55 (t, J=2 Hz, 1H), 7.36 (d, J=2 Hz, 2H), 7.32 (d, J=9 Hz, 1H), 3.67 (m, 1H), 3.61 (m, 2H), 2.91 (m, 2H), 1.77 (m, 5H), 1.36 (m, 2H). MS (ESI+ ion, m/z): 469.

Example 6

N-(1-(5-cyano-2-(3,5-dichlorophenoxy)phenylsulfonyl)piperidin-4-yl)isobutyramide (6)

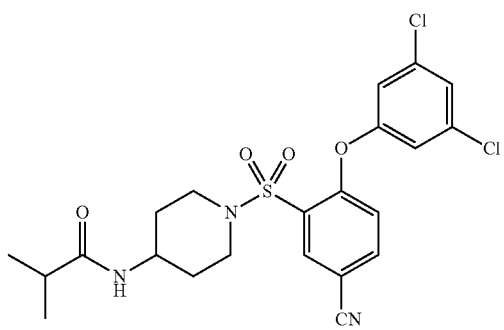 [SMILES: CC(C)C(=O)NC1CCN(S(=O)(=O)c2cc(C#N)ccc2Oc2cc(Cl)cc(Cl)c2)CC1]

Compound 6 was prepared according to the methods described herein. $^1$H NMR (500 MHz, DMSO-$d_6$) δ: 8.25 (s, 1H), 8.10 (d, J=9 Hz, 1H), 7.68 (s, 1H), 7.52 (s, 1H), 7.34 (s, 1H), 7.30 (d, J=9 Hz, 1H), 3.64 (m, 3H), 2.90 (m, 2H), 1.76 (m, 2H), 1.36 (m, 2H), 0.96 (d, J=7 Hz, 6H). MS (ESI+ ion, m/z): 497.

Example 7

N-(1-(5-cyano-2-(3,5-dichlorophenoxy)phenylsulfonyl)piperidin-4-yl)-4-methyl-1,2,3-thiadiazole-5-carboxamide (7)

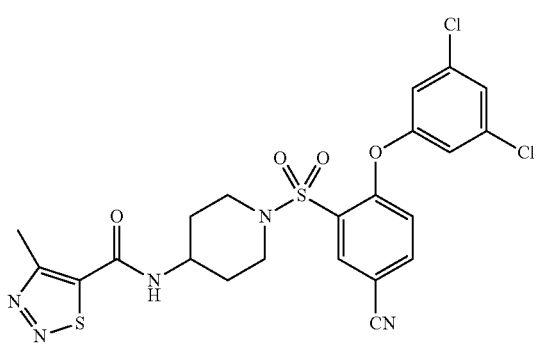 [SMILES: Cc1nnsc1C(=O)NC1CCN(S(=O)(=O)c2cc(C#N)ccc2Oc2cc(Cl)cc(Cl)c2)CC1]

Compound 7 was prepared according to the methods described herein. $^1$H NMR (500 MHz, DMSO-$d_6$) δ: 8.76 (d, J=8 Hz, 1H), 8.28 (d, J=2 Hz, 1H), 8.12 (dd, J1=2 Hz, J2=9 Hz, 1H), 7.56 (t, J=2 Hz, 1H), 7.38 (d, J=2 Hz, 2H), 7.33 (d, J=9 Hz, 1H), 3.93 (m, 1H), 3.69 (m, 2H), 2.96 (m, 2H), 2.74 (s, 3H), 1.91 (m, 2H), 1.51 (m, 2H). MS (ESI+ ion, m/z): 553.

Example 8

4-chloro-N-(1-(5-cyano-2-(3,5-dichlorophenoxy)phenylsulfonyl)piperidin-4-yl)butanamide (8)

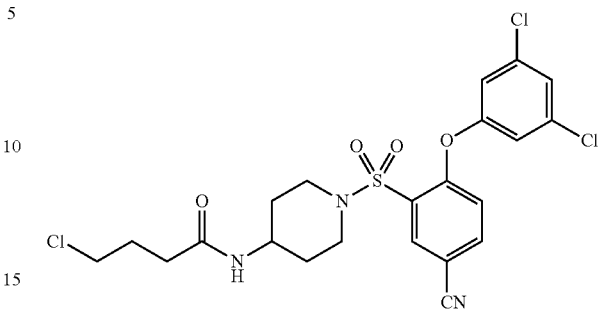

Compound 8 was prepared according to the methods described herein. $^1$H NMR (500 MHz, DMSO-$d_6$) 8.27 (d, J=2 Hz, 1H), 8.12 (dd, J1=2 Hz, J2=9 Hz, 1H), 7.87 (d, J=8 Hz, 1H), 7.55 (t, J=2 Hz, 1H), 7.36 (d, J=2 Hz, 2H), 7.32 (d, J=9 Hz, 1H), 3.70 (m, 1H), 3.61 (m, 4H), 2.92 (m, 2H), 2.20 (m, 2H), 1.91 (m, 2H), 1.78 (m, 2H), 1.37 (m, 2H).

Example 9

N-(1-(5-cyano-2-(3,5-dichlorophenoxy)phenylsulfonyl)piperidin-4-yl)cyclobutanecarboxamide (9)

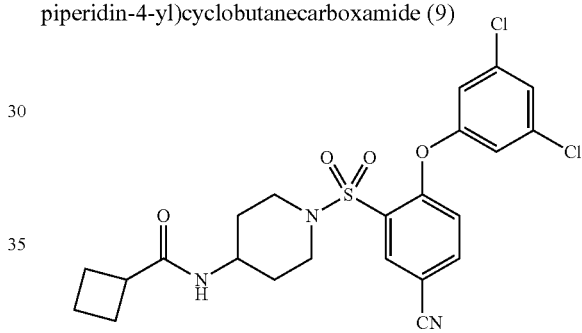

Compound 9 was prepared according to the methods described herein. $^1$H NMR (500 MHz, DMSO-$d_6$) δ: 8.26 (d, J=2 Hz, 1H), 8.11 (dd, J1=9 Hz, J2=2 Hz, 1H), 7.60 (d, J=8 Hz, 1H), 7.55 (t, J=2 Hz, 1H), 7.37 (d, J=2 Hz, 2H), 7.31 (d, J=9 Hz, 1H), 3.68 (m, 1H), 3.62 (m, 2H), 2.91 (m, 3H), 2.08 (m, 2H), 1.97 (m, 2H), 1.86 (m, 1H), 1.76 (m, 3H), 1.35 (m, 2H).

Example 10

N-(1-(5-cyano-2-(3,5-dichlorophenoxy)phenylsulfonyl)piperidin-4-yl)-4-methylbenzamide (10)

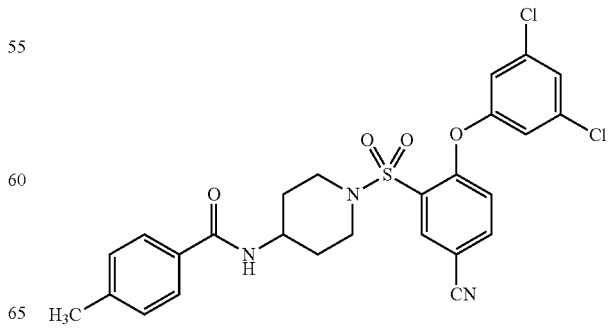

Compound 10 was prepared according to the methods described herein. $^1$H NMR (500 MHz, DMSO-$d_6$) δ: 8.28 (d, J=2 Hz, 1H), 8.22 (d, J=8 Hz, 1H), 8.12 (dd, J1=9 Hz, J2=2 Hz, 1H), 7.73 (d, J=8 Hz, 2H), 7.55 (t, J=2 Hz, 1H), 7.39 (d, J=2 Hz, 2H), 7.32 (d, J=9 Hz, 1H), 7.25 (d, J=8 Hz, 2H), 3.94 (m, 1H), 3.73 (m, 2H), 2.93 (m, 2H), 2.34 (s, 3H), 1.87 (m, 2H), 1.56 (m, 2H).

Example 11

N-(1-(5-cyano-2-(3,5-dichlorophenoxy)phenylsulfonyl)piperidin-4-yl)-3-fluorobenzamide (11)

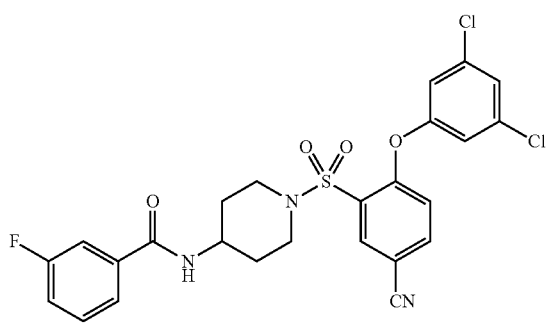 [SMILES: N#Cc1ccc(Oc2cc(Cl)cc(Cl)c2)c(S(=O)(=O)N2CCC(NC(=O)c3cccc(F)c3)CC2)c1]

Compound 11 was prepared according to the methods described herein. $^1$H NMR (500 MHz, DMSO-$d_6$) δ: 8.40 (d, J=8 Hz, 1H), 8.28 (d, J=2 Hz, 1H), 8.12 (dd, J1=9 Hz, J2=2 Hz, 1H), 7.68 (d, J=7 Hz, 1H), 7.55 (t, J=2 Hz, 1H), 7.52 (m, 1H), 7.39 (d, J=2 Hz, 2H), 7.37 (m, 1H), 7.33 (d, J=9 Hz, 1H), 3.95 (m, 1H), 3.73 (m, 2H), 2.94 (m, 2H), 1.88 (m, 2H), 1.56 (m, 2H).

Example 12

1-(1-(5-cyano-2-(3,5-dichlorophenoxy)phenylsulfonyl)piperidin-4-yl)-3-isopropylurea (12)

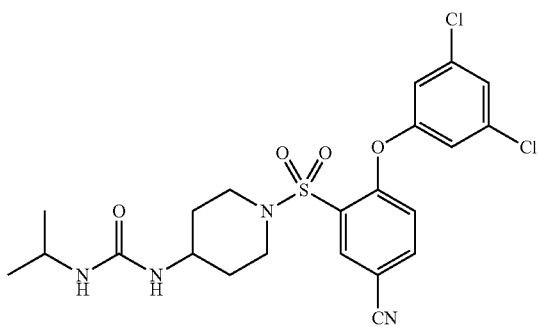 [SMILES: CC(C)NC(=O)NC1CCN(S(=O)(=O)c2cc(C#N)ccc2Oc2cc(Cl)cc(Cl)c2)CC1]

Compound 12 was prepared according to the methods described herein. $^1$H NMR (500 MHz, DMSO-$d_6$) δ: 8.26 (d, J=2 Hz, 1H), 8.12 (dd, J1=2 Hz, J2=9 Hz, 1H), 7.54 (t, J=2 Hz, 1H), 7.36 (d, J=2 Hz, 2H), 7.33 (d, J=9 Hz, 1H), 5.75 (d, J=8 Hz, 1H), 5.55 (d, J=8 Hz, 1H), 3.63 (m, 1H), 3.58 (m, 2H), 3.50 (m, 1H), 2.91 (m, 2H), 1.79 (m, 2H), 1.30 (m, 2H), 0.99 (d, J=6 Hz, 6H).

Example 13

1-allyl-3-(1-(5-cyano-2-(3,5-dichlorophenoxy)phenylsulfonyl)piperidin-4-yl)urea (13)

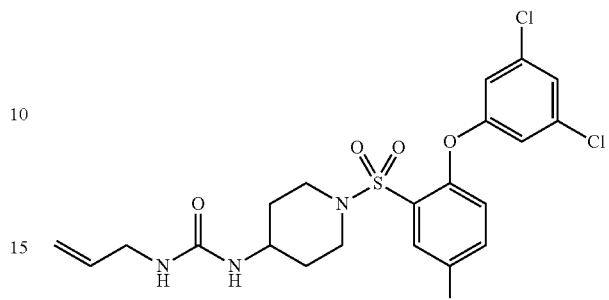

Compound 13 was prepared according to the methods described herein. $^1$H NMR (500 MHz, DMSO-$d_6$) δ: 8.27 (d, J=2 Hz, 1H), 8.12 (dd, J1=9 Hz, J2=2 Hz, 1H), 7.54 (t, J=2 Hz, 1H), 7.36 (d, J=2 Hz, 2H), 7.33 (d, J=9 Hz, 1H), 5.95 (d, J=8 Hz, 1H), 5.84 (m, 1H), 5.07 (m, 1H), 5.00 (m, 1H), 3.61 (m, 3H), 3.52 (m, 2H), 2.91 (m, 2H), 1.81 (m, 2H), 1.31 (m, 2H).

Example 14

1-(1-(5-cyano-2-(3,5-dichlorophenoxy)phenylsulfonyl)piperidin-4-yl)-3-p-tolylurea (14)

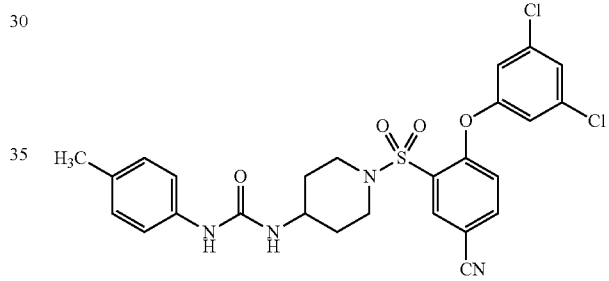

Compound 14 was prepared according to the methods described herein. $^1$H NMR (500 MHz, DMSO-$d_6$) δ: 8.28 (d, J=2 Hz, 1H), 8.18 (s, 1H), 8.13 (dd, J1=9 Hz, J2=2 Hz, 1H), 7.55 (t, J=2 Hz, 1H), 7.37 (d, J=2 Hz, 2H), 7.34 (d, J=9 Hz, 1H), 7.23 (d, J=8 Hz, 2H), 7.00 (d, J=8 Hz, 2H), 6.13 (d, J=8 Hz, 1H), 3.60 (m, 3H), 2.95 (m, 2H), 2.20 (s, 3H), 1.87 (m, 2H), 1.39 (m, 2H). MS (ESI+ ion, m/z): 560; MS (ESI− ion, m/z): 558.

Example 15

1-(1-(5-cyano-2-(3,5-dichlorophenoxy)phenylsulfonyl)piperidin-4-yl)-3-(4-methoxyphenyl)urea (15)

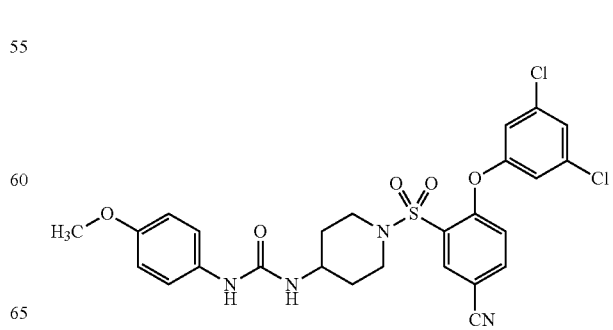

Compound 15 was prepared according to the methods described herein. ¹H NMR (500 MHz, DMSO-$d_6$) δ: 8.28 (d, J=2 Hz, 1H), 8.13 (dd, J1=9 Hz, J2=2 Hz, 1H), 8.10 (s, 1H), 7.55 (t, J=2 Hz, 1H), 7.37 (d, J=2 Hz, 2H), 7.34 (d, J=9 Hz, 1H), 7.25 (dd, J1=7 Hz, J2=2 Hz, 2H), 6.79 (dd, J1=7 Hz, J2=2 Hz, 2H), 6.08 (d, J=8 Hz, 1H), 3.68 (s, 3H), 3.59 (m, 3H), 2.95 (m, 2H), 1.87 (m, 2H), 1.38 (m, 2H). MS (ESI+ ion, m/z): 576. MS (ESI− ion, m/z): 574.

Example 16

1-(1-(5-cyano-2-(3,5-dichlorophenoxy)phenylsulfonyl)piperidin-4-yl)-3-(furan-2-ylmethyl)urea (16)

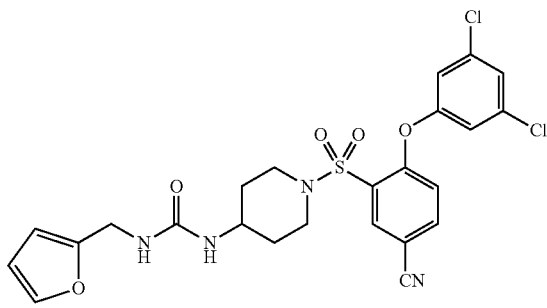 [SMILES: N#Cc1ccc(Oc2cc(Cl)cc(Cl)c2)c(S(=O)(=O)N2CCC(NC(=O)NCc3ccco3)CC2)c1]

Compound 16 was prepared according to the methods described herein. ¹H NMR (500 MHz, DMSO-$d_6$) δ: 8.27 (d, J=2 Hz, 1H), 8.12 (dd, J1=9 Hz, J2=2 Hz, 1H), 7.54 (m, 2H), 7.36 (d, J=2 Hz, 2H), 7.33 (d, J=9 Hz, 1H), 6.36 (m, 1H), 6.16 (m, 1H), 6.12 (m, 1H), 5.98 (d, J=8 Hz, 1H), 4.16 (d, J=6 Hz, 1H), 3.54 (m, 3H), 2.91 (m, 2H), 1.81 (m, 2H), 1.31 (m, 2H). MS (ESI+ ion, m/z): 550. MS (ESI− ion, m/z): 548.

Example 17

1-(1-(5-cyano-2-(3,5-dichlorophenoxy)phenylsulfonyl)piperidin-4-yl)-3-isopropylthiourea (17)

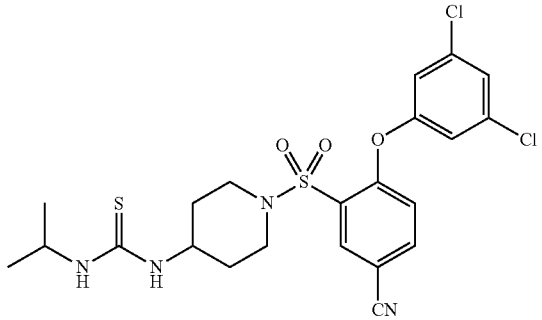 [SMILES: CC(C)NC(=S)NC1CCN(S(=O)(=O)c2cc(C#N)ccc2Oc2cc(Cl)cc(Cl)c2)CC1]

Compound 17 was prepared according to the methods described herein. ¹H NMR (500 MHz, DMSO-$d_6$) δ: 8.27 (d, J=2 Hz, 1H), 8.12 (dd, J1=2 Hz, J2=9 Hz, 1H), 7.54 (t, J=2 Hz, 1H), 7.34 (m, 3H), 7.19 (m, 1H), 7.12 (m, 1H), 4.22 (m, 1H), 4.10 (m, 1H), 3.61 (m, 2H), 2.90 (m, 2H), 1.93 (m, 2H), 1.39 (m, 2H), 1.08 (d, J=7 Hz, 6H). MS (ESI+ ion, m/z): 529. MS (ESI− ion, m/z): 525.

Example 18

1-(1-(5-cyano-2-(3,5-dichlorophenoxy)phenylsulfonyl)piperidin-4-yl)-3-(3-(methylthio)propyl)thiourea (18)

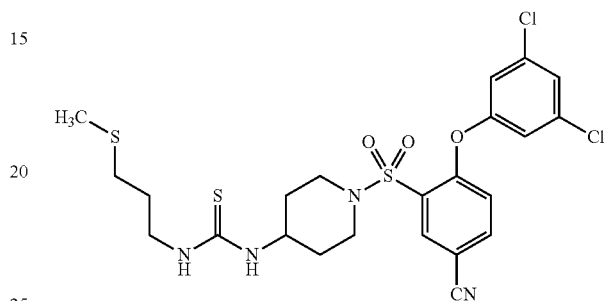

Compound 18 was prepared according to the methods described herein. ¹H NMR (500 MHz, DMSO-$d_6$) δ: 8.28 (d, J=2 Hz, 1H), 7.78 (dd, J1=2 Hz, J2=9 Hz, 1H), 7.29 (t, J=2 Hz, 1H), 7.02 (d, J=9 Hz, 1H), 7.00 (d, J=2 Hz, 2H), 6.20 (m, 1H), 5.98 (m, 1H), 4.35 (m, 1H), 3.91 (m, 2H), 3.46 (m, 2H), 2.88 (m, 2H), 2.57 (t, J=7 Hz, 2H), 2.19 (m, 2H), 2.10 (s, 3H), 1.87 (m, 2H), 1.57 (m, 2H). MS (ESI+ ion, m/z): 573. MS (ESI− ion, m/z): 572.

Example 19

N-(1-(5-cyano-2-(3,5-dichlorophenoxy)phenylsulfonyl)piperidin-4-yl)-3,5-dimethylisoxazole-4-sulfonamide (19)

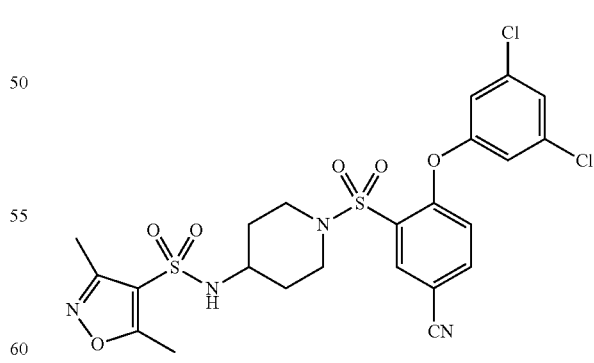

Compound 19 was prepared according to the methods described herein. ¹H NMR (500 MHz, DMSO-$d_6$) δ: 8.24 (d, J=2 Hz, 1H), 8.12 (dd, J1=9 Hz, J2=2 Hz, 1H), 7.54 (t, J=2 Hz, 1H), 7.34 (m, 3H), 3.54 (m, 2H), 3.16 (m, 1H), 2.88 (m, 2H), 2.57 (s, 3H), 2.31 (s, 3H), 1.61 (m, 2H), 1.39 (m, 2H). MS (ESI– ion, m/z): 583.

Example 20

N-(1-(5-cyano-2-(3,5-dichlorophenoxy)phenylsulfonyl)piperidin-4-yl)morpholine-4-carboxamide (20)

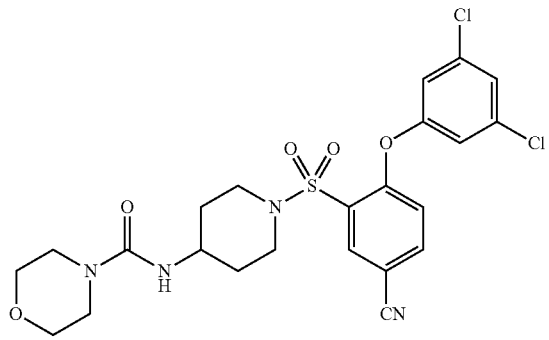 [SMILES: N#Cc1ccc(Oc2cc(Cl)cc(Cl)c2)c(S(=O)(=O)N2CCC(NC(=O)N3CCOCC3)CC2)c1]

Compound 20 was prepared according to the methods described herein. $^1$H NMR (500 MHz, DMSO-$d_6$) δ: 8.26 (d, J=2 Hz, 1H), 8.11 (dd, J1=9 Hz, J2=2 Hz, 1H), 7.55 (t, J=2 Hz, 1H), 7.36 (s, 2H), 7.31 (d, J=9 Hz, 1H), 6.30 (d, J=8 Hz, 1H), 3.67 (m, 1H), 3.57 (m, 1H), 3.52 (m, 4H), 3.23 (m, 4H), 2.85 (m, 2H), 1.79 (m, 2H), 1.41 (m, 2H). MS (ESI+ ion, m/z): 539.

Example 21

1-(1-(5-cyano-2-(3,5-dichlorophenoxy)phenylsulfonyl)piperidin-4-yl)-3-propylurea (21)

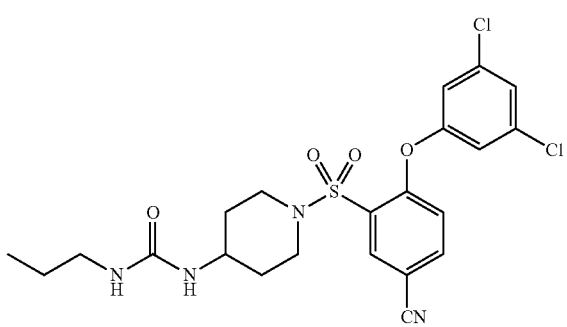 [SMILES: CCCNC(=O)NC1CCN(S(=O)(=O)c2cc(C#N)ccc2Oc2cc(Cl)cc(Cl)c2)CC1]

Compound 21 was prepared according to the methods described herein. $^1$H NMR (500 MHz, DMSO-$d_6$) δ: 8.26 (d, J=2 Hz, 1H), 8.12 (dd, J1=9 Hz, J2=2 Hz, 1H), 7.54 (t, J=2 Hz, 1H), 7.36 (s, 2H), 7.32 (d, J=9 Hz, 1H), 5.83 (d, J=8 Hz, 1H), 5.71 (t, J=6 Hz, 1H), 3.57 (m, 2H), 3.50 (m, 1H), 2.91 (m, 4H), 1.79 (m, 2H), 1.32 (m, 4H), 0.81 (t, J=7 Hz, 3H). MS (ESI+ ion, m/z): 511.

Example 22

1-(1-(5-cyano-2-(3,5-dichlorophenoxy)phenylsulfonyl)piperidin-4-yl)-3-(2-morpholinoethyl)urea (22)

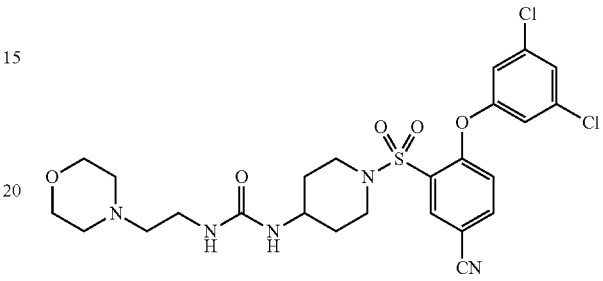

Compound 22 was prepared according to the methods described herein. $^1$H NMR (500 MHz, DMSO-$d_6$) δ: 8.27 (d, J=2 Hz, 1H), 8.12 (dd, J1=9 Hz, J2=2 Hz, 1H), 7.54 (t, J=2 Hz, 1H), 7.35 (s, 2H), 7.33 (d, J=9 Hz, 1H), 6.07 (d, J=8 Hz, 1H), 5.62 (t, J=5 Hz, 1H), 3.56 (m, 6H), 3.51 (m, 1H), 3.08 (m, 2H), 2.91 (m, 2H), 2.33 (m, 4H), 2.28 (m, 2H), 1.80 (m, 2H), 1.29 (m, 2H). MS (ESI+ ion, m/z): 582.

Example 23

1-(1-(5-cyano-2-(3,5-dichlorophenoxy)phenylsulfonyl)piperidin-4-yl)-3-cyclohexylurea (24)

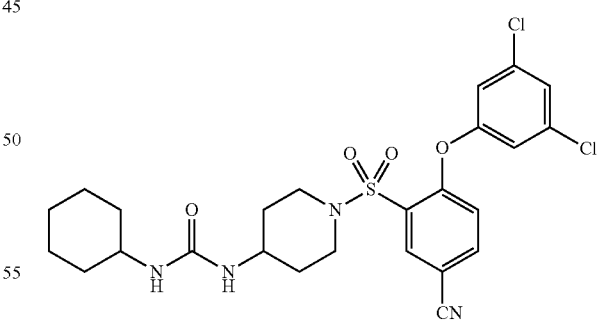

Compound 24 was prepared according to the methods described herein. $^1$H NMR (500 MHz, DMSO-$d_6$) δ: 8.27 (d, J=2 Hz, 1H), 8.12 (dd, J1=9 Hz, J2=2 Hz, 1H), 7.55 (t, J=2 Hz, 1H), 7.36 (d, J=2 Hz, 2H), 7.32 (d, J=9 Hz, 1H), 5.74 (d, J=8 Hz, 1H), 5.60 (d, J=8 Hz, 6H), 3.54 (m, 2H), 3.49 (m, 1H), 2.90 (m, 2H), 1.79 (m, 2H), 1.71 (m, 2H), 1.61 (m, 2H), 1.50 (m, 1H), 1.25 (m, 4H), 1.05 (m, 4H). MS (ESI+ ion, m/z): 552.

Example 24

4-(3,5-dichlorophenylthio)-3-(4-(3,5-dimethyl-4H-1,2,4-triazol-4-yl)piperidin-1-ylsulfonyl)benzonitrile (26)

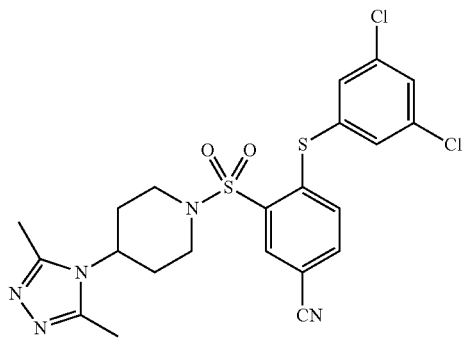 [SMILES: Cc1nnc(C)n1C1CCN(S(=O)(=O)c2cc(C#N)ccc2Oc2cc(Cl)cc(Cl)c2)CC1]

Compound 26 was prepared according to the methods described herein. $^1$H NMR (500 MHz, DMSO-d$_6$) δ: 8.29 (d, J=2 Hz, 1H), 7.93 (dd, J1=9 Hz, J2=2 Hz, 1H), 7.84 (t, J=2 Hz, 1H), 7.71 (d, J=2 Hz, 2H), 7.14 (d, J=9 Hz, 1H), 4.21 (m, 1H), 3.93 (m, 2H), 2.98 (m, 2H), 2.35 (s, 6H), 2.04 (m, 2H), 1.93 (m, 2H). MS (ESI+ ion, m/z): 522.

Example 25

4-(3,5-dichlorophenoxy)-3-(4-(3,5-dimethyl-4H-1,2,4-triazol-4-yl)piperidin-1-ylsulfonyl)benzonitrile (27)

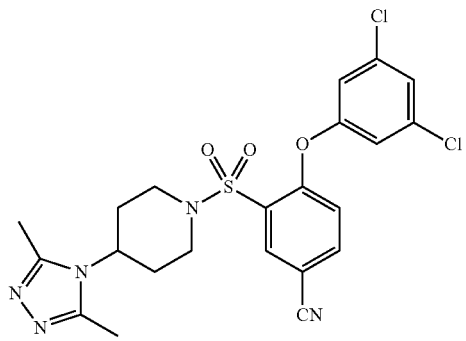

Compound 27 was prepared according to the methods described herein. $^1$H NMR (500 MHz, DMSO-d$_6$) δ: 8.33 (d, J=2 Hz, 1H), 8.16 (dd, J1=9 Hz, J2=2 Hz, 1H), 7.55 (t, J=2 Hz, 1H), 7.40 (d, J=9 Hz, 1H), 7.35 (d, J=2 Hz, 2H), 4.17 (m, 1H), 3.86 (m, 2H), 2.93 (m, 2H), 2.33 (s, 6H), 2.01 (m, 2H), 1.91 (m, 2H). MS (ESI+ ion, m/z): 507.

Example 26

3-(4-(3,5-dimethyl-4H-1,2,4-triazol-4-yl)piperidin-1-ylsulfonyl)-4-(3,5-dimethylphenoxy)benzonitrile (28)

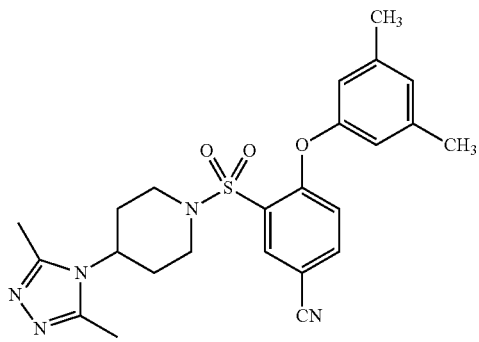 [SMILES: Cc1cc(C)cc(Oc2ccc(C#N)cc2S(=O)(=O)N2CCC(n3c(C)nnc3C)CC2)c1]

Compound 28 was prepared according to the methods described herein. $^1$H NMR (500 MHz, DMSO-d$_6$) δ: 8.28 (d, J=2 Hz, 1H), 8.06 (dd, J1=9 Hz, J2=2 Hz, 1H), 7.06 (d, J=9 Hz, 1H), 6.97 (s, 1H), 6.84 (s, 1H), 4.18 (m, 1H), 3.88 (m, 2H), 2.95 (m, 2H), 2.33 (s, 6H), 2.30 (s, 6H), 1.99 (m, 2H), 1.91 (m, 2H). MS (ESI+ ion, m/z): 466.

Example 27

3-(4-(3,5-dimethyl-4H-1,2,4-triazol-4-yl)piperidin-1-ylsulfonyl)-4-(3,5-dimethylphenylthio)benzonitrile (29)

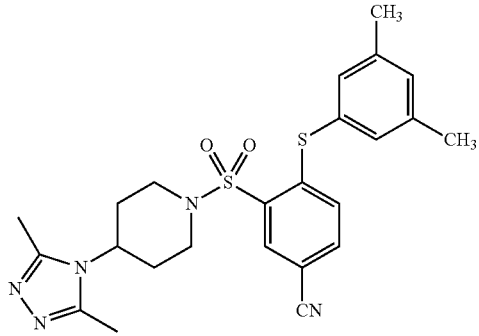

Compound 29 was prepared according to the methods described herein. $^1$H NMR (500 MHz, DMSO-d$_6$) δ: 8.27 (d, J=2 Hz, 1H), 7.89 (dd, J1=9 Hz, J2=2 Hz, 1H), 7.24 (s, 1H), 6.94 (d, J=9 Hz, 1H), 4.22 (m, 1H), 3.97 (m, 2H), 3.00 (m, 2H), 2.33 (m, 12H), 2.04 (m, 2H), 1.94 (m, 2H). MS (ESI+ ion, m/z): 482.

Example 28

5-cyano-2-(3,5-dichlorophenoxy)-N-(1-tosylpiperidin-4-yl)benzenesulfonamide (30)

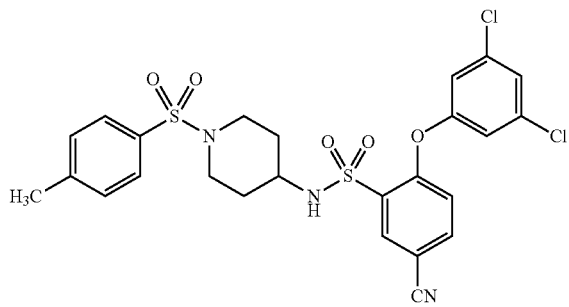 [SMILES: Cc1ccc(S(=O)(=O)N2CCC(NS(=O)(=O)c3cc(C#N)ccc3Oc3cc(Cl)cc(Cl)c3)CC2)cc1]

Compound 30 was prepared according to the methods described herein. ¹H NMR (500 MHz, DMSO-d$_6$) δ: 8.22 (d, J=2 Hz, 1H), 7.76 (dd, J1=9 Hz, J2=2 Hz, 1H), 7.57 (d, J=8 Hz, 2H), 7.31 (d, J=8 Hz, 2H), 7.26 (m, 1H), 6.98 (m, 3H), 5.11 (d, J=8 Hz, 1H), 3.60 (m, 2H), 3.22 (m, 1H), 2.43 (s, 3H), 2.36 (m, 2H), 1.84 (m, 2H), 1.67 (m, 2H). MS (ESI+ ion, m/z): 482.

Example 29

5-cyano-2-(3,5-dimethylphenoxy)-N-(1-tosylpiperidin-4-yl)benzenesulfonamide (31)

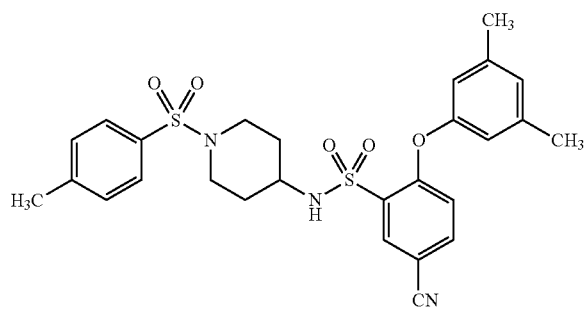

Compound 31 was prepared according to the methods described herein. ¹H NMR (500 MHz, DMSO-d$_6$) δ: 8.19 (d, J=2 Hz, 1H), 7.67 (dd, J1=9 Hz, J2=2 Hz, 1H), 7.58 (d, J=8 Hz, 2H), 7.31 (d, J=8 Hz, 2H), 6.95 (s, 1H), 6.89 (d, J=9 Hz, 1H), 6.68 (s, 1H), 4.97 (dd, J1=8 Hz, J2=2 Hz, 1H), 3.58 (m, 2H), 3.21 (m, 1H), 2.42 (s, 3H), 2.38 (m, 2H), 1.86 (m, 2H), 1.61 (m, 2H). MS (ESI+ ion, m/z): 540.

Example 30

5-cyano-2-(3,5-dichlorophenoxy)-N-(1-(3-fluorophenylsulfonyl)piperidin-4-yl)benzenesulfonamide (32)

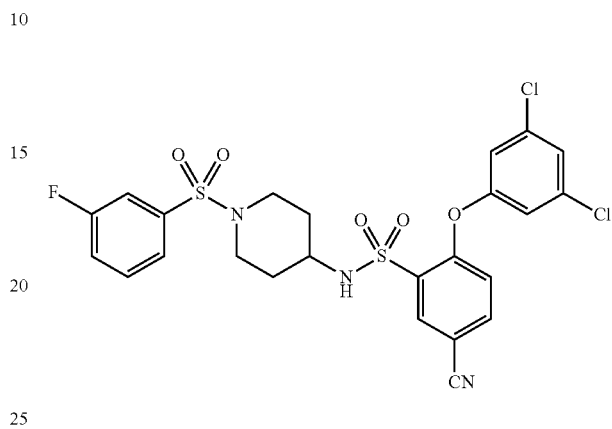

Compound 32 was prepared according to the methods described herein. ¹H NMR (500 MHz, DMSO-d$_6$) δ: 8.24 (d, J=2 Hz, 1H), 7.78 (dd, J1=9 Hz, J2=2 Hz, 1H), 7.53 (m, 2H), 7.41 (m, 1H), 7.31 (m, 2H), 6.99 (m, 3H), 4.93 (t, J=7 Hz, 1H), 3.64 (m, 2H), 3.22 (m, 1H), 2.46 (m, 2H), 1.89 (m, 2H), 1.65 (m, 2H). MS (ESI+ ion, m/z): 585.

Example 31

Preparation of 1-(2-chloroethyl)-3-(1-(5-cyano-2-(3,5-dichlorophenoxy)-phenylsulfonyl)piperidin-4-yl)urea (46)

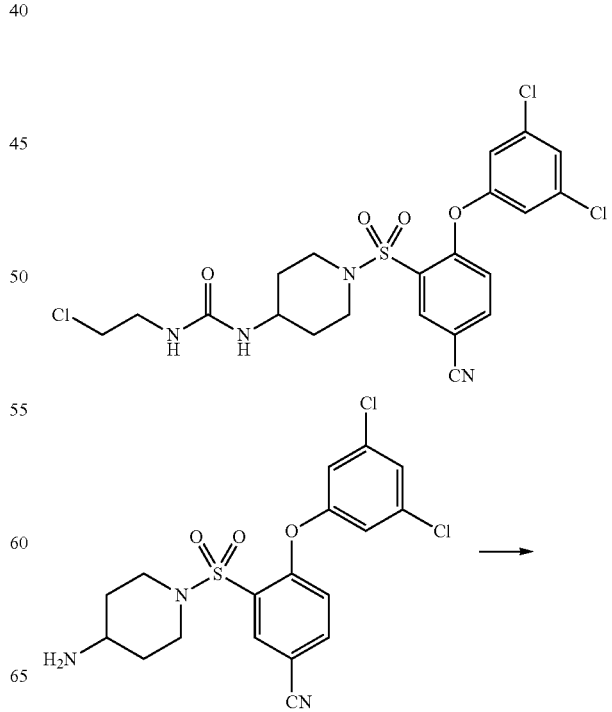

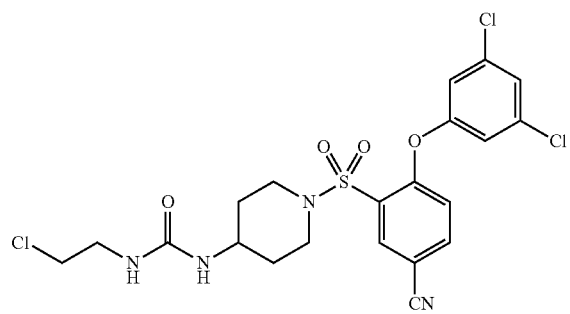

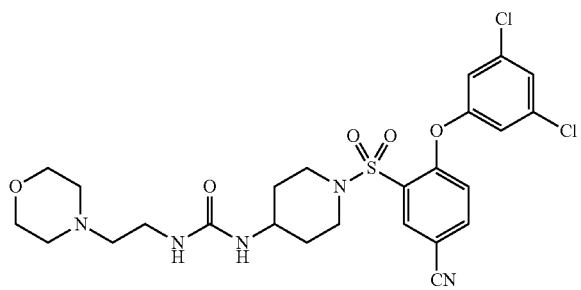

3-(4-aminopiperidin-1-ylsulfonyl)-4-(3,5-dichlorophenoxy)benzonitrile was prepared following the procedure of Example 1. The final product was prepared by dissolving 3-(4-aminopiperidin-1-ylsulfonyl)-4-(3,5-dichlorophenoxy) benzonitrile (1.00 g) in THF (30 mL) followed by the addition potassium carbonate (975 mg, 3.0 eq.), then 2-chloroethyl isocyanate (496 mg, 2.0 eq.) dropwise. After stirring for 1 hour, the starting material was consumed (confirmed by HPLC), and the mixture was filtered to remove potassium carbonate. The resulting filtrate was concentrated in vacuo, the solid triturated with dichlormethane and isopropyl ether, and fitted to obtain a white powder (838 mg, 67% yield, 97% purity).

Example 32

Preparation of 1-(1-(5-cyano-2-(3,5-dichlorophenoxy)phenylsulfonyl)piperidin-4-yl)-3-(2-morpholinoethyl)urea (22)

1-(2-chloroethyl)-3-(1-(5-cyano-2-(3,5-dichlorophenoxy)-phenylsulfonyl)piperidin-4-yl)urea (838 mg), potassium carbonate (655 mg, 3.0 eq.) and morpholine (413 mg, 3.0 eq.) were dissolved in acetonitrile (25 mL) and heated to reflux. After three hours, the reaction was complete (confirmed by HPLC). The mixture was then concentrated in vacuo, the solid triturated with dichlormethane and isopropyl ether to obtain a white powder. The powder was suspended in hot acetone, cooled in an ice bath, filtered, and washed with water to obtain the product as a white powder (601 mg, 65% yield, 97% purity).

Example 33

Preparation of 1-(1-(5-cyano-2-(3,5-dichlorophenoxy)phenylsulfonyl)piperidin-4-yl)-3-(2-morpholinoethyl)urea (22)

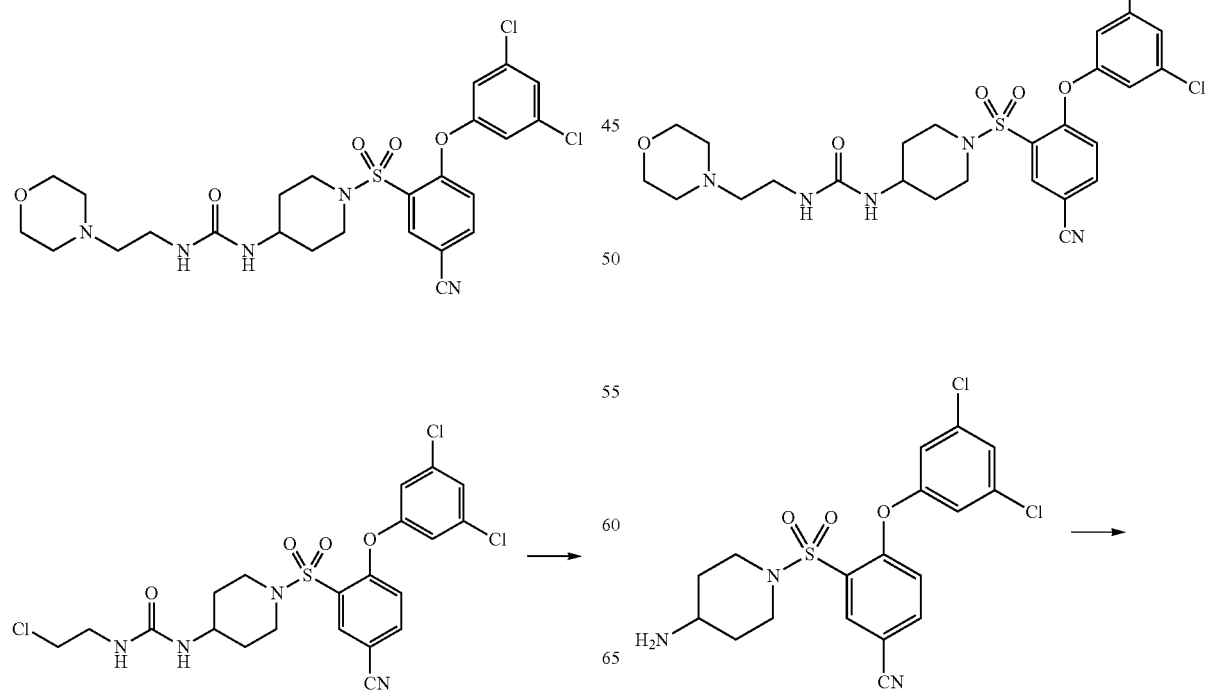

-continued

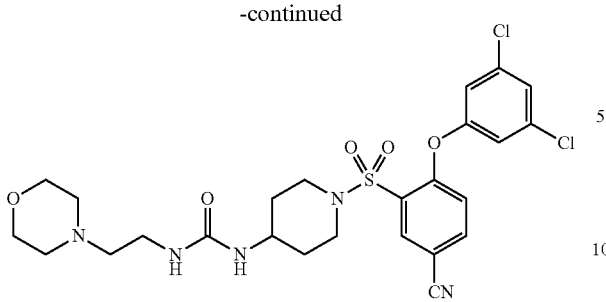

1-(1-(5-cyano-2-(3,5-dichlorophenoxy)phenylsulfonyl)-piperidin-4-yl)-3-(2-morpholinoethyl)urea (22) is prepared according to the following method as an alternative to the method of Example 32. 3-(4-aminopiperidin-1-ylsulfonyl)-4-(3,5-dichlorophenoxy)-benzonitrile (1.002 g), prepared according to Example 1, and carbonyldiimidazole (420 mg, 1.1 eq.) were combined in THF (15 mL) and stirred at room temperature. After 5 hours, starting material was consumed (confirmed by HPLC). 4-(2-aminoethyl)morpholine (512 mg, 2.0 eq.) was added and the mixture was stirred 19 hours. Concentration in vacuo provided a white solid, which was resuspended in dichlormethane, partitioned with water, and the aqueous layer extracted three times with dichloromethane. The combined organic layers were washed with brine, dried over anhydrous magnesium sulfate, filtered and concentrated in vacuo to yield a white solid. Trituration with isopropyl ether yielded a 96% pure product according to HPLC. The powder was suspended in minimal amounts of hot methanol, stirred at 60° C. for 30 minutes, cooled in an ice bath and vacuum filtered to obtain the product as a white powder (831 mg, 60.7% yield, 98% purity).

Example 34

1-(1-(5-cyano-2-(3,5-dichlorophenoxy)phenylsulfonyl)piperidin-4-yl)-3-(2-thiomorpholinoethyl)urea (47)

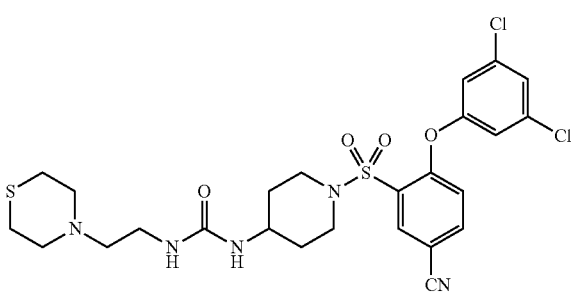 [SMILES: N#Cc1ccc(Oc2cc(Cl)cc(Cl)c2)c(S(=O)(=O)N2CCC(NC(=O)NCCN3CCSCC3)CC2)c1]

Compound 47 was prepared according to the methods described herein. $^1$H NMR (500 MHz, DMSO-$d_6$) δ: 8.26 (d, J=2 Hz, 1H), 8.11 (dd, J1=7 Hz, J2=2 Hz, 1H), 7.54 (t, J=1 Hz, 1H), 7.35 (d, J=2 Hz, 2H), 7.32 (d, J=9 Hz, 1H), 6.34 (m, 1H), 4.11 (t, J1=J2=9 Hz, 2H), 3.58 (m, 5H), 3.48 (m, 1H), 2.91 (m, 3H), 2.61 (m, 1H), 1.87 (m, 2H), 1.41 (m, 2H). MS (ESI+ ion, m/z): 599.

Example 35

1-(1-(5-cyano-2-(3,5-dichlorophenoxy)phenylsulfonyl)piperidin-4-yl)-3-(2-(piperidin-1-yl)ethyl)urea (48)

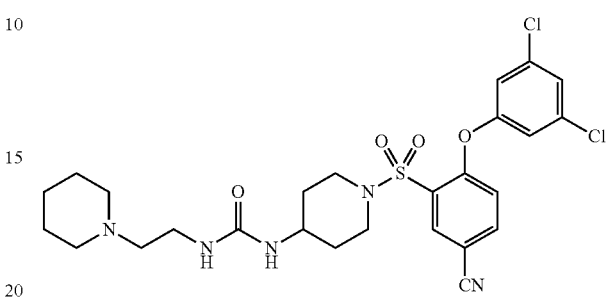

Compound 48 was prepared according to the methods described herein. $^1$H NMR (500 MHz, DMSO-$d_6$) δ: 8.56 (d, J=2 Hz, 1H), 8.11 (dd, J1=8 Hz, J2=2 Hz, 1H), 7.54 (t, J=2 Hz, 1H), 7.35 (d, J=2 Hz, 2H), 7.32 (d, J=9 Hz, 1H), 6.36 (m, 1H), 4.11 (t, J1=J2=9 Hz, 2H), 3.54 (m, 5H), 3.46 (m, 1H), 3.04 (m, 3H), 2.89 (m, 2H), 1.87 (m, 2H), 1.39 (m, 2H). MS (ESI+ ion, m/z): 580.

Example 36

1-(1-(5-cyano-2-(3,5-dichlorophenoxy)phenylsulfonyl)piperidin-4-yl)-3-(2-(piperazin-1-yl)ethyl)urea (49)

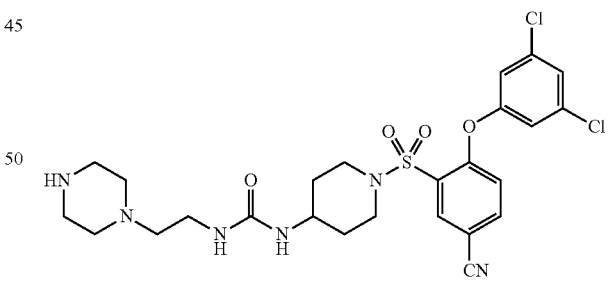

Compound 49 was prepared according to the methods described herein. $^1$H NMR (500 MHz, DMSO-$d_6$) δ: 8.26 (d, J=2 Hz, 1H), 8.11 (dd, J1=6 Hz, J2=2 Hz, 1H), 7.54 (t, J1=J2=1 Hz, 1H), 7.31 (d, J=6 Hz, 1H), 4.11 (t, J1=J2=9 Hz, 2H), 3.55 (m, 5H), 2.90 (m, 3H), 2.62 (m, 3H), 2.26 (m, 1H), 1.87 (m, 2H), 1.39 (m, 2H). MS (ESI+ ion, m/z): 581.

Example 37

1-(1-(5-cyano-2-(3,5-dichlorophenoxy)phenylsulfonyl)piperidin-4-yl)-3-(2-(4-fluoropiperidin-1-yl)ethyl)urea (50)

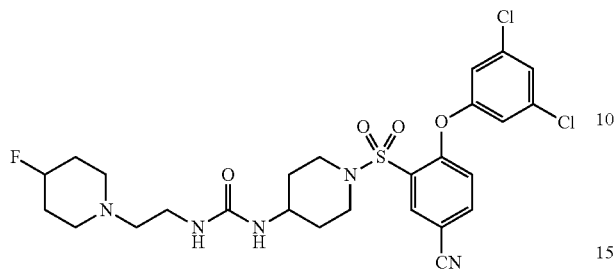

Compound 50 was prepared according to the methods described herein. $^1$H NMR (500 MHz, DMSO-$d_6$) δ: 8.26 (d, J=2 Hz, 1H), 8.12 (dd, J1=8 Hz, J2=2 Hz, 1H), 7.54 (t, J1=J2=1 Hz, 1H), 7.35 (s, 2H), 7.32 (d, J=9 Hz, 1H), 6.14 (d, J=8 Hz, 1H), 5.37 (m, 2H), 3.11 (m, 2H), 2.91 (m, 3H), 2.61 (m, 2H), 2.41 (m, 3H), 1.88 (m, 2H), 1.81 (m, 3H), 1.72 (m, 2H), 1.30 (m, 2H). MS (ESI+ ion, m/z): 598.

Example 38

1-(1-(5-cyano-2-(3,5-dichlorophenoxy)phenylsulfonyl)piperidin-4-yl)-3-(2-(4-methylpiperazin-1-yl)ethyl)urea (51)

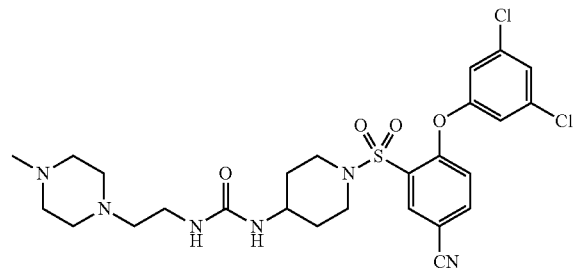 [SMILES: CN1CCN(CCNC(=O)NC2CCN(S(=O)(=O)c3cc(C#N)ccc3Oc3cc(Cl)cc(Cl)c3)CC2)CC1]

Compound 51 was prepared according to the methods described herein. $^1$H NMR (500 MHz, DMSO-$d_6$) δ: 8.26 (d, J=2 Hz, 1H), 8.11 (dd, J1=7 Hz, J2=2 Hz, 1H), 7.35 (s, 2H), 7.32 (d, J=9 Hz, 1H), 6.36 (s, 1H), 4.11 (t, J1=J2=8 Hz, 2H), 3.56 (m, 5H), 3.40 (m, 2H), 3.39 (m, 3H), 2.29 (m, 1H), 1.87 (m, 2H), 1.39 (m, 2H). MS (ESI+ ion, m/z): 596.

Example 39

1-allyl-3-(1-(5-cyano-3,4,6-trideutero-2-(3,5-dichlorophenoxy)phenylsulfonyl)piperidin-4-yl)urea (53)

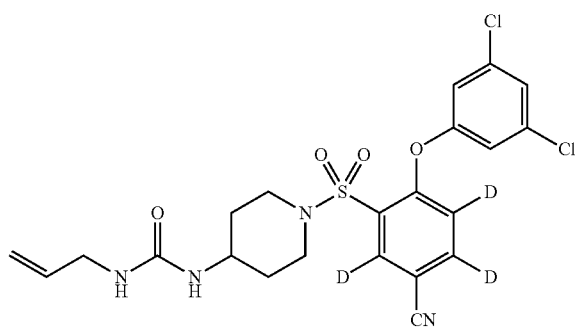 [SMILES: [2H]c1c([2H])c(Oc2cc(Cl)cc(Cl)c2)c(S(=O)(=O)N2CCC(NC(=O)NCC=C)CC2)c([2H])c1C#N]

Compound 54 was prepared according to the methods described herein. $^1$H NMR (500 MHz, DMSO-$d_6$) δ: 7.54 (s, 1H), 7.35 (s, 2H), 5.96 (d, J=8 Hz, 1H), 5.86 (t, J=6 Hz, 1H), 5.78 (m, 1H), 5.07 (dd, J1=8 Hz, J2=2 Hz, 1H), 4.99 (dd, J1=6 Hz, J2=2 Hz, 1H), 3.60 (m, 4H), 3.51 (m, 1H), 2.91 (m, 2H), 1.81 (m, 2H), 1.32 (m, 2H). MS (ESI+ ion, m/z): 534.

Example 40

1-(1-(5-cyano-3,4,6-trideutero-2-(3,5-dichlorophenoxy)phenylsulfonyl)piperidin-4-yl)-3-(2-(2,2,3,3,5,5,6,6-octadeutero-morpholino)ethyl)urea (54)

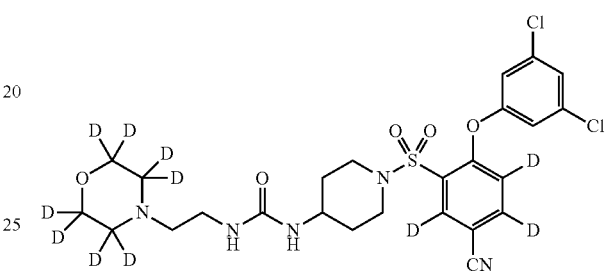

Compound 53 was prepared according to the methods described herein. $^1$H NMR (500 MHz, DMSO-$d_6$) δ: 7.35 (s, 2H), 6.08 (m, 1H), 5.63 (m, 1H), 4.14 (t, J1=J2=8 Hz, 2H), 3.57 (m, 3H), 3.40 (m, 2H), 2.91 (m, 1H), 1.87 (m, 2H), 1.40 (m, 2H). MS (ESI+ ion, m/z): 593.

Example 41

CCR3 Receptor Binding Assay

Cells were washed once with PBS and resuspended in a binding buffer (25 mM HEPES pH 7.6, 5 mM MgCl$_2$, 1 mM CaCl$_2$, 0.5% BSA, 0.1% NaN$_3$). 100 mL of cell suspension (2×10$^5$ cells/well) and 0.1 nM [$^{125}$I]-labeled human eotaxin/CCL11 (2000 Ci/mmol specific activity) were mixed in a 96-well U-bottom polypropylene plate, and incubated for 60 min at room temperature for the binding reaction. The cell suspension was then transferred to a filtration plate (#MAFB, Millipore), and washed 3 times with the binding buffer containing 0.5 M NaCl, scintillant added, and the radioactivity was counted on a TopCount (Packard). For the determination of non-specific binding, the cell suspension and [$^{125}$I]-labeled human eotaxin/CCL11 were incubated in the presence of 500 nM of unlabeled human eotaxin/CCL11. See, Iino et al., "Molecular cloning and functional characterization of cynomolgus monkey (*Macaca fascicularis*) CC chemokine receptor, CCR3," *Cytokine* 2002, 19, 276-286.

The biological results are summarized in Table 1, wherein A represents a value no greater than 50 nM, and B represents a value greater than 50 nM but no greater than 500 nM, C represents a value greater than 500 nM but no greater than 5 μM; and D represents a value greater than 5 μM.

TABLE 1

| Cmpd # | $K_i$ | Cmpd # | $K_i$ |
|---|---|---|---|
| 1 | — | 2 | D |
| 3 | — | 4 | — |
| 5 | — | 6 | — |
| 7 | — | 8 | — |
| 9 | — | 10 | — |
| 11 | — | 12 | — |
| 13 | — | 14 | — |
| 15 | — | 16 | — |
| 17 | — | 18 | — |
| 19 | — | 20 | — |
| 21 | — | 22 | A |
| 23 | C | 24 | — |
| 25 | B | 26 | — |
| 27 | — | 28 | — |
| 29 | — | 30 | B |
| 31 | D | 32 | D |
| 33 | B | 34 | D |
| 35 | D | 36 | B |
| 37 | D | 38 | B |
| 39 | D | 40 | — |
| 41 | — | 42 | — |
| 43 | — | 44 | B |
| 45 | C | 46 | — |
| 47 | A | 48 | A |
| 49 | A | 50 | A |
| 51 | A | 52 | C |
| 53 | A | 54 | A |

Example 42 hERG Receptor Binding Assay

Medium throughput screening of compounds for interaction with the human Ether-a-go-go related gene (hERG) was performed by modification of equilibrium dissociation assays using 125I-labelled peptide BeKm-1. BeKm-1, a scorpion toxin from the Central Asian scorpion Buthus eupeus, selectively blocks the hERG channel. Angelo, K., et al., 2003, *Pflugers Arch.-Eur. J. Physiol.*, 447: 55-63; Chiu, P J S, et al., *J. Pharmacol. Sci.*, 2004, 95: 311-319. Isolated membrane preparations from HEK-293 cells containing transfected hERG channels (hERG K+ Channel Membrane Target Systems™; Cat #, RBHERGM400UA) (Perkin Elmer, Boston, Mass.) were suspended in assay buffer A at a final concentration of 1:150 v/v. Compounds for screening, and non-radiolabelled BeKm-1, as well as 125I-BeKm-1 radioligand (Perkin Elmer; Cat #, NEX-412; Specific Activity 2,200 Ci/mmol), were also reconstituted in Buffer A. Assay components were incubated in 96-well, round-bottom polypropylene plates in the following ratio:

25 µl compound at appropriate concentrations
25 µl radiolabelled BeKm-1 at 0.8 nM (final concentration of 0.1 nM)
150 µl membrane preparation The assay was incubated with shaking for 1 hr at room temperature. Subsequently, the well contents were transferred to 96-well filtration plates (GF/C multiwell plates (MultiScreen™ HTS; Millipore, 290 Concord Road, Billerica, Mass. 01821 USA; Cat# MSFBN6B-XX pre-soaked in 0.3% polyethyleneimine; Acros Organics, NJ; Cat#178571000). Unbound radioactivity was removed and the membranes washed 4 times with ice-cold Buffer B, under vacuum. Plates were air-dried and bound radioactivity counted on a Packard Top-Count NXT™ microplate scintillation and luminescence counter (Packard Instrument Co., Downers Grove, Ill.). Equilibrium dissociation was analyzed and IC50 and/or Ki values were calculated using GraphPad Prism 4™ software (GraphPad Software, San Diego, Calif.). Assay Buffer A: (20 nM Hepes (MP Biomedicals, LLC; 29525 Fountain Parkway, Solon Ohio, 441389; Cat #1688449) in water, pH 7.2 with 1M Tris (Fisher Chemicals, Fair Lawn, N.J. 07410; Cat #, BP-1757-500); 100 µM KCl (Fisher Chemicals, Cat #, BP-366-500); 0.1% BSA (Sigma Aldrich, 3050 Spruce Street, St. Louis, Mo. 63103; Cat #, A3059).

Assay Buffer B: 20 mM Tris HCl, pH 7.3; 150 mM NaCl (Fisher Chemicals; Cat #, S78449).

The hERG binding assay results are summarized in Table 2, wherein A represents no measured activity (i.e., a value greater than 100 µM), and B represents a value greater than 10 µM but less than 100 µM and C represents a value less than 10 µM.

TABLE 2

| Cmpd # | $K_i$ | Cmpd # | $K_i$ |
|---|---|---|---|
| 2 | A | 5 | A |
| 8 | A | 10 | A |
| 11 | A | 12 | A |
| 13 | A | 16 | A |
| 17 | A | 18 | A |
| 25 | A | 30 | A |
| 33 | A | 36 | B |
| 38 | A | 52 | A |

The compounds provided herein have an improved hERG profile as compared to known CCR3 antagonists, many of which have a Ki value in the hERG binding assay less than 10 µM.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:
1. A compound of Formula I:

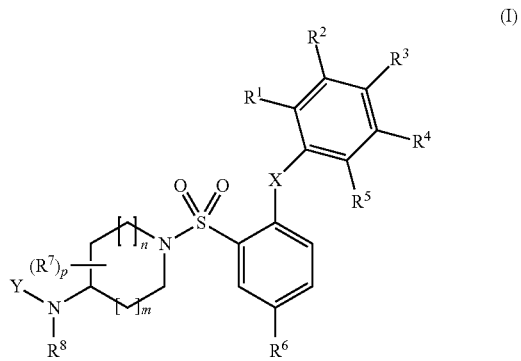

or an enantiomer, a mixture of enantiomers, a mixture of two or more diastereomers, a tautomer, or a mixture of two or more tautomers thereof; or a pharmaceutically acceptable salt, hydrate, or prodrug thereof;

wherein:

$R^1, R^2, R^3, R^4$, and $R^5$ are each independently hydrogen, halo, or $C_{1-6}$ alkyl;

$R^6$ is cyano or nitro;

$R^7$ is hydrogen or $C_{1-6}$ alkyl;

$R^8$ is hydrogen or $C_{1-6}$ alkyl;

X is O or S;

m is 0, 1, or 2;

n is 1 or 2;

p is 1, 2, 3, or 4; and

Y is —C(O)$R^{1a}$, —C(S)$R^{1a}$, —C(O)NR$^{1b}$R$^{1c}$, —C(S)NR$^{1b}$R$^{1c}$, —C(O)OR$^{1e}$, —S(O)$R^{1a}$ or —S(O)$_2$R$^{1a}$; wherein $R^{1a}, R^{1c}$, and $R^{1e}$ are each independently (a) $C_{1-6}$ alkyl, optionally substituted with one or more halo, $C_{1-6}$ alkoxy, $C_{1-6}$ alkylthio, heterocyclyl or heteroaryl; (b) $C_{2-6}$ alkenyl, optionally substituted with one or more halo; (c) $C_{3-7}$ cycloalkyl, optionally substituted with one or more halo, or one or two $C_{1-6}$ alkyl; (d) $C_{6-14}$ aryl, optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; (e) heteroaryl, optionally substituted with one or two $C_{1-6}$ alkyl; or (f) $C_{7-15}$ aralkyl optionally substituted with one or more halo, $C_{1-6}$ alkyl, where the alkyl is further optionally substituted with one, two, or three halo, or $C_{1-6}$ alkoxy, where the alkoxy is further optionally substituted with one, two, or three halo; and $R^{1b}$ is hydrogen or methyl; or $R^{1b}$ and $R^{1c}$ together with the N atom to which they are attached form heterocyclyl;

with the proviso that $R^{1e}$ is not t-butyl or benzyl.

2. The compound of claim 1, wherein $R^7$ is hydrogen; and p is 1, 2, 3, or 4.

3. The compound of claim 1, wherein $R^8$ is hydrogen or methyl; and

Y is —C(O)NR$^{1b}$R$^{1c}$ or —C(S)NR$^{1b}$R$^{1c}$; wherein $R^{1c}$ is (a) $C_{1-6}$ alkyl, optionally substituted with one or more halo or $C_{1-6}$ alkoxy, $C_{1-6}$ alkylthio, heterocyclyl or heteroaryl; (b) $C_{2-6}$ alkenyl; (c) $C_{3-7}$ cycloalkyl; or (d) $C_{6-14}$ aryl, optionally substituted with one or more halo, $C_{1-6}$ alkyl or $C_{1-6}$ alkoxy; and $R^{1b}$ is hydrogen or methyl; or $R^{1b}$ and $R^{1c}$ together with the N atom to which they are attached form heterocyclyl.

4. The compound of claim 1, wherein $R^8$ is hydrogen or methyl; and

Y is —C(O)NR$^{1b}$R$^{1c}$ or —C(S)NR$^{1b}$R$^{1c}$; wherein $R^{1c}$ is (a) $C_{1-6}$ alkyl, optionally substituted with heterocyclyl; and $R^{1b}$ is hydrogen or methyl.

5. The compound of claim 1, wherein $R^1$ is hydrogen;

$R^2$ is chloro or methyl;

$R^3$ is hydrogen;

$R^4$ is chloro or methyl;

$R^5$ is hydrogen;

$R^6$ is cyano;

$R^7$ is hydrogen; and

X is O or S.

6. The compound of claim 1, wherein two of $R^1, R^2, R^3, R^4$, and $R^5$ are halo or $C_{1-6}$ alkyl, and the remaining three are hydrogen.

7. The compound of claim 1, wherein two of $R^1, R^2, R^3, R^4$, and $R^5$ are chloro or methyl, and the remaining three are hydrogen.

8. The compound of claim 1, wherein X is O.

9. A compound selected from the group consisting of:

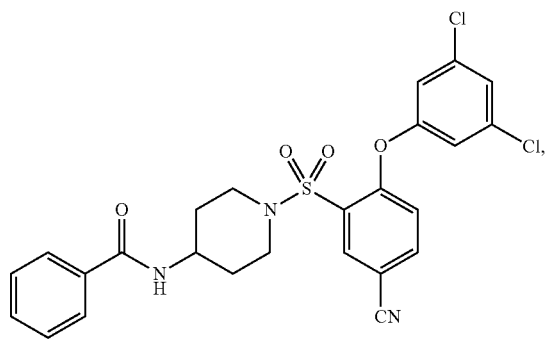

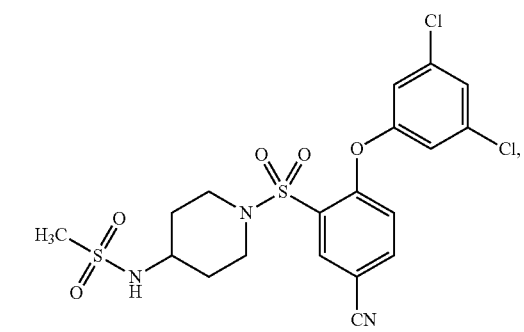

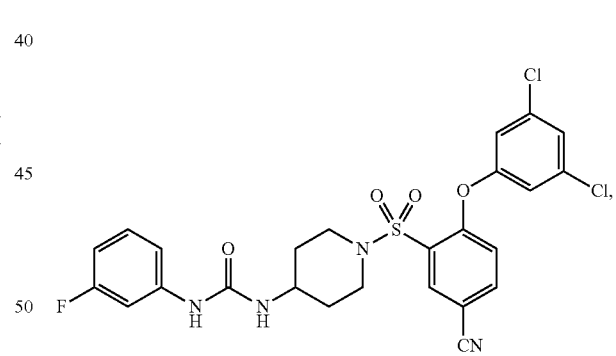

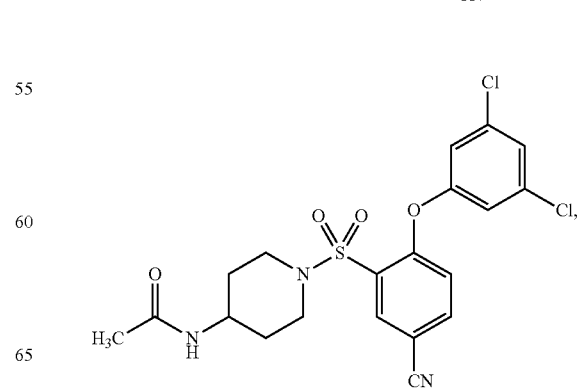

93
-continued
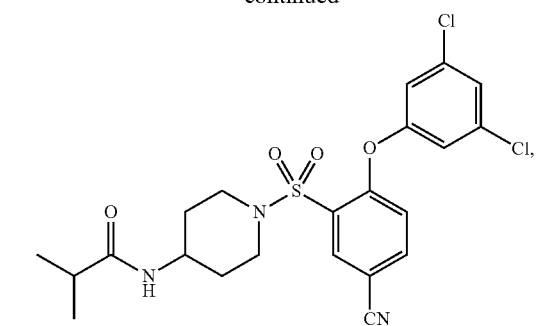
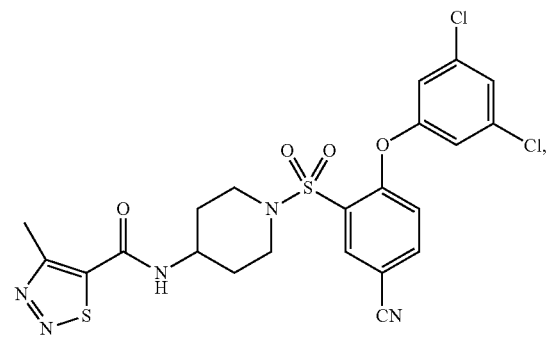
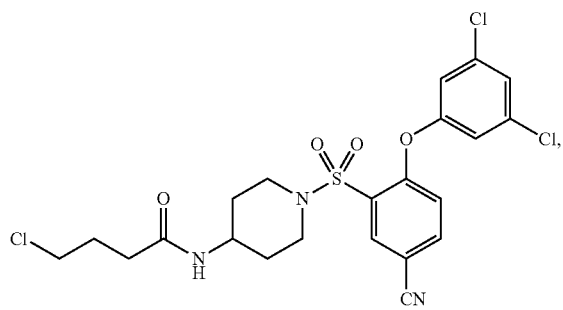
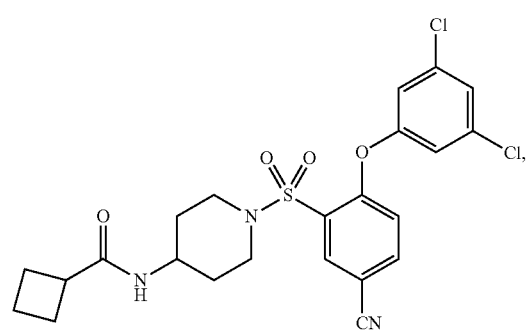
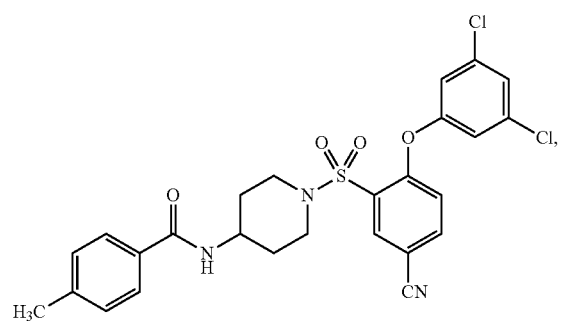
94
-continued
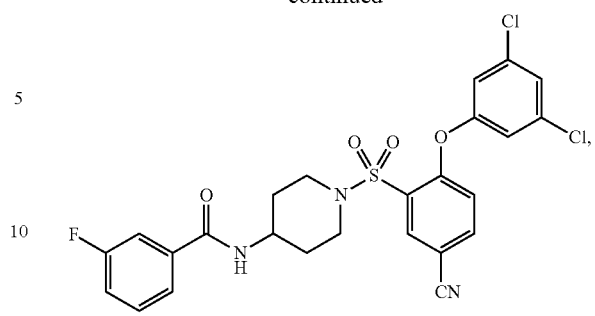
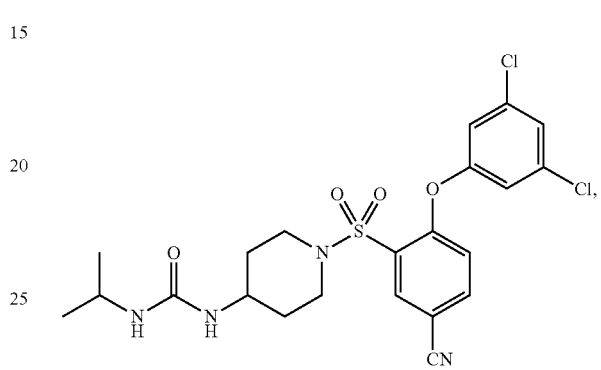
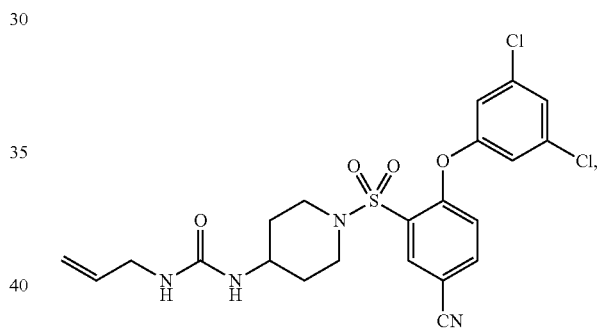
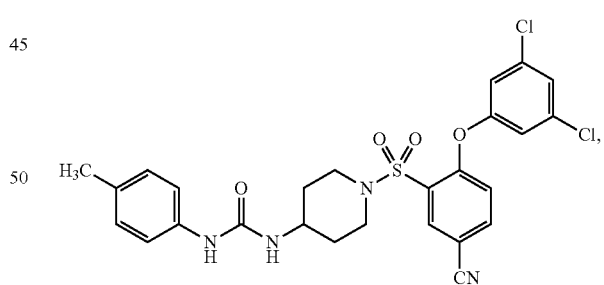
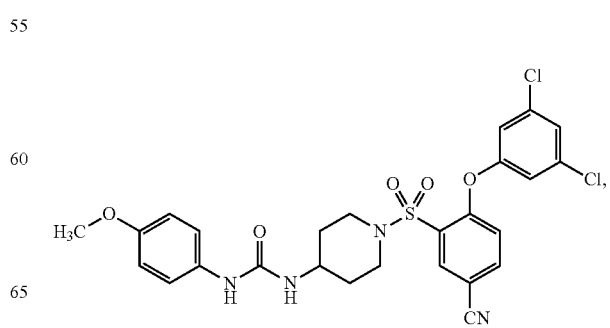

95
-continued
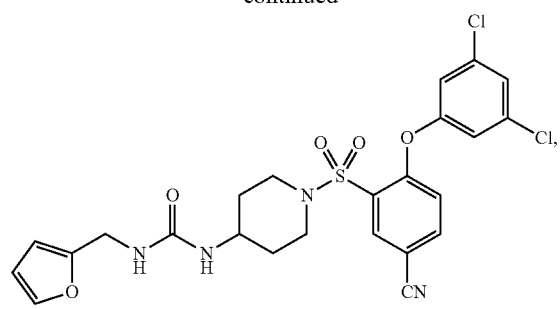
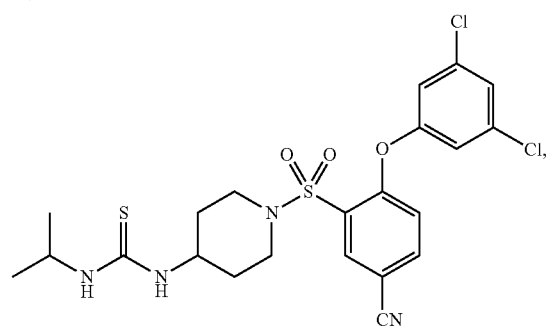
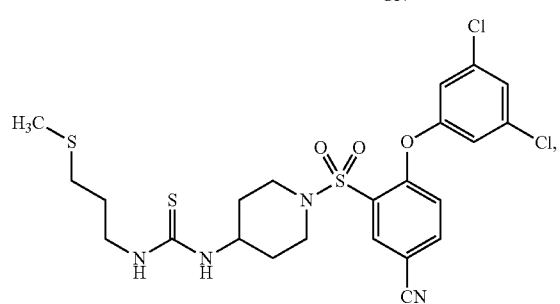
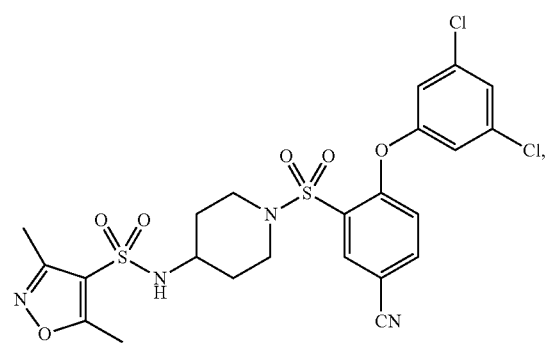
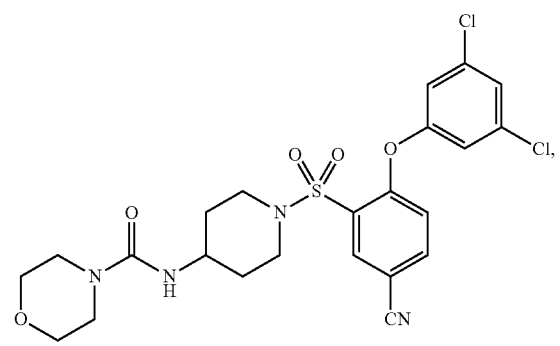
96
-continued
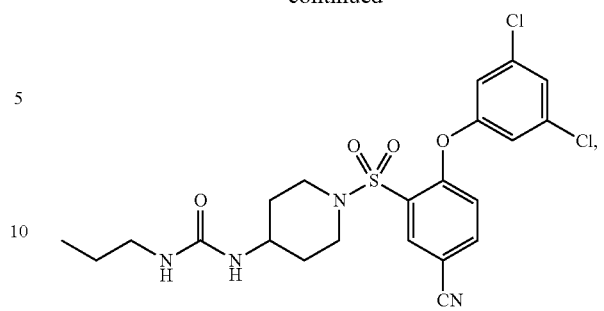
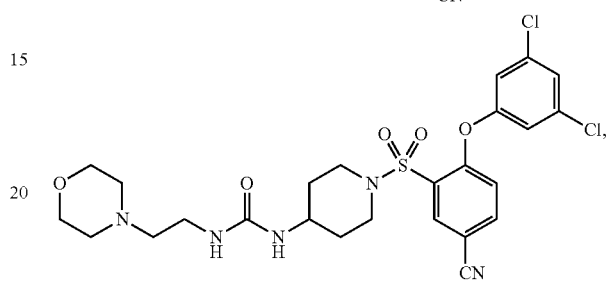
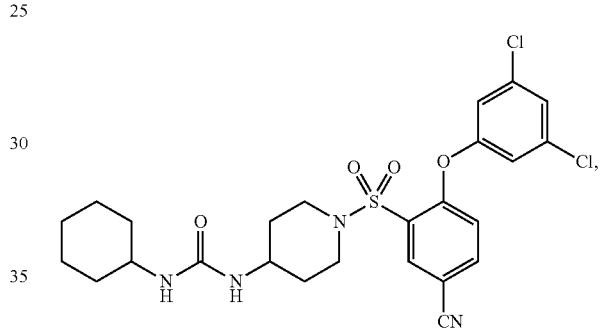
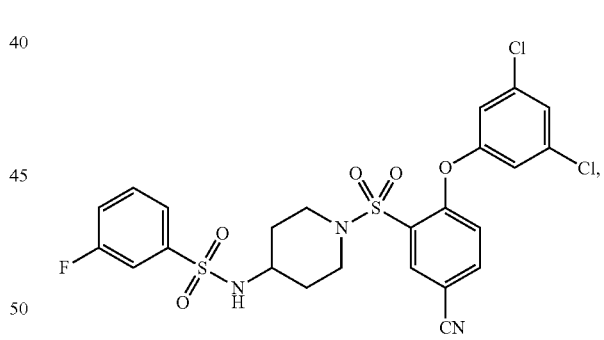
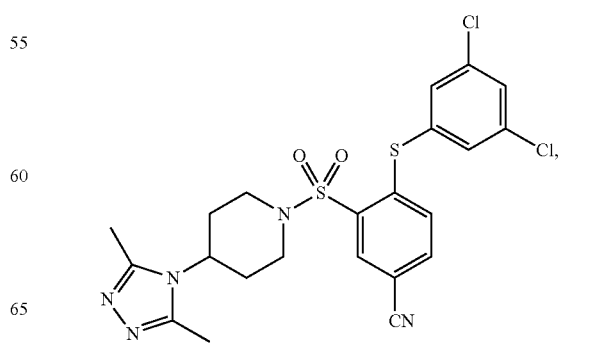

97
-continued
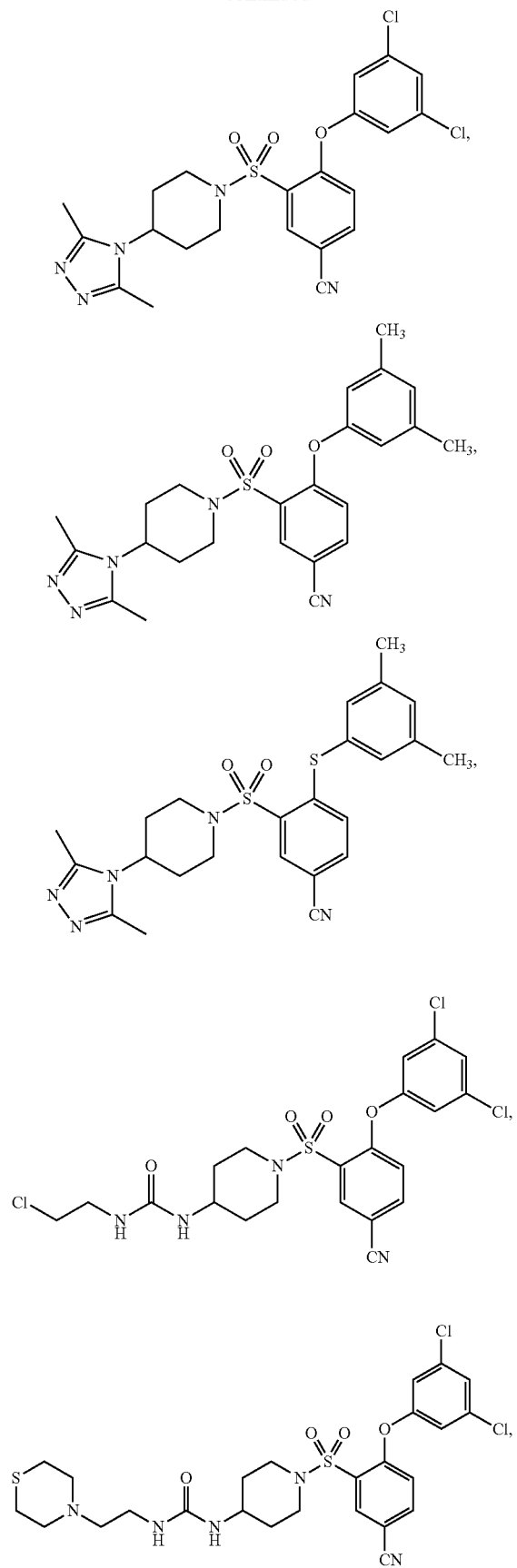
98
-continued
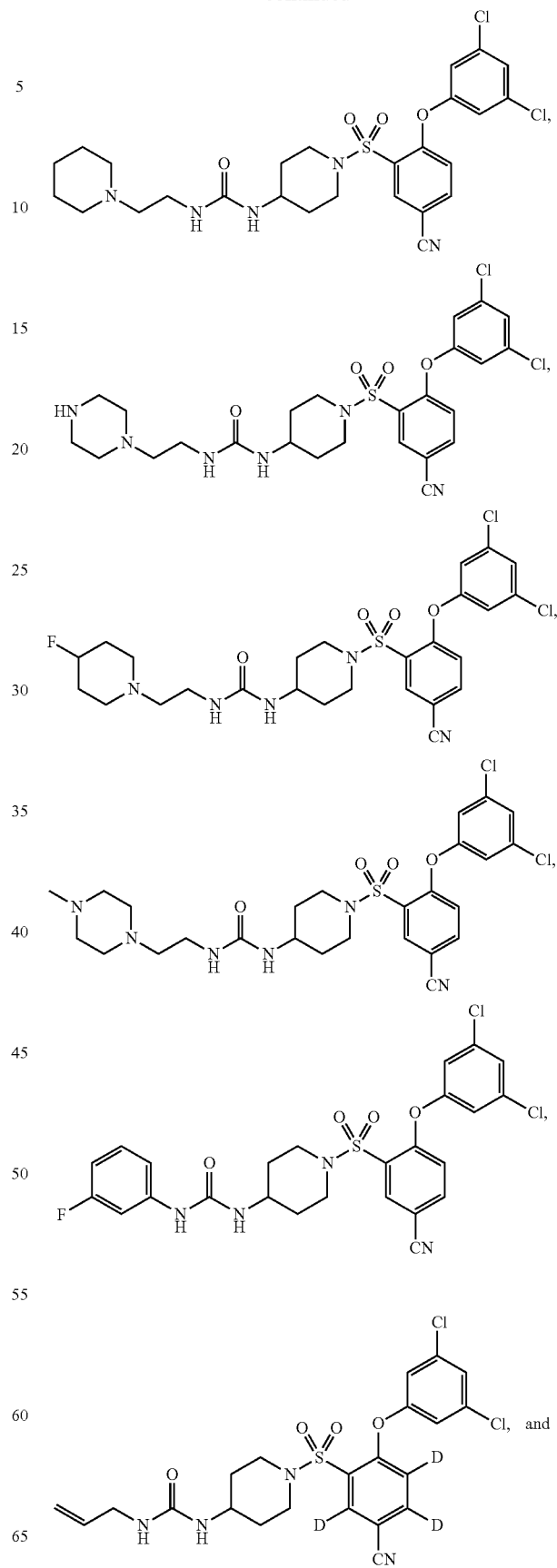

-continued

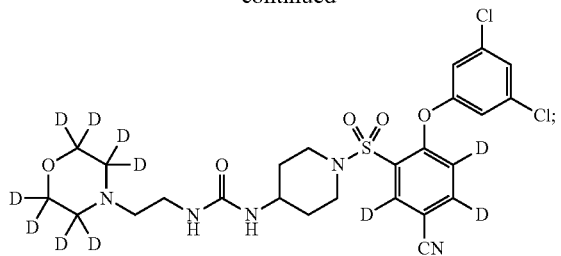

and enantiomers, mixtures of enantiomers, mixtures of two or more diastereomers, tautomers, and mixtures of two or more tautomers thereof and pharmaceutically acceptable salts, hydrates, and prodrugs thereof.

10. A pharmaceutical composition comprising a compound of claim 1, or a pharmaceutically acceptable salt, hydrate, stereoisomer, or tautomer thereof; and one or more pharmaceutically acceptable carriers or excipients.

11. The pharmaceutical composition of claim 10, further comprising a therapeutic agent.

12. The pharmaceutical composition of claim 10, wherein the composition is formulated for single dose administration.

13. The pharmaceutical composition of claim 12, wherein the composition is formulated as oral, parenteral, or intravenous dosage form.

14. The pharmaceutical composition of claim 13, wherein the oral dosage form is a tablet or capsule.

15. A method for the treatment or amelioration of one or more symptoms of a $CCR^3$-mediated disorder, disease, or condition in a subject, which comprises administering to the subject a therapeutically effective amount of the compound of claim 1 wherein the CCR3-mediated disorder, disease, or condition is asthma, exercise induced asthma, allergic rhinitis, atopic dermatitis, chronic obstructive pulmonary disease, or allergic conjunctivitis.

16. The method of claim 15, wherein the compound is administered orally, parenterally, or topically.

17. The method of claim 16, wherein the compound is administered in combination with a second therapeutic agent.

* * * * *